(12) United States Patent
Falligant et al.

(10) Patent No.: US 10,894,140 B2
(45) Date of Patent: Jan. 19, 2021

(54) DEVICE AND METHOD FOR DIFFUSING HIGH CONCENTRATION NO WITH INHALATION THERAPY GAS

(71) Applicant: Mallinckrodt Hospital Products IP Limited, Mulhuddart (IE)

(72) Inventors: John C. Falligant, Mount Horeb, WI (US); Craig R. Tolmie, Stoughton, WI (US)

(73) Assignee: Mallinckrodt Hospital Products IP Unlimited Company, Dublin (IE)

(*) Notice: Subject to any disclaimer, the term of this patent is extended or adjusted under 35 U.S.C. 154(b) by 986 days.

(21) Appl. No.: 15/281,512

(22) Filed: Sep. 30, 2016

(65) Prior Publication Data

US 2017/0095633 A1  Apr. 6, 2017

Related U.S. Application Data

(60) Provisional application No. 62/235,798, filed on Oct. 1, 2015.

(51) Int. Cl.
| | | |
|---|---|---|
| *A61M 16/12* | (2006.01) | |
| *A61M 11/00* | (2006.01) | |
| *A61M 16/20* | (2006.01) | |
| *A61M 16/08* | (2006.01) | |

(52) U.S. Cl.
CPC ............ *A61M 16/12* (2013.01); *A61M 11/00* (2013.01); *A61M 16/0875* (2013.01); *A61M 16/203* (2014.02); *A61M 2202/0208* (2013.01); *A61M 2202/0275* (2013.01); *A61M 2205/3334* (2013.01)

(58) Field of Classification Search
CPC .... A61M 16/12; A61M 16/203; A61M 11/00; A61M 16/0875; A61M 2202/0208; A61M 2202/0275; A61M 2205/3334; A61M 16/122; A61M 16/125; A61M 16/127
See application file for complete search history.

(56) References Cited

U.S. PATENT DOCUMENTS

| | | | |
|---|---|---|---|
| 3,727,627 A | 4/1973 | Bird et al. | |
| 5,036,847 A * | 8/1991 | Boussignac | A61M 16/12 128/203.12 |
| 5,178,138 A * | 1/1993 | Walstrom | A61M 15/0086 128/200.14 |
| 5,365,795 A * | 11/1994 | Brower, Jr. | G01F 1/363 73/861.63 |

(Continued)

FOREIGN PATENT DOCUMENTS

| | | |
|---|---|---|
| EP | 0640357 A1 | 3/1995 |
| EP | 2574394 A1 | 4/2013 |
| WO | 2004064907 A1 | 8/2004 |

OTHER PUBLICATIONS

INOvent Delivery System: Operation and Maintenance Manual (CGA Variant), Datex-Ohmeda, Inc. 2000, 180 pages.

(Continued)

*Primary Examiner* — Kendra D Carter
*Assistant Examiner* — Jonathan S Paciorek
(74) *Attorney, Agent, or Firm* — Servilla Whitney LLC

(57) ABSTRACT

Systems and methods of the present invention can enable high concentration NO to be delivered into ventilator breathing circuits, via a diffusing device, without generating undesirably large amounts of $NO_2$.

26 Claims, 49 Drawing Sheets

NO2 Output vs. NO Gas Velocity, Low Source Concentration

NO2 Output vs. NO Gas Velocity, High Source Concentration

(56) References Cited

U.S. PATENT DOCUMENTS

| | | | |
|---|---|---|---|
| 5,558,083 A * | 9/1996 | Bathe | A61M 16/12 128/203.12 |
| 5,615,669 A | 4/1997 | Olsson et al. | |
| 5,699,790 A | 12/1997 | Bathe et al. | |
| 5,722,392 A | 3/1998 | Skimming et al. | |
| 5,732,693 A | 3/1998 | Bathe et al. | |
| 5,732,694 A | 3/1998 | Bathe et al. | |
| 5,752,504 A * | 5/1998 | Bathe | A61M 16/12 128/203.12 |
| 5,871,009 A | 2/1999 | Rydgren et al. | |
| 5,918,596 A | 7/1999 | Heinonen | |
| 6,109,260 A | 8/2000 | Bathe | |
| 6,125,846 A | 10/2000 | Bathe et al. | |
| 6,142,147 A | 11/2000 | Head et al. | |
| 6,158,434 A | 12/2000 | Lugtigheid et al. | |
| 6,164,276 A | 12/2000 | Bathe et al. | |
| 6,253,766 B1 | 7/2001 | Niles et al. | |
| 6,581,592 B1 | 6/2003 | Bathe et al. | |
| 6,581,599 B1 * | 6/2003 | Stenzler | A61M 16/12 128/203.12 |
| 6,668,828 B1 | 12/2003 | Figley et al. | |
| 6,694,969 B1 | 2/2004 | Heinonen et al. | |
| 6,758,214 B2 | 7/2004 | Fine et al. | |
| 7,040,313 B2 | 5/2006 | Fine et al. | |
| 7,455,062 B2 | 11/2008 | Roehl et al. | |
| 7,523,752 B2 | 4/2009 | Montgomery et al. | |
| 7,762,253 B2 | 7/2010 | Acker et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,371,296 B2 | 2/2013 | Fine et al. | |
| 8,431,163 B2 | 4/2013 | Baldassarre et al. | |
| 8,460,203 B2 | 6/2013 | Ricciardelli | |
| 8,573,209 B2 | 11/2013 | Bathe et al. | |
| 8,573,210 B2 | 11/2013 | Bathe et al. | |
| 8,677,999 B2 * | 3/2014 | Allum | A61M 16/04 128/204.25 |
| 8,776,794 B2 | 7/2014 | Bathe et al. | |
| 8,776,795 B2 | 7/2014 | Bathe et al. | |
| 8,795,741 B2 | 8/2014 | Baldassarre | |
| 8,846,112 B2 | 9/2014 | Baldassarre | |
| 2007/0056587 A1 * | 3/2007 | Travan | A61M 16/1045 128/204.18 |
| 2011/0226241 A1 | 9/2011 | Stenzler et al. | |
| 2011/0240019 A1 | 10/2011 | Fine et al. | |
| 2011/0319783 A1 | 12/2011 | Lindholt et al. | |
| 2012/0167878 A1 * | 7/2012 | Belson | A61F 7/12 128/200.16 |
| 2013/0104885 A1 | 5/2013 | Kobrich et al. | |
| 2013/0108715 A1 | 5/2013 | Kobayashi et al. | |
| 2013/0239962 A1 | 9/2013 | Goldstein | |
| 2013/0239963 A1 | 9/2013 | Goldstein et al. | |
| 2013/0327329 A1 | 12/2013 | Igney et al. | |
| 2014/0127330 A1 | 5/2014 | Fine et al. | |
| 2015/0290417 A1 | 10/2015 | Stenzler et al. | |

OTHER PUBLICATIONS

Connectors / Adapters pamphlet, Mercury Medical, 19 pages.
INOmax DS (Delivery System): Operation Manual (800 ppm INOMAX (nitric oxide) for Inhalation), Ikaria, Inc., 2010, pp. 112.
INOmax DSIR Operation Manual (800 ppm INOMAX (nitric oxide) for inhalation), 2012.
INOmax Label, (Nitric Oxide) for Inhalation, 2009, 9 pages, 2009.
INOmax Label, Nitric Oxide Gas, INO Therapeutics 2013, 2 pages.
Kinetic Molecular Theory & Graham's Law, 10 pages.
PCT International Search Report and Written Opinion in PCT/US2016/054795 dated Nov. 23, 2016, 14 pages.
Using the INOpulse DS Subject Guide, Ikaria, Inc., 2012, 50 pages.
Ellison, T. H., et al., "Mixing of dense fluid in a turbulent pipe flow. Part 1. Overall description of the flow", Department of the Mechanics of Fluids, University of Manchester (1959), 15 pages.
Foubert, L., et al., "A study of mixing conditions during nitric oxide administration using simultaneous fast response chemiluminescence and capnography", British Journal of Anaesthesia 1997, 78: 436-438.
Foubert, L., et al., "Effect of nitric oxide predilution on inhaled nitrogen dioxide concentrations", Anaesthesia, 1999, 54, pp. 220-225.
Martin, Andrew R., et al., "An injection and mixing element for delivery and monitoring of inhaled nitric oxide", BioMed Eng OnLine (2016) 15:103, 14 pages.
Schedin, U., et al., "Formation of nitrogen dioxide from nitric oxide and their measurement in clinically relevant circumstances", British Journal of Anaesthesia 82 (2): 182-92 (1999).
Sokol, Gregory M., et al., "Nitrogen Dioxide Formation during Inhaled Nitric Oxide Therapy", Clinical Chemistry pp. 382-387 (1999).
Weinberger, Barry, et al., "The Toxicology of Inhaled Nitric Oxide", Toxicological Sciences 59, pp. 5-16 (2001).

* cited by examiner

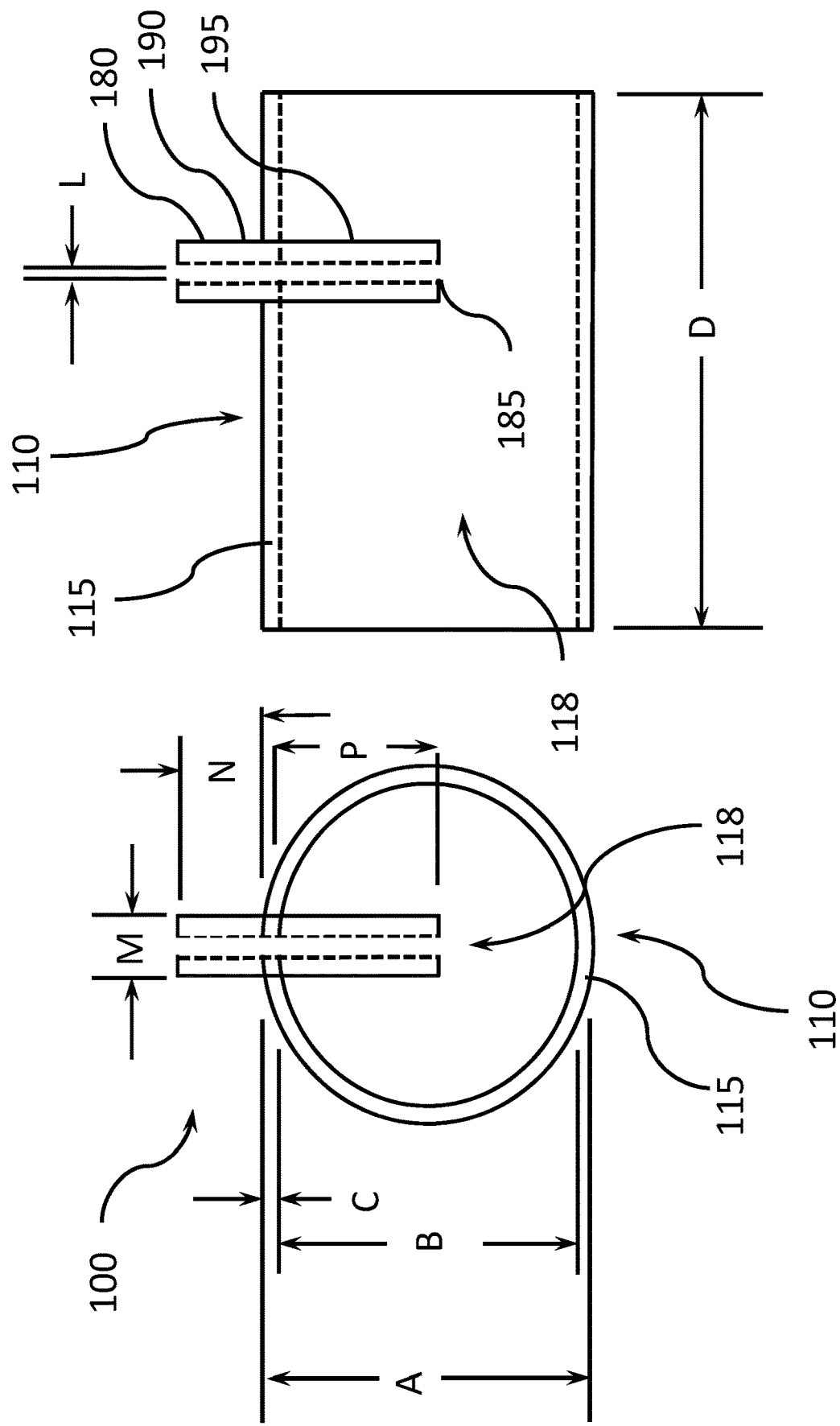

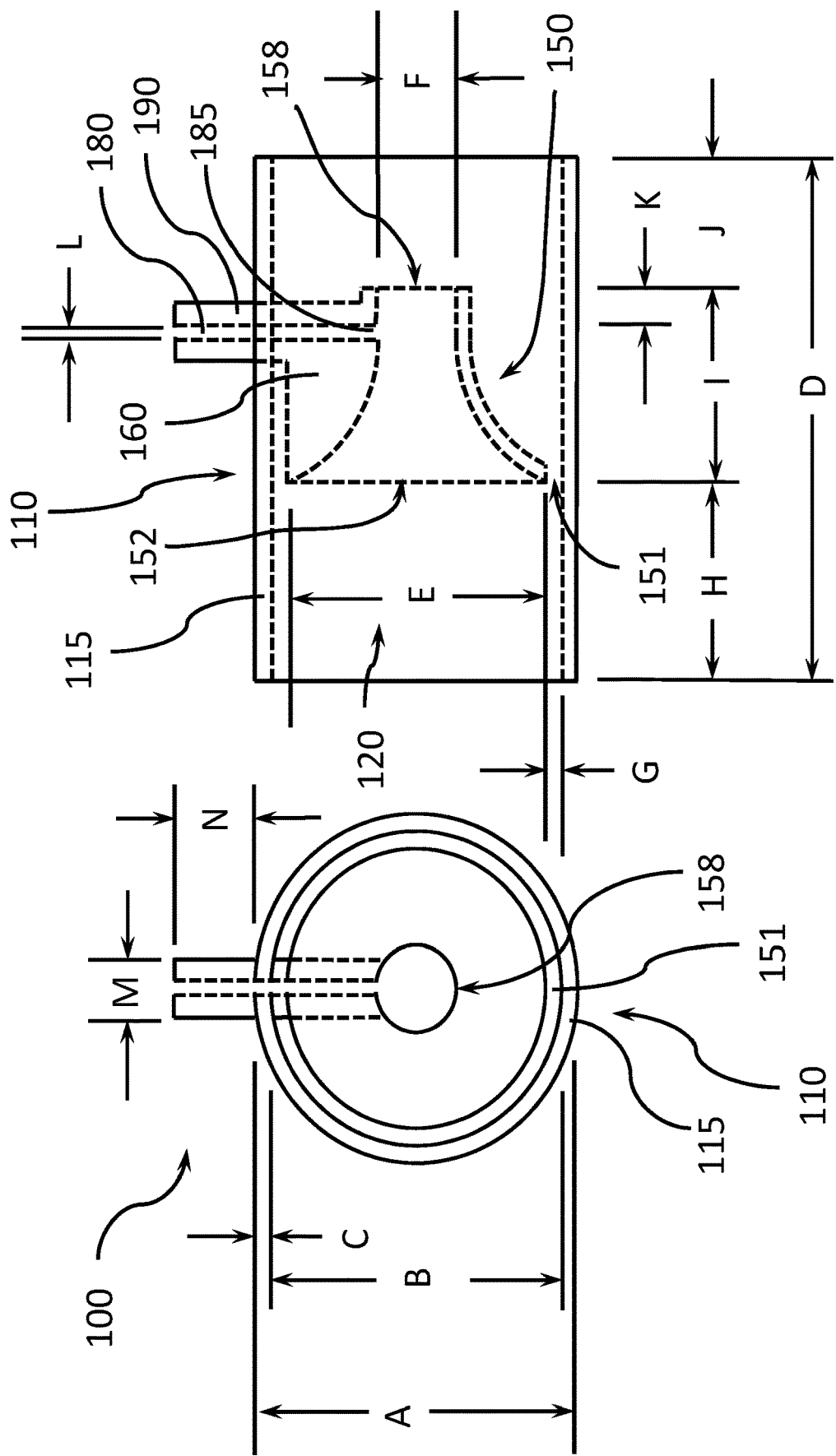

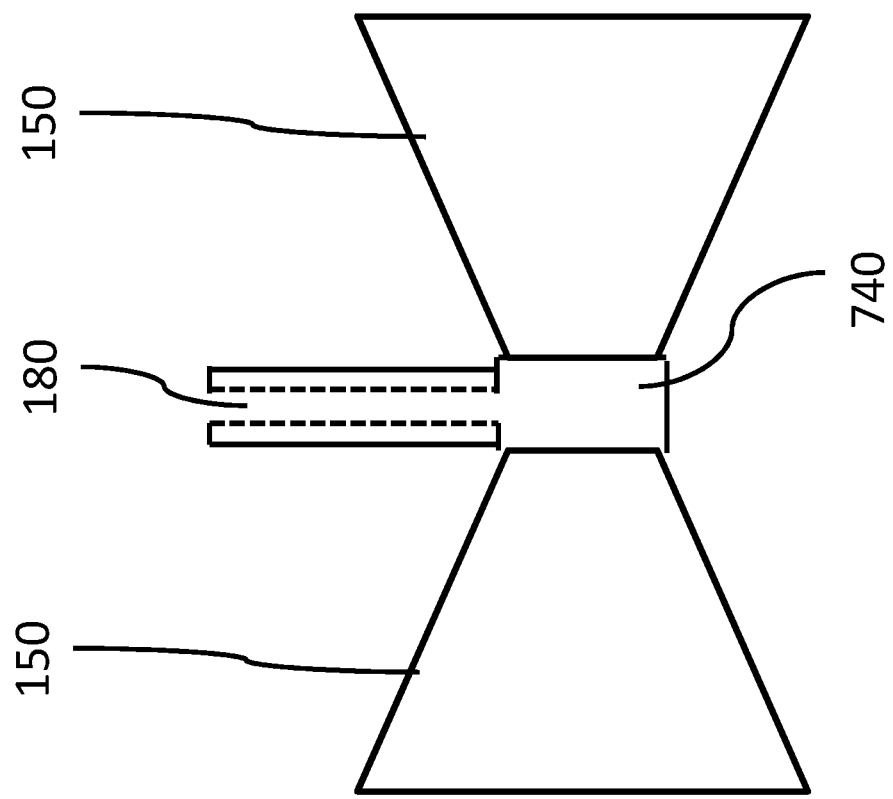

DEVICE AND METHOD FOR DIFFUSING HIGH CONCENTRATION NO WITH INHALATION THERAPY GAS

CROSS-REFERENCE TO RELATED APPLICATIONS

This application claims the benefit under 35 U.S.C. § 119(e) to U.S. Provisional Application No. 62/235,798, filed Oct. 1, 2015, the entire contents of which are incorporated herein by reference in their entirety.

TECHNICAL FIELD

Principles and embodiments of the present invention relate generally to a device for combining nitric oxide (NO) with other gases being administered to a patient for inhalation therapy.

BACKGROUND

A number of gases have been shown to have pharmaceutical action in humans and animals. One such gas is nitric oxide (NO) that, when inhaled, acts to dilate blood vessels in the lungs, improving oxygenation of the blood and reducing pulmonary hypertension. In the field of inhalation therapy for various pulmonary conditions such as acute pulmonary vasoconstriction, hypertension and thromboembolism, or inhalation injury, treatment has included the use of the therapeutic gas NO supplied from a gas cylinder. More specifically, this gaseous NO for inhalation therapy is supplied to a patient from a high pressure gas cylinder containing NO. For example, such an approach is disclosed in U.S. Pat. No. 5,558,083 entitled "Nitric Oxide Delivery System", which is incorporated herein by reference in its entirety.

Inhaled nitric oxide (INO) therapy, generally speaking, involves delivering a concentration of NO, at a set dose, to mechanically ventilated patients. NO delivery systems of this type (wrap-around style) can sense fresh gas flow in the inspiratory limb of the mechanical ventilator, and ratiometrically deliver NO from source cylinders into the inspiratory limb of the ventilator, via an injector module, to achieve a prescribed patient dose.

Typically speaking, the concentration of the NO source (e.g., from the source cylinders) may be about 800 ppm NO. As discussed above, this NO source gas at 800 ppm can be proportionally delivered (e.g., ratio-metrically delivered) into fresh gas flow such that the concentration of NO in the fresh gas flow is about 5 to 80 ppm.

Although INO therapy has many benefits, it has been found that when delivering NO into fresh gas flow, nitrogen dioxide ($NO_2$), a toxic gas, can be generated by reacting with $O_2$ in fresh gas flow. More specifically, the formation of nitrogen dioxide is proportional to the square of the NO concentration multiplied by the concentration of $O_2$.

The kinetics and rate equation for the conversion of NO to $NO_2$ is given by:

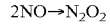

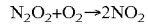

Thus, giving a formation rate of $NO_2 = k[NO]^2[O_2]$, where k is in units of $L \cdot mol^{-1} \cdot s^{-1}$, or in partial pressures for the gases.

Accordingly, the amount of $NO_2$ produced (ppm $NO_2$) is related to the square of the NO concentration and is linear to the oxygenation concentration and time.

In light of the above, NO delivered into a ventilator breathing circuit from a low concentration NO source (e.g., 100 ppm, 400 ppm, and 800 ppm NO cylinders) may not result in undesirably high amounts of $NO_2$, for example >1 ppm; however, following the above kinetics, the use of NO delivered into a ventilator breathing circuit from a high concentration source (e.g., 2000 ppm, 5000 ppm, and 10,000 ppm NO cylinders) would be expected to generate an unacceptable amount of toxic $NO_2$, for example >1 ppm $NO_2$ generated when providing a 40 ppm NO dose with 60% $O_2$. Theoretically, for the same NO therapy dose, $NO_2$ from a 5000 ppm source gas may have a formation rate to 39 times greater than an 800 ppm source.

Some have attempted to address this problem using varying techniques; however, these techniques may not work in specific systems, may not work when delivering high concentration NO, may not work at all, or can fail to address the actual cause of $NO_2$ generation and/or underlying factors in $NO_2$ generation not previously appreciated. Accordingly a need exists for systems and methods of reducing $NO_2$ generation that work in specific systems, address the actual cause of $NO_2$ generation and/or the underlying factors not previously appreciated.

SUMMARY

Systems and methods of the present invention can be used to reduce $NO_2$ generated when, for example, being delivered into fresh gas flow in a ventilator breathing circuit. Further, systems and methods of the present invention can enable high concentration NO to be delivered into ventilator breathing circuits, via a diffusing device, without generating undesirably large amounts of $NO_2$ for example >1 ppm $NO_2$ for a dose of 40 ppm NO with 100% $O_2$. Use of high concentration NO sources (e.g., 2000, 4880, 10,000 ppm NO cylinders) can provide benefits such as, but not limited to, the use of smaller NO gas cylinders, which allows increased portability and introducing smaller volumes of the high concentration gas into the ventilator gas stream, and less dilution of oxygen-enriched Fresh Gas Flow (FGF) by the NO and carrier $N_2$ gases. It has surprisingly been found that introduction of smaller NO volumes with diffusion at equivalent or higher rates can generate less $NO_2$ overall with shorter diffusion time associated with smaller gas volume. The issues addressed herein relate to at least rapidly reducing NO concentration before large concentrations of $NO_2$ can be formed.

There are several ways to address the above problems, including reducing the time that high concentrations of NO exist within the ventilator gas stream, which may be achieved by increasing the rate that the NO diffuses into the other gases, and/or decreasing the residence time of the high concentration NO in the ventilator breathing circuit prior to being rapidly diffused. This reduction in time may be achieved at the immediate point of NO injection, through methods minimizing transient NO concentration time from high (source) concentration to low (set dose) concentration. Very rapid NO concentration reduction from source to set dose at the immediate point of injection significantly reduces $NO_2$ generation, and may be accomplished through a variety of methods, including but not limited to methods such as gas mixing, gas diffusion, thermal effects, intersecting gas stream orientations, intersecting gas stream velocities, or any combinations thereof. The transient NO concentration time, or time NO resides in FGF substantially above set dose, is the time $NO_2$ can be generated at a significantly higher rate compared with the time NO resides in FGF at or near set dose. Stated differently, it is acknowledged that $NO_2$ continues to be generated even after the homogeneous NO concentration is achieved. However, $NO_2$ generation in regions where NO concentration nears set dose is linear with $O_2$ concentration and time, and therefore at a significantly lower rate in comparison to $NO_2$ generation observed during the time of transient NO concentration.

Principles and embodiments of the present invention relate generally to a device and methods of treating patients with NO inhalation therapy involving a high concentration NO source. However, although the methods, systems and devices described herein are discussed in the context of high concentration NO sources, the methods, systems and devices described herein can also be applied to lower concentration NO sources, such as those at or below 800 ppm NO.

Aspects of the present invention relate to a device that combines a gas stream comprising NO and a fresh gas flow stream comprising molecular oxygen ($O_2$) for delivery to a patient, wherein the diffusing of NO and $O_2$ occurs sufficiently rapidly that production of $NO_2$ is minimized, so less than 1 ppm of $NO_2$ is delivered to a patient and/or generated in the ventilator circuit.

In various embodiments, the concentration of NO in the patient inspired gas is in the range of about 1 ppm to about 80 ppm, or alternatively 5 ppm to about 80 ppm, or about 20 ppm to about 60 ppm. Other exemplary NO concentrations for the set dose include about 1 ppm, about 2 ppm, about 3 ppm, about 4 ppm, about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, about 75 ppm or about 80 ppm.

In various embodiments, the concentration of the NO source is in the range of about 200 ppm to about 10,000 ppm, or about 400 ppm to about 10,000 ppm, or greater than 800 ppm to about 10,000 ppm, or about 1,000 ppm to about 5,500 ppm. Other exemplary NO concentrations of the NO source include about 200 ppm, about 300 ppm, about 400 ppm, about 500 ppm, about 600 ppm, about 700 ppm, about 800 ppm, about 1000 ppm, about 1200 ppm, about 1500 ppm, about 2000 ppm, about 2200 ppm, about 2400 ppm, about 2440 ppm, about 2500 ppm, about 3000 ppm, about 3500 ppm, about 4000 ppm, about 4500 ppm, about 4800 ppm, about 4880 ppm, about 5000 ppm, about 6000 ppm, about 7000 ppm, about 8000 ppm, about 9000 ppm or about 10,000 ppm.

In various embodiments, $NO_2$ levels produced using a high concentration NO source (such as a 4880 or a 5000 ppm NO source) can be comparable to or less than those produced with lower concentration NO sources (such as a 200 ppm or 800 ppm NO source).

Aspects of the present invention relate to a method of rapid NO concentration reduction from source concentration to set dose, by increasing the mixing and/or diffusing efficiency of NO within a respiratory gas, fresh gas flow, for the treatment of various pulmonary conditions.

Aspects of the present invention relate to a diffusing device for injecting a high concentration gas into a transverse gas stream comprising a body comprising a wall having a thickness, an outer surface, and an inner surface surrounding a hollow internal region, a projection extending from the inner surface of the body, and an injection channel passing through the wall and projection to an injection port located where the velocity of the fresh gas flow is high (e.g., centrally located in the cross section of the body, where directed to be higher, etc.). As used herein, a "high velocity" of gas flow is any portion of a gas flow that has a higher velocity than the velocity of the gas flow that is at or close to an edge boundary (e.g. the walls of a tube). Due to the no-slip condition, gas flow at the edge boundary has a velocity of zero, and due to the viscosity of the gas, the gas flow closer to the zero-velocity gas has a lower velocity than the gas flow that is farther from the edge boundary and the zero-velocity gas.

Accordingly, in exemplary embodiments, the high concentration gas is injected into a portion of the transverse gas stream that is a distance from the edge boundary (e.g. wall).

Aspects of the present invention relate to a diffusing device for injecting a high concentration gas (e.g., greater than 800 to 10,000 ppm NO) into a transverse gas stream, comprising a body comprising a wall having a thickness, an outer surface and an inner surface, a projection extending from the inner surface of the annular body, a tapered section comprising a wall having a thickness, an outer surface and an inner surface, an inlet end having a first diameter, and an outlet end having a second diameter opposite the inlet end, wherein the second diameter is smaller than the first diameter, and wherein the tapered section is connected to and suspended from the projection, such that the projection forms a support for the tapered section, and an injection channel passing through the projection to an injection port in the inner surface of the tapered section. In exemplary embodiments, gas flow from the injection channel, and in turn, out of the injection port, can be directed to flow into the transverse gas stream where the fastest gas velocity exists.

In one or more embodiments, the diffusing device for injecting a high concentration gas (e.g., greater than 800 to 10,000 ppm NO) into a transverse gas stream does not comprise a tapered section suspended from the projection. In various embodiments, the projection extends radially from the inner surface of the annular body into approximately the center of the open volume surrounded by the cylindrical wall, and an injection channel passes through the projection to an injection port.

In various embodiments, the injection port has an inside diameter in the range of about 0.58 mm (0.023 in.) to about 4.75 mm (0.187 in.), or about 0.8 mm (0.031 in.) to about 2.4 mm (0.094 in.), or about 1.12 mm (0.044 in.) to about 2.29 mm (0.090 in.), or about 1.83 mm (0.072 in.). Exemplary lower limits include about 0.58 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm and about 1.8 mm. Exemplary upper limits include about 4.75 mm mm, about 4.5 mm, about 4 mm, about 3.5 mm, about 3 mm, about 2.5 mm, about 2.4 mm, about 2.29 mm, about 2.2 mm, about 2.1 mm, about 2 mm and about 1.9 mm.

In one or more embodiments, the diffusing device may be configured and dimensioned to be inserted into and in fluid communication with a breathing circuit scaled for a neonate, a pediatric, or an adult with a corresponding and appropriate ventilator tube size. In various embodiments, the annular body has an outside diameter in the range of about 10 mm to about 25 mm, and an inside diameter in the range of about 10 mm to about 25 mm, wherein the inside diameter is smaller than the outside diameter by the thickness of the cylindrical wall.

In various embodiments, the thickness of the cylindrical wall 'C' is in the range of about 1 mm to about 3.175 mm, or about 1.5 mm.

In various embodiments, the diffusing device is configured and dimensioned for insertion into respiratory tubing, such as for a ventilator breathing circuit.

In various embodiments, the first diameter is in the range of about 6 mm to about 18 mm, and the second diameter is in the range of about 3.17 mm to about 9.5 mm, where the first diameter is greater than the second diameter.

In various embodiments, the tapered section is symmetrical around an axis, and the injection channel forms an angle in the range of about 60° to about 120° with the axis of the tapered section.

In various embodiments, the tapered section is funnel shaped.

In various embodiments, the tapered section is truncated cone shaped.

In various embodiments, the tapered section is bell shaped.

Aspects of the present invention relate to a method of diffusing a high concentration gas into a transverse gas stream, comprising passing at least a portion of a first gas through a tapered section comprising a wall having a thickness, an outer surface and an inner surface, an inlet end having a first diameter, and an outlet end having a second diameter opposite the inlet end, wherein the second diameter is smaller than the first diameter and passing a second gas stream through an injection channel to an injection port in the inner surface of the tapered section, wherein the second gas stream enters and at least partially diffuses with the first gas stream within the tapered section.

In various embodiments, the method further comprises passing at least a portion of the first gas around at least a portion of the outer surface of the tapered section, wherein the tapered section is within an annular body having an outer surface and an inner surface, and an inside diameter that is larger than the first diameter of the tapered section.

In various embodiments, a support connects the annular body to the tapered section the injection, so the second gas passing through the injection channel passes through the support to the injection port.

In various embodiments, the second gas stream initially enters the first gas stream at an angle in the range of about 60° to about 120°.

In various embodiments, the first gas is a breathable gas comprising molecular $N_2$ and molecular $O_2$, and the second gas comprises molecular NO and molecular $N_2$.

In various embodiments, the concentration of NO in the second gas is in the range of greater than 800 ppm to about 5,500 ppm.

In various embodiments, the first gas enters the annular body at a flow rate in the range of about 0 liters per minute (SLPM) to about 120 SLPM, or about 0.5 SLPM to about 60 SLPM, or about 0.5 SLPM to about 2 SLPM.

In various embodiments, the first gas (e.g., FGF) is a breathable gas comprising molecular $N_2$ and molecular $O_2$, and the second gas comprises molecular NO at a concentration in the range of greater than 1000 ppm to about 5,500 ppm, and the second gas exits the injection port at a flow rate in the range of about 0.05 milliliters per minute (SMLPM) to about 2 SLPM, or about 0.1 SMLPM to about 1 SLPM.

Oxygen concentration in patient ventilator circuits may be set to a value over the continuous range from medical air (21% $O_2$) to medical oxygen (100% $O_2$), but may be generally elevated to 60% for patients receiving INO therapy.

In various embodiments, the flow rate of the second gas is linearly proportional to the flow rate of the first gas.

In various embodiments, the velocity of the first gas is greater at the second diameter of the tapered section than the velocity of the first gas at the first diameter of the tapered section, wherein the second gas enters the first gas at a point of greater or equal velocity.

Aspects of the invention also relate to a method of diffusing a high concentration gas into a transverse gas stream, comprising passing at least a portion of a first gas through a hollow internal region of a body having an inner surface surrounding the hollow internal region; and passing a second gas stream through an injection channel to an injection port projecting into the hollow internal region of the body, wherein the second gas stream enters and at least partially diffuses with the first gas stream within the hollow internal region

BRIEF DESCRIPTION OF THE DRAWINGS

Further features of embodiments of the present invention, their nature and various advantages will become more apparent upon consideration of the following detailed description, taken in conjunction with the accompanying drawings, which are also illustrative of the best mode contemplated by the applicants, and in which like reference characters refer to like parts throughout, where:

FIGS. 8A-B illustrate an exemplary embodiment of a device for diffusing a high NO source concentration, low volume gas flow and a high volume gas flow;

FIGS. 8C-D illustrate another exemplary embodiment of a device for diffusing a high NO source concentration, low volume gas flow and a high volume gas flow;

FIG. 10 illustrates an exemplary embodiment of a bi-directional tapered section;

DETAILED DESCRIPTION

Figure 1A:
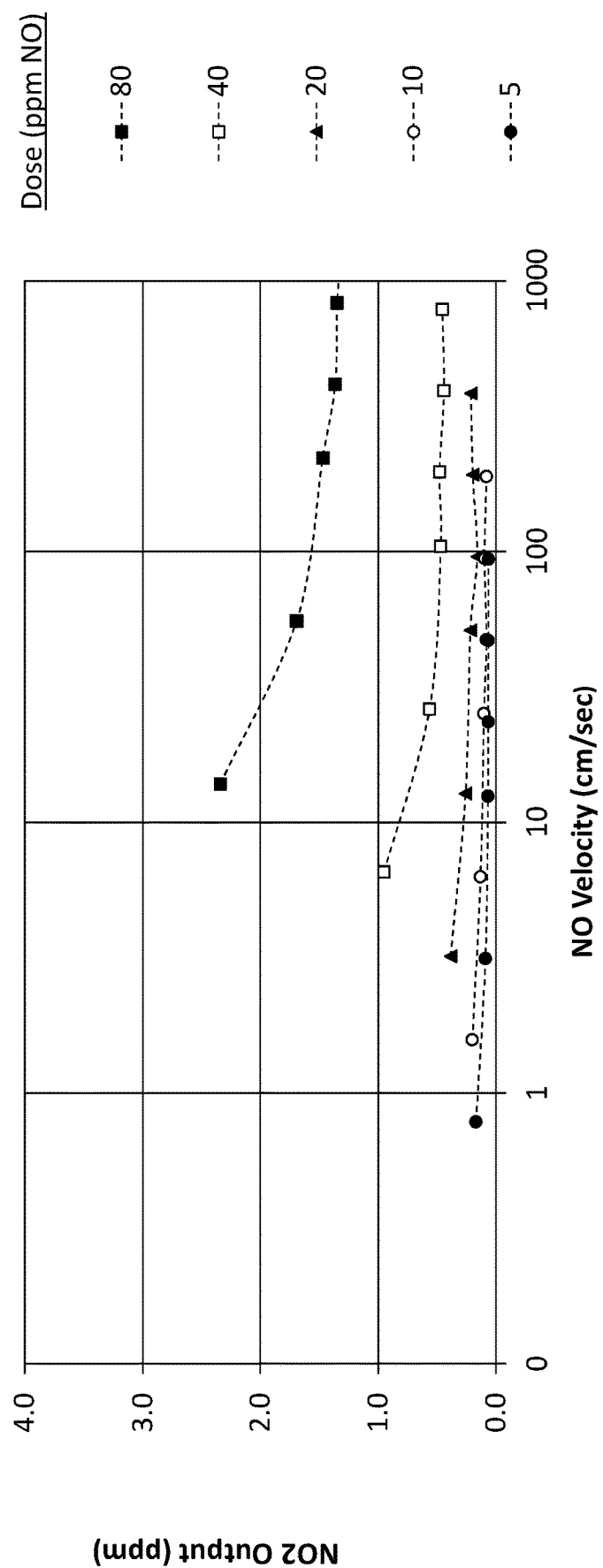
FIGS. 1A-F show the $NO_2$ generated after injecting NO into oxygen-enriched air under various conditions.

The present invention, generally speaking, is directed to systems and methods of injecting NO into fresh gas flow in the inspiratory limb of a ventilator breathing circuit such that $NO_2$ generation is minimized. The present invention takes advantage of previously unknown factors which applicant surprisingly found affect $NO_2$ generation. More specifically, systems and methods of the present invention can be used to deliver NO from a source of high concentration NO (e.g., 5000 ppm NO source) into fresh gas flow in the inspiratory limb of a ventilator breathing circuit such that $NO_2$ generation is substantially minimized and/or the $NO_2$ generated is within a desired range (e.g., less than 1 ppm $NO_2$ delivered to the patient, the same or less $NO_2$ as generated by substantially lower concentration NO sources using conventional injector modules, etc.) by factoring in variables such as, but not limited to, location of injection of NO into fresh gas flow, fresh gas flow velocity, NO flow velocity, and/or ratio of impinging velocity of NO and fresh gas flow, to name a few.

Further, systems and methods of the present invention can be used with a ventilator breathing circuit by not substantially causing pressure drop, for example less than 1.5 cm $H_2O$ at 60 SLPM, minimizing flow profile changes, minimizing the increase in the compressible volume of fresh gas flow, and/or enabling for patient spontaneous breathing in the ventilator breathing circuit. Further still, systems and methods of the present invention can be used immediately downstream from flow sensors that require the fresh gas flow be laminar and/or can be used immediately upstream from at least one gas sampling line.

"Compressible volume" means the volume of a conduit and all components in fluid communication with and in line with the flow path of the conduit. For example, the compressible volume of breathing circuit is the volume of the breathing circuit and all of the components within it (e.g. humidifier, injector module, sample T's).

As used herein, "diffusion", "diffusing" and related terms refer to the overall transport of molecules of one gas (e.g. NO) into and throughout a stream of another gas (e.g. oxygen-enriched air). The use of the terms "diffusion", "diffusing" and related terms does not exclude the contribution of bulk fluid motion or other transport phenomena to the mixing and homogenization of two or more gas streams.

As noted above, prior to applicant's research, it was believed that $NO_2$ formation was predicated on the concentration of NO and $O_2$ (e.g., parts-per-million of NO, percent of $O_2$ (otherwise known as $FiO_2$)), as well as the distance/dwell time between gas mixing and the patient. Following this belief, delivery of NO from a high concentration source (e.g., 5000 ppm, 10,000 ppm NO cylinder) would result in substantially high levels of $NO_2$. For example, a 4880 ppm NO cylinder concentration reduced down to a set dose of 10 ppm is a turn down ratio of 488:1, whereas a 800 ppm cylinder concentration reduced down to a 10 ppm set dose has a turn down ratio of 80:1, theoretically $NO_2$ is generated at a rate approximately 37 times greater with a 4880 ppm NO supply than with a 800 ppm NO supply cylinder for a dose of 10 ppm. Without a means of overcoming this problem, high concentrations sources of NO cannot be used for INO therapy as this would result in delivery of undesirably high levels of $NO_2$ to a patient, and many benefits associated with using high concentration sources of NO for INO therapy (e.g., smaller NO supply cylinders, increased portability of INO therapy devices, smaller volumes of NO-containing gas (e.g., nitrogen and NO gas blends) in the breathing circuit, reduced inspired oxygen dilution due to smaller injected NO-containing gas volumes, etc.) would be unrealized.

In exemplary embodiments, using a higher concentration source gas can reduce a portion of the $NO_2$ delivered to a patient. For example, the higher the NO concentration of the source gas, the smaller the volume of source gas required to be delivered to obtain the desired set NO dose. Even with the same $NO_2$ concentration in the source gas (e.g. the same $NO_2$ concentration in a gas cylinder), by using this lower volume of source gas, less volume of $NO_2$ from the source gas would be delivered and hence the patient receives less $NO_2$ from the NO source (e.g. cylinder).

In light of at least these unrealized benefits, applicant conducted extensive research and testing into $NO_2$ generation when injecting NO into the inspiratory limb of a ventilator breathing circuit.

From this research and testing, it was surprisingly found that $NO_2$ formation was greater during the expiratory phase of ventilation, in which fresh gas flow in the inspiratory limb of a ventilator is substantially slower, laminar (non-turbulent) than during the inspiratory non-laminar (turbulent) phase of ventilation. With this knowledge, further research and testing was conducted to determine the relationship between the $NO_2$ output and variables such as the impinging velocity of the NO-containing gas, the flow rate of the FGF, and the NO dose. In each of these experiments, the fresh gas was oxygen-enriched (e.g. 60% $O_2$/air), the $NO_2$ concentration was measured at a distance beyond the NO injection point (e.g. 1,000 mm), and the NO source concentration was either a low concentration (e.g. 800 ppm NO) or a high concentration (e.g. 4880 ppm NO). The NO was injected and the gases were mixed using a conventional injector module. The results of this testing are shown in Tables 1-2 and FIGS. 1A-F.

TABLE 1

NO$_2$ Generated with Low Concentration NO Source

| | | NO$_2$ Delivery (ppm NO$_2$) NO Dose | | | | |
|---|---|---|---|---|---|---|
| | | 5 | 10 | 20 | 40 | 80 |
| FGF | 0.5 | 0.17 | 0.2 | 0.39 | 0.95 | 2.3 |
| Flow | 2 | 0.089 | 0.13 | 0.26 | 0.56 | 1.7 |
| Rate | 8 | 0.067 | 0.101 | 0.22 | 0.47 | 1.5 |
| (SLPM) | 15 | 0.065 | 0.08 | 0.16 | 0.48 | 1.4 |
| | 30 | 0.065 | 0.096 | 0.2 | 0.44 | 1.4 |
| | 60 | 0.063 | 0.081 | 0.21 | 0.46 | 1.3 |

TABLE 2

NO$_2$ Generated with High Concentration NO Source

| | | NO$_2$ Delivery (ppm NO$_2$) NO Dose | | | | |
|---|---|---|---|---|---|---|
| | | 5 | 10 | 20 | 40 | 80 |
| FGF | 0.5 | 1.9 | 2.6 | 3.4 | 2.9 | 3.3 |
| Flow | 2 | 0.8 | 0.63 | 0.36 | 0.57 | 1.7 |
| Rate | 8 | 0.088 | 0.089 | 0.14 | 0.41 | 1.2 |
| (SLPM) | 15 | 0.073 | 0.075 | 0.11 | 0.34 | 1.2 |
| | 30 | 0.047 | 0.089 | 0.13 | 0.34 | 1.2 |
| | 60 | 0.032 | 0.055 | 0.14 | 0.34 | 1.2 |

Figure 1B:
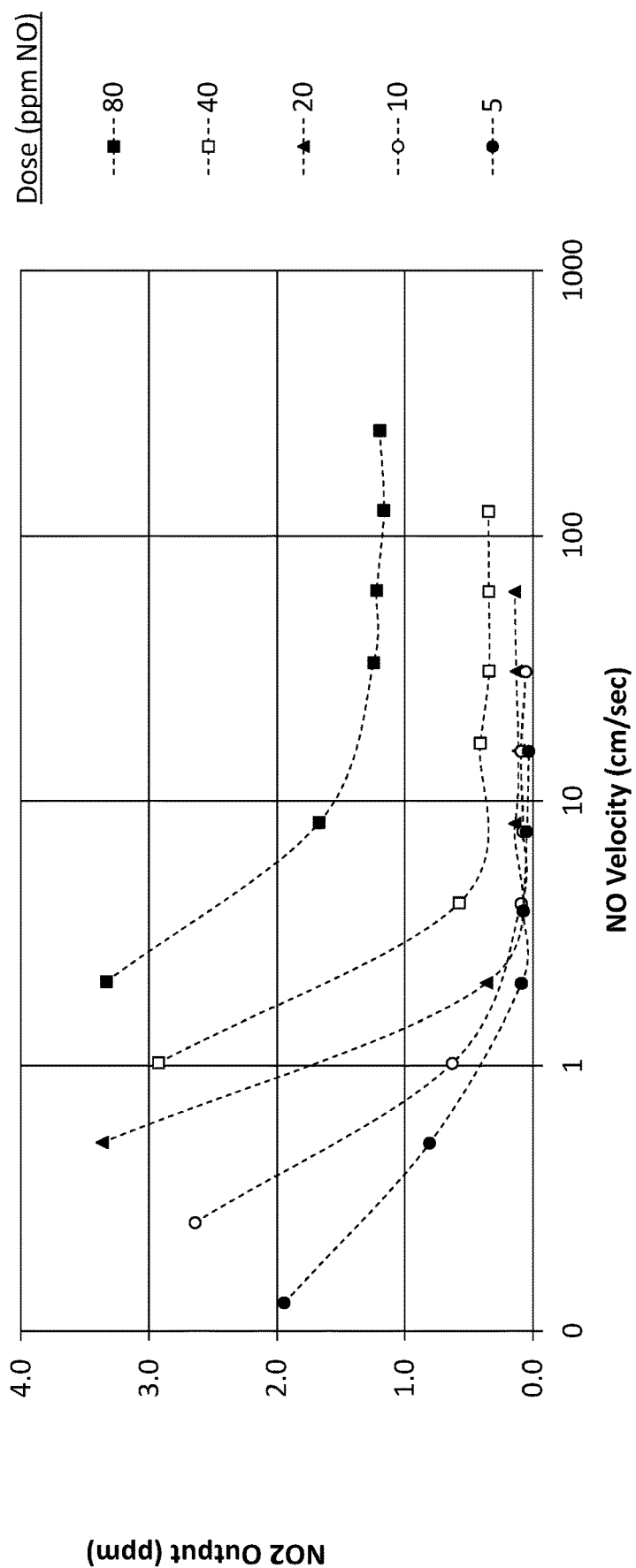
Figure 1C:
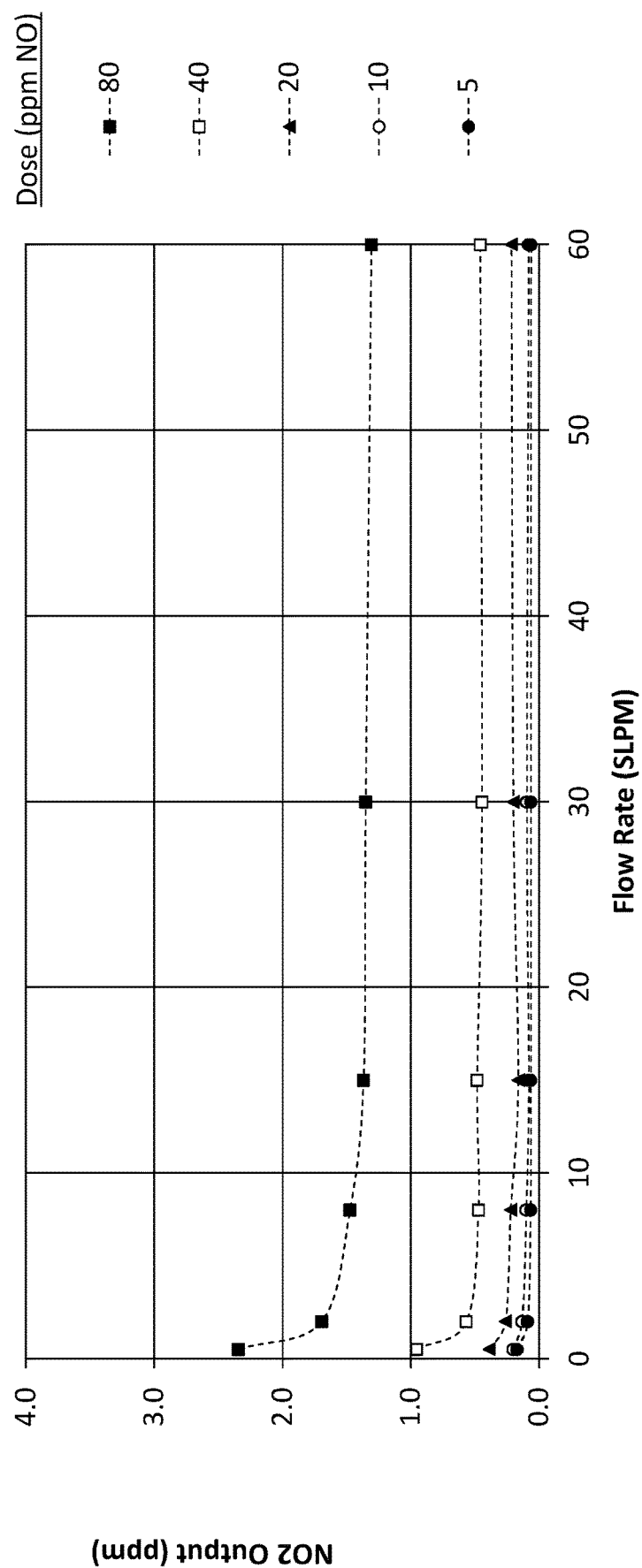
Figure 1D:
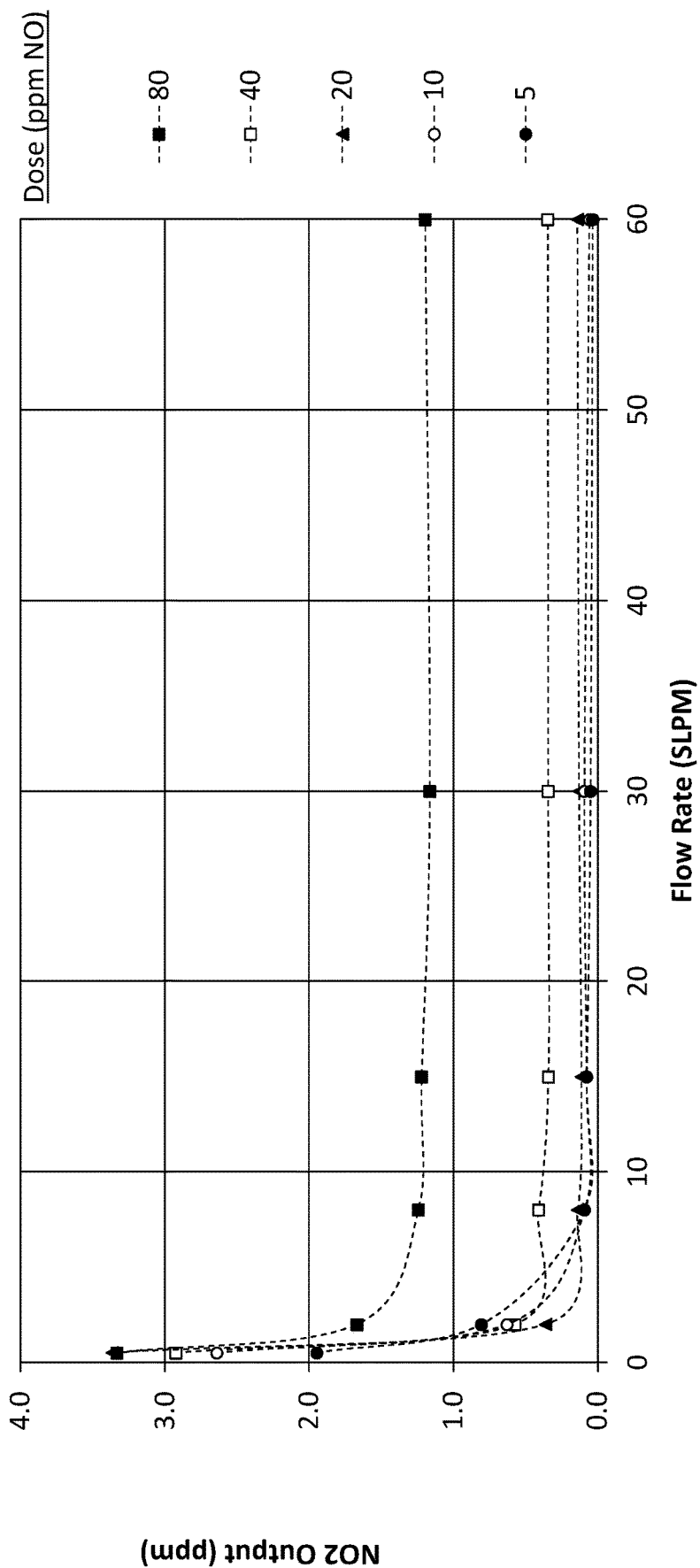
Figure 1E:
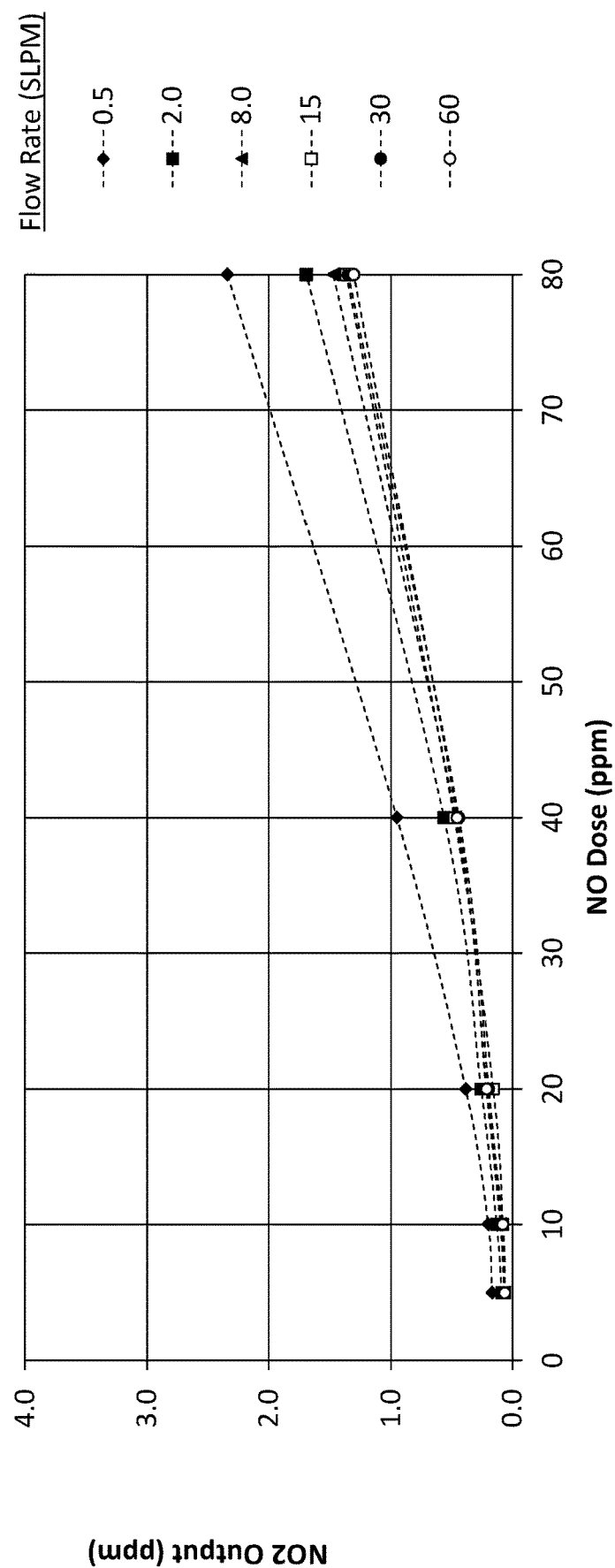
Figure 1F:
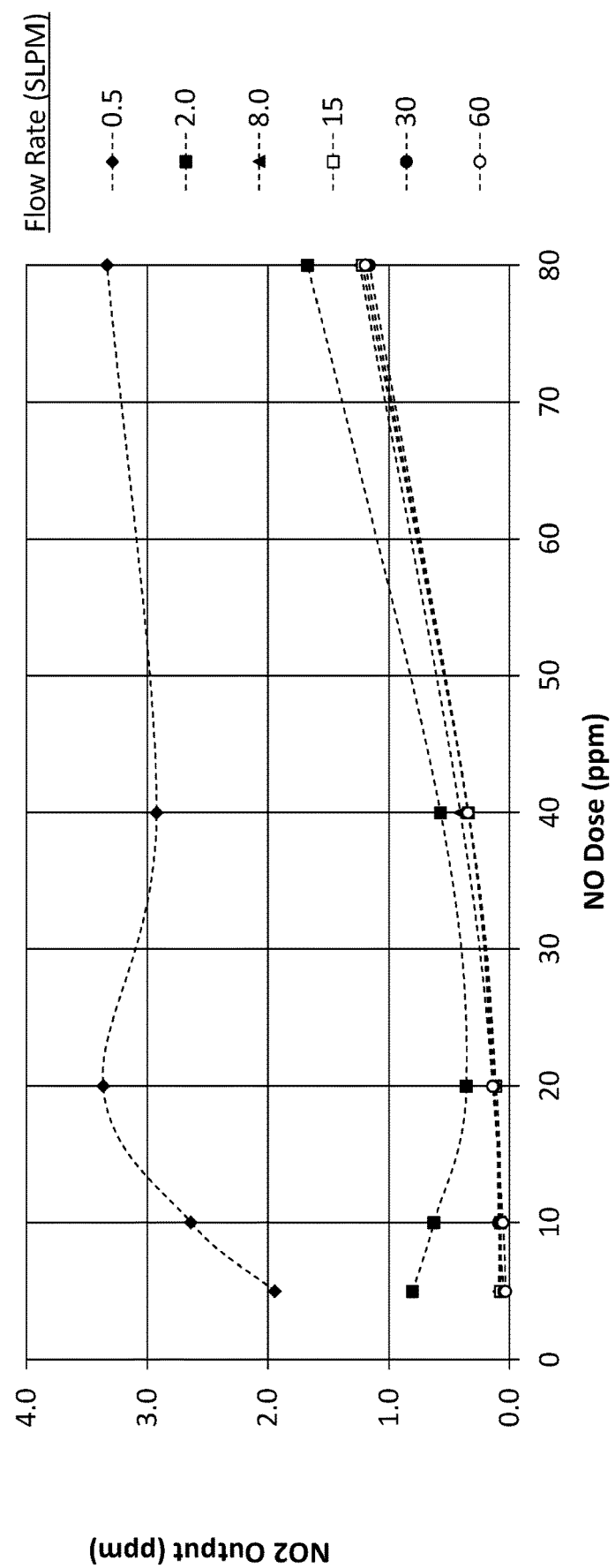

FIGS. 1A and 1B show that the impinging velocity of NO with fresh gas flow in the breathing circuit can substantially impact the amount of NO$_2$ generated. Also, as can be seen by comparing FIG. 1A (low concentration) and FIG. 1B (high concentration), increasing the NO concentration generally increased the amount of NO$_2$ produced.

FIGS. 1C-1F show the respective amounts of NO$_2$ generated for different set NO dosages when the NO is injected into the FGF having different flow rates. As can be seen by comparing FIG. 1C (low concentration) and FIG. 1D (high concentration), increasing the NO concentration generally increased the amount of NO$_2$ produced, particularly at the lower flow rates of FGF. This is also shown by comparing FIG. 1E (low concentration) and FIG. 1F (high concentration), as the NO$_2$ output curve for 0.5 SLPM was drastically different between the low NO source concentration and the high NO source concentration.

Although the above is beneficial in understanding NO$_2$ generation, it substantially complicates minimizing NO$_2$ generation when NO (e.g., from a high concentration NO source) is being injected into the inspiratory limb of the ventilator breathing circuit. For example, the fresh gas flow velocity can vary (e.g., the fresh gas flow rate can vary over the course of the patient breathing cycle, etc.); the NO velocity injected into the fresh gas flow can vary (e.g., the NO flow rate can vary depending on the pressure in the NO delivery line, the dimensions of the NO injection port at the diffusing device, the dimensions of the NO delivery conduit in the NO delivery system, to name a few); and ratio-metric delivery, as may be required for INO therapy, for example, to achieve a constant inspired NO concentration, can require varying the NO delivered in proportion to the fresh gas flow. During the expiratory phase some ventilators use low bias flows (0.5 SLPM) and have slower FGF in a ventilator breathing circuit, which may generate more NO$_2$ than during the inspiratory phase (faster FGF in the ventilator breathing circuit). For example, the data above shows that 10 to 20 times more NO$_2$ may be generated with 4880 ppm NO than with 800 ppm NO at low FGF associated with ventilator exhalation bias flows over the same time period, where insufficient diffusing may occur with a conventional injector module.

Accordingly, in exemplary embodiments, a diffusing device can be designed to minimize NO$_2$ generation by controlling the impinging velocity of the NO and fresh gas flow and the location of injection of the NO into the FGF. In various embodiments, the velocity of the NO flow stream may be high enough relative to the FGF at the location the NO is injected to minimize the NO$_2$ generated. Without being bound by theory, it is thought the NO flow stream may penetrate the FGF stream perpendicularly and with proportional velocities. With very low NO velocity relative to FGF velocity, without being bound by theory, it is believed the NO stays at the outer wall of the FGF stream resulting in poor mixing. Conversely, if only the NO velocity is high and the FGF is not, the mixing time can also be extended resulting in high NO$_2$.

While not wishing to be bound by any particular theory, it is believed that the initial contact diffusion rate of the two mixing gas streams may be primarily controlled by the molecular kinetic energy. In such a gas impingement mixing process, the dissipative exchange from gas momentum can provide direct acting mixing. This rapid diffusion can take place immediately in the vicinity of the nozzle outlet, or directly at the gas impingement point. The molecular kinetic energy is defined as ½ times the molar mass times the square of the velocity, and thus the velocity is inversely proportional to the square root of the molar mass. Equivalent volumes of different gases contain the same number of particles, and the number of moles per liter at a given temperature and pressure is constant. This indicates that the density of gas is directly proportional to its molar mass. Accordingly, this indicates the same mixing energy (i.e. same kinetic energy) would exist at approximately equal velocities or a ratio of 1:1, due to the similar molecular weights of NO, N$_2$, air and O$_2$, which all range from 28 to 32 grams per mole. However, given the slight molecular weight imbalance between air/O$_2$ mixtures and NO/N$_2$ mixtures, the greatest diffusion from the dissipative energy exchange can be at velocity ratios less than 1:1 (FGF:NO), such as 0.85:1, 0.9:1 or 0.95:1, depending on the relative proportions of N$_2$, NO, O$_2$ and air.

In various embodiments, the velocity of the two gas streams may be proportional to each other in order to minimize the NO$_2$ generated. The NO velocity can be controlled by changing the dimensions of the NO injection port, for example, as other factors (e.g., pressure in the NO delivery line, dimensions of the NO injection channel, etc.) may be fixed. It will be appreciated that any means for controlling the NO velocity can be used. However, controlling the fresh gas flow velocity can be substantially challenging as the velocity of the fresh gas flow is typically controlled by the ventilator. Further, as noted above, the velocity of the fresh gas flow during the expiratory phase can be substantially slow. In at least some instances, the impinging velocity of the fresh gas flow during at least the expiratory phase can be too slow to minimize NO$_2$ generation. Accordingly, in exemplary embodiments, the diffusing device can include at least one accelerator capable of accelerating the fresh gas flow to a desired impinging velocity, for example, that may be directed to a point of intersection with the NO-containing gas.

In one or more embodiments, the orifice diameter at the NO gas impingement point to the fresh gas flow tube can be sized appropriately to maintain a fixed aspect ratio outlet area between the diffusing module 100 tube diameter (i.e. the FGF tube diameter) to the NO nozzle outlet diameter area (i.e. the injection port orifice diameter). This ratio in tube outlet area can be proportional to the NO cylinder concentration over the NO set dose. For example, for an 800 ppm cylinder concentration at a set dose of 20 ppm, a 40 to 1 turn down ratio exists in NO flow rate. In order to maintain a 1:1 impinging gas velocity relationship, an injector module flow tube area to injection nozzle outlet area may be sized at 40:1 at the lowest expected fresh gas flow rate (e.g., 0.5 SLPM). As another example, for a 4880 ppm cylinder concentration at a set dose of 10 ppm, a 488 to 1 turn down ratio exists in NO flow rate. In order to maintain a 1:1 impinging gas velocity relationship, an injector module tube area to injection nozzle outlet area may be sized at 488:1

In one or more embodiments, the dimensions of the injection channel and injection port may be adjusted so the ratio of NO velocity to FGF velocity is less than about 2:1, such as about 1.5:1, 1:1, 0.95:1, 0.9:1, 0.85:1, 0.8:1, 0.7:1, 0.6:0.5:1, 0.4:1, 0.3:1, 0.2:1, 0.1:1 or 0.05:1.

In exemplary embodiments, at least one accelerator can be any device or component capable of accelerating all or a portion of the fresh gas flow. For example, the accelerator can be a conical structure with a tapered surface, a tapered section, bi-directional conical structure, and/or any shapes or surfaces capable of accelerating fresh gas flow. Other examples include structures with surfaces similar to a wing, as gas flowing over the top of a wing (curved surface) has a faster velocity than the gas flowing underneath the bottom of the wing (relatively flat surface). These accelerator structures are only exemplary, and other structures capable of accelerating at least some portion of a gas flow are also within the scope of this invention.

Figure 1G:
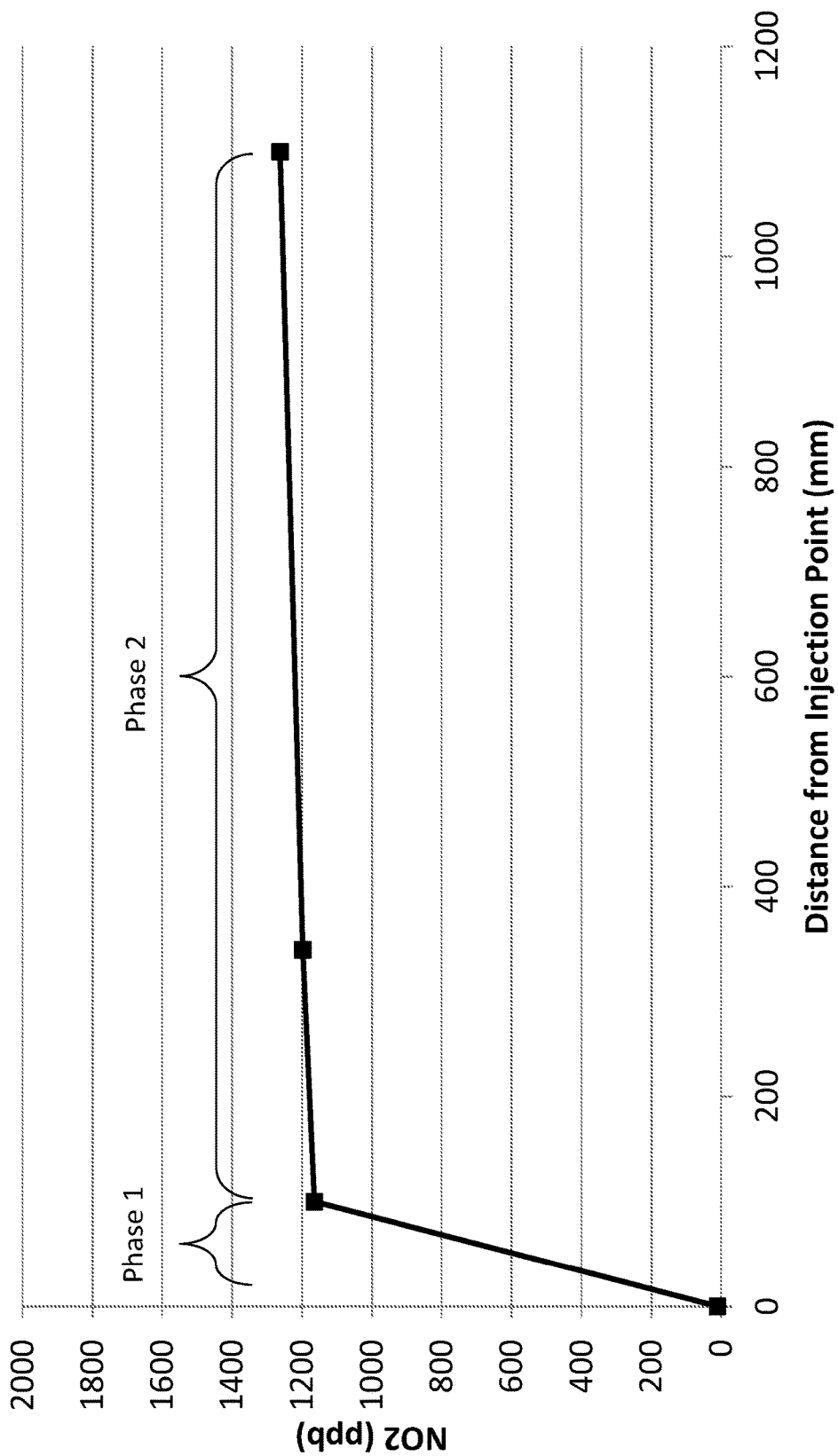
FIG. 1G shows the $NO_2$ generated at various points downstream from the point of NO injection.

Notably, when injecting NO into fresh gas flow, the device's configuration and dimensions may be adjusted to reduce the source NO concentration as quickly as possible. In various embodiments, mixing features may be added to the device downstream of the NO injection point. In various embodiments, mixing can be thought of in 2 phases. The first phase where the majority of $NO_2$ may be generated is the time from NO injection to when the NO concentration reaches the set dose (e.g., a homogeneous state equal to the set dose). The second phase of $NO_2$ generation is due to the residence time in the inspiratory limb at set dose. A majority of $NO_2$ may be generated at, or near, the first point of contact between the NO and fresh gas flow (e.g., $O_2$). These two phases of NO generation can be seen in FIG. 1G, which shows the $NO_2$ concentration at various points downstream from the point of injection. As can be seen from FIG. 1G, the majority of the $NO_2$ is generated soon after the NO is injected (Phase 1), with only a small portion of the $NO_2$ being generated after the initial injection and mixing of the NO (Phase 2). This majority of the $NO_2$ being generated during the first phase follows the above $NO_2$ generation kinetics as the first phase of NO injection the local NO concentration is highest (e.g., as the NO has not yet diffused into the fresh gas flow to provide the homogenous set NO dose). By way of example, when injecting 5000 ppm NO into the breathing circuit, at the point of injection the NO concentration is highest (e.g., approximately 5000 ppm NO) as the NO has not yet diffused with the fresh gas flow. After this point of injection, the injected NO and the fresh gas flow diffuse together causing the NO concentration to decrease to a lower concentration (e.g., from 5000 ppm NO to a desired dose of 20 ppm NO).

Figure 2A:
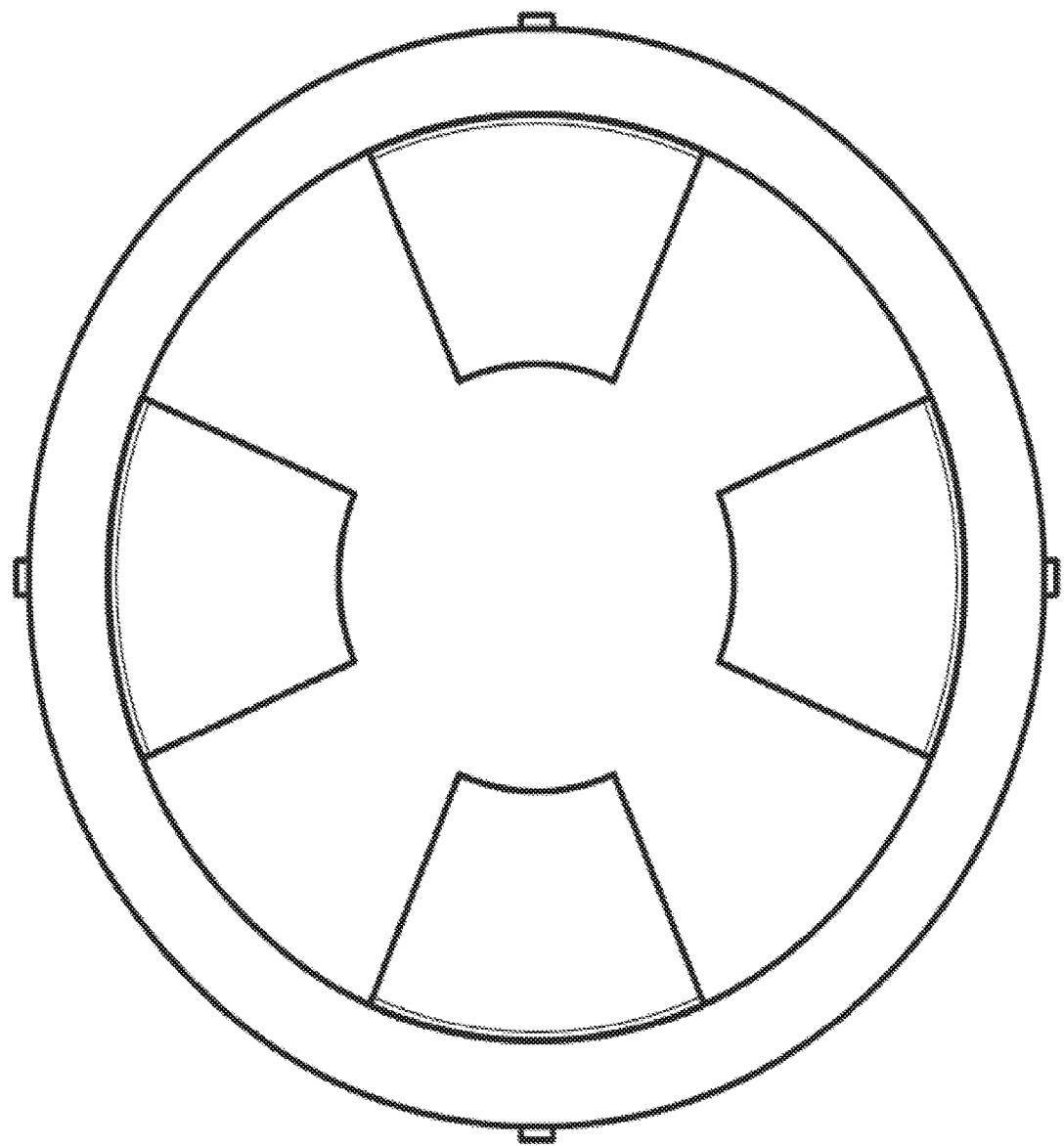
FIGS. 2A-C illustrate an exemplary embodiment of a mixing device having a plurality of blades.
Figure 2B:
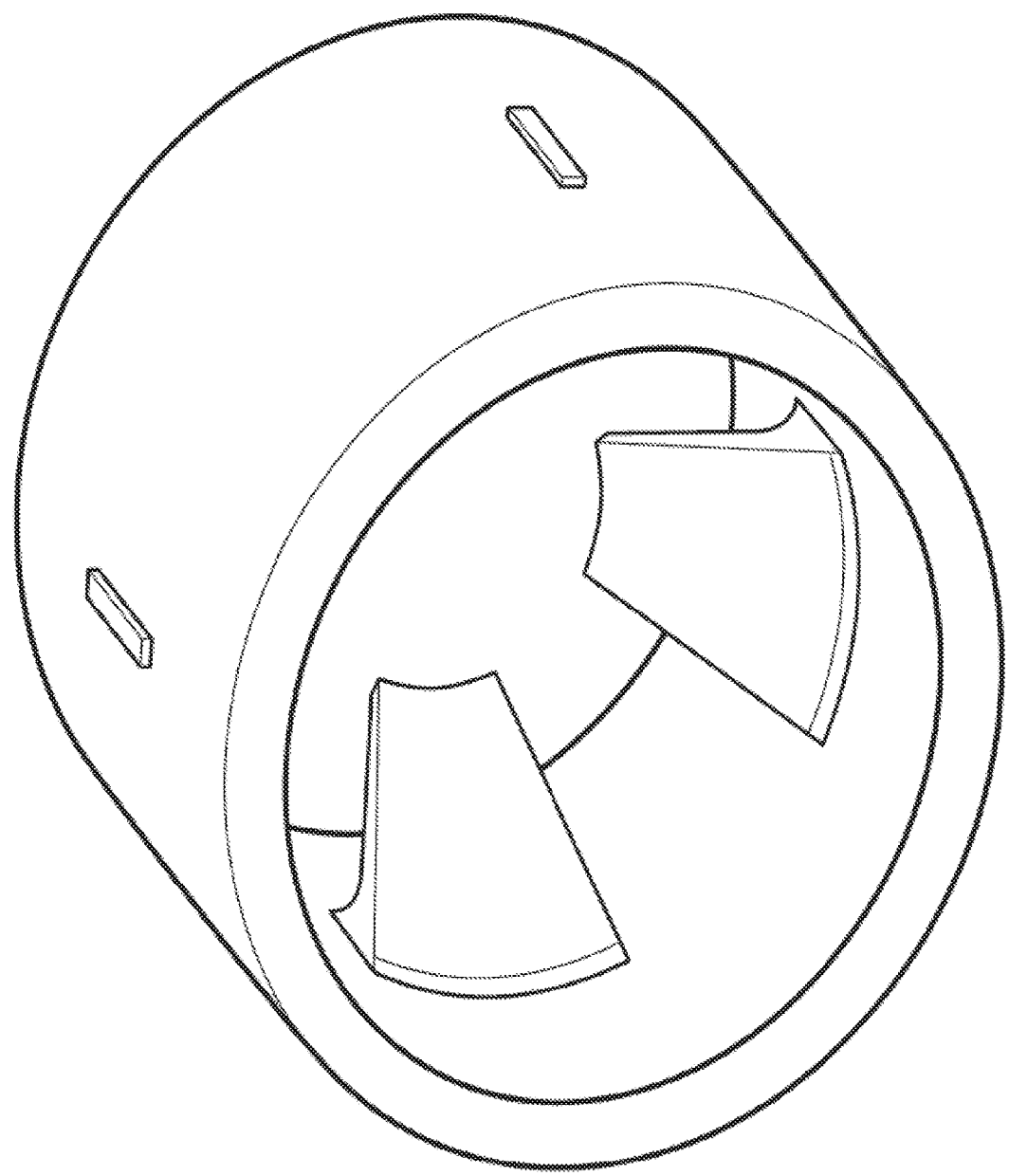
Figure 2C:
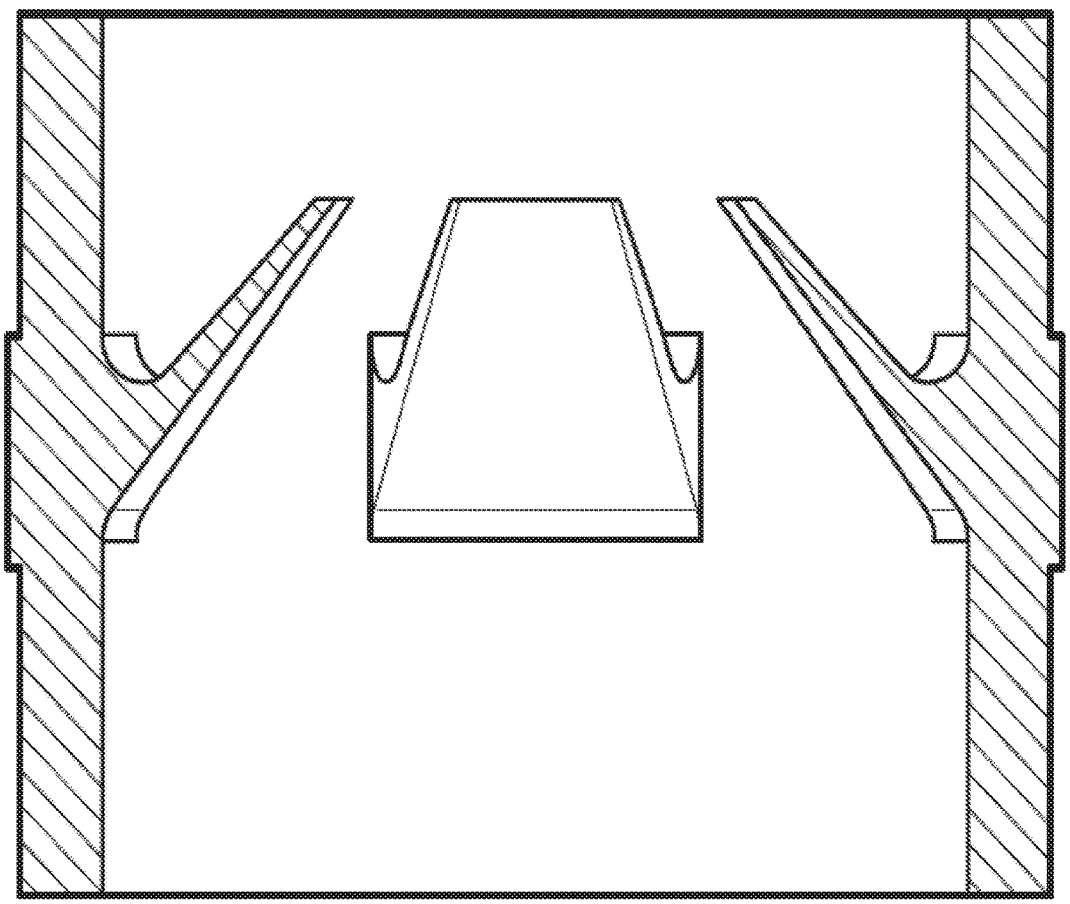
Figure 3A:
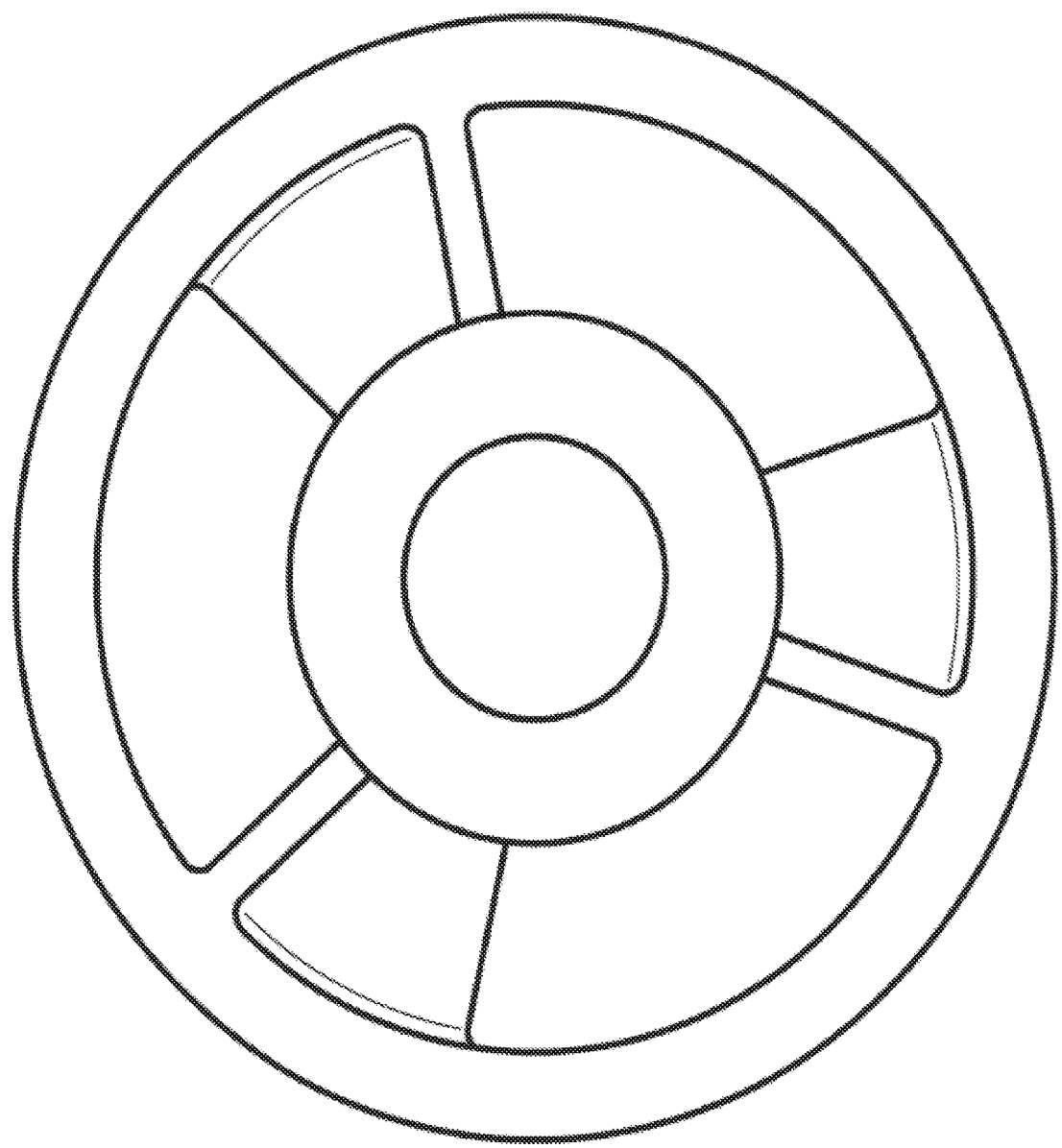
FIGS. 3A-C illustrate an exemplary embodiment of a tapered section having a plurality of angled fins.
Figure 3B:
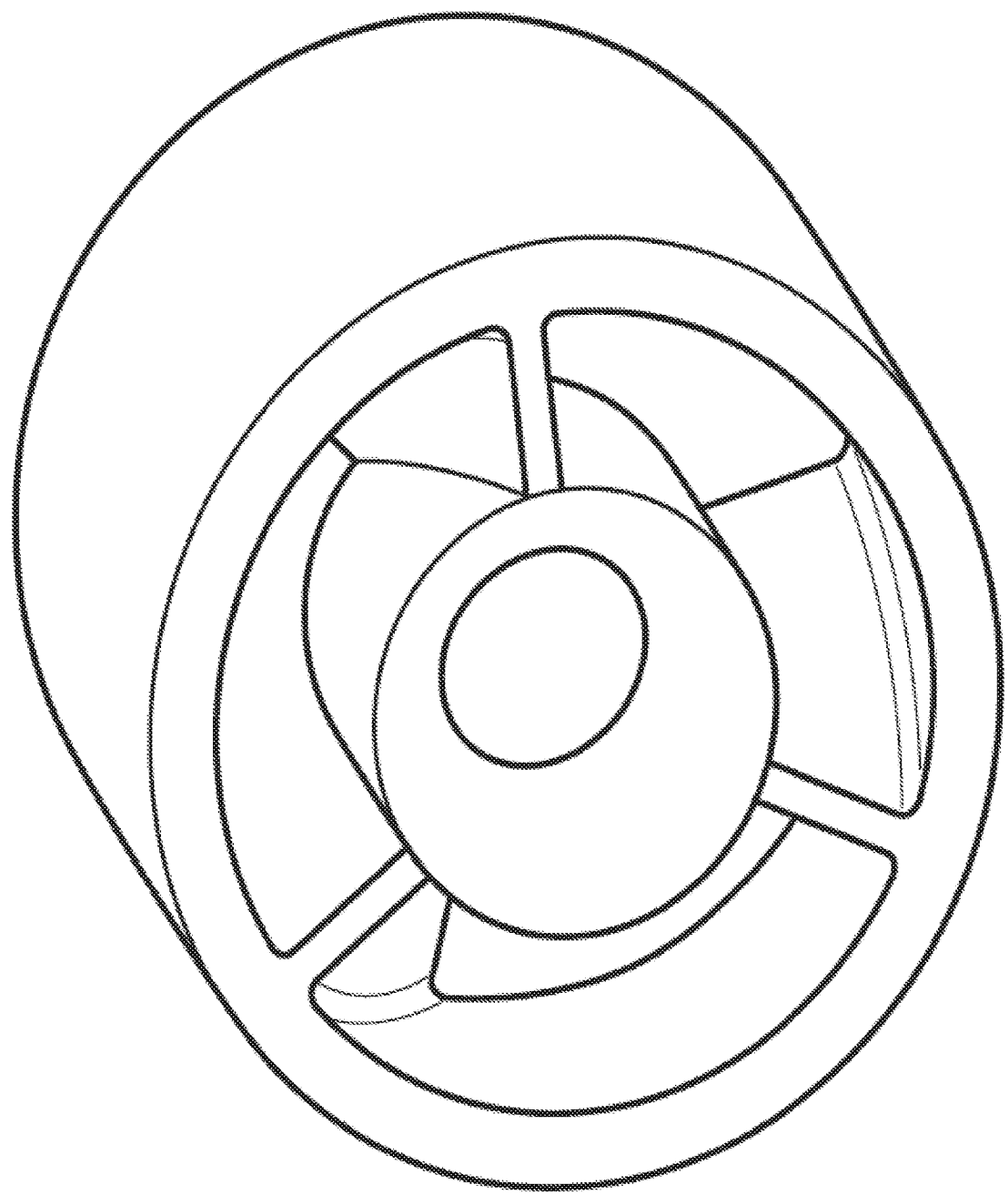
Figure 3C:
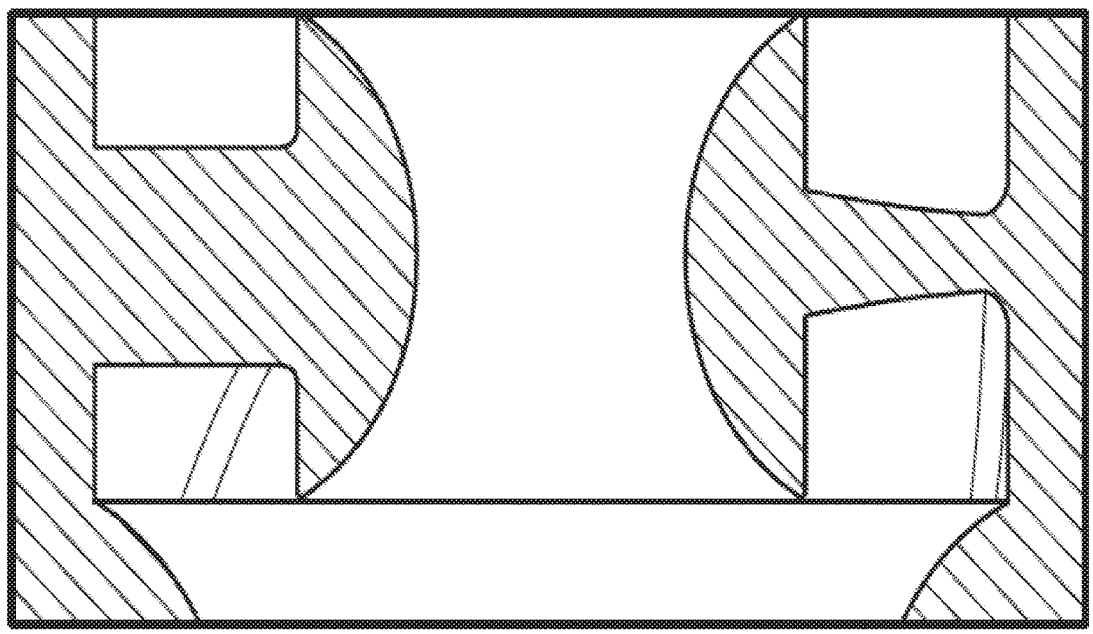
Figure 4A:
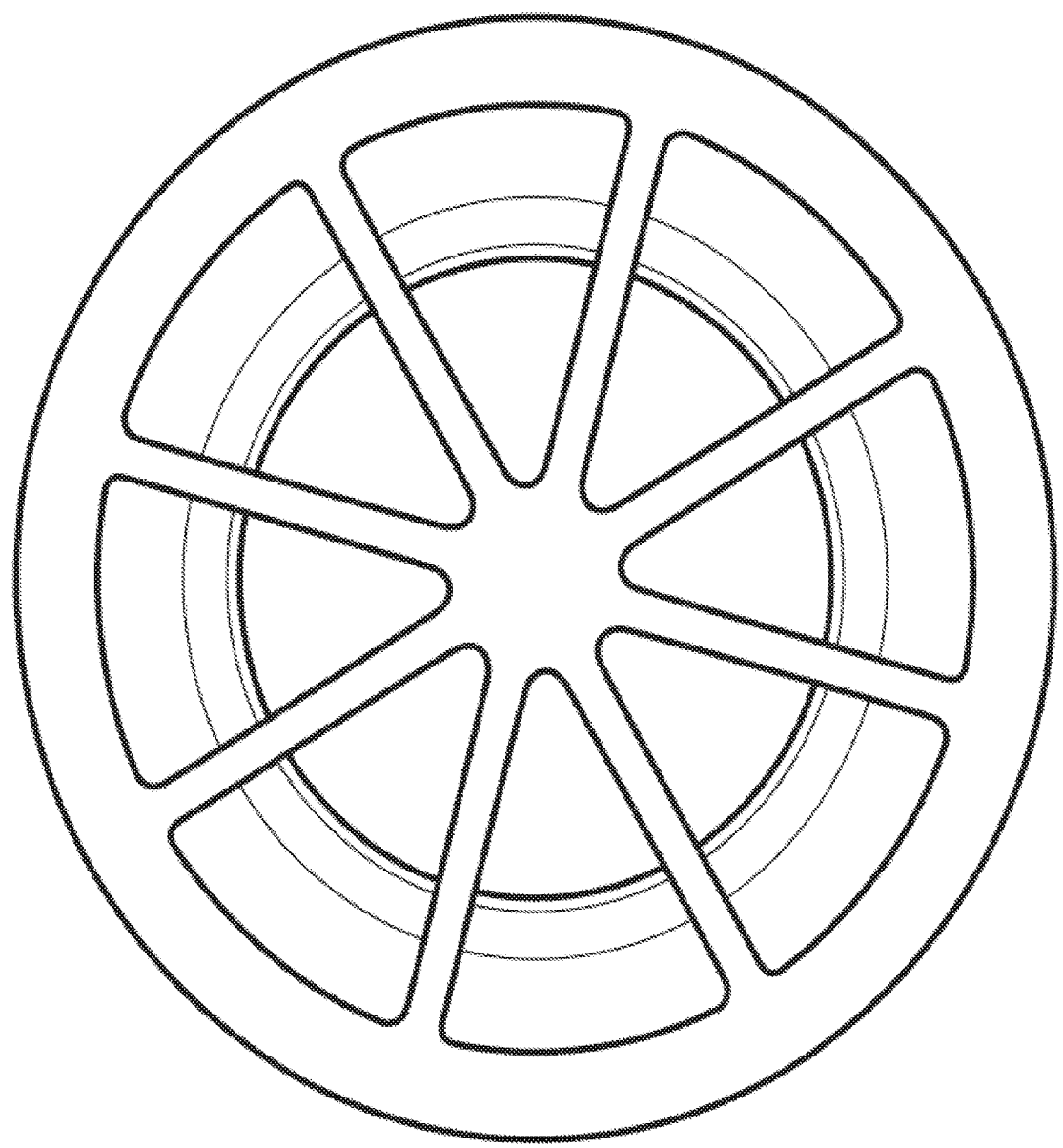
FIGS. 4A-C illustrate an exemplary embodiment of a mixing device having a plurality of plates.
Figure 4B:
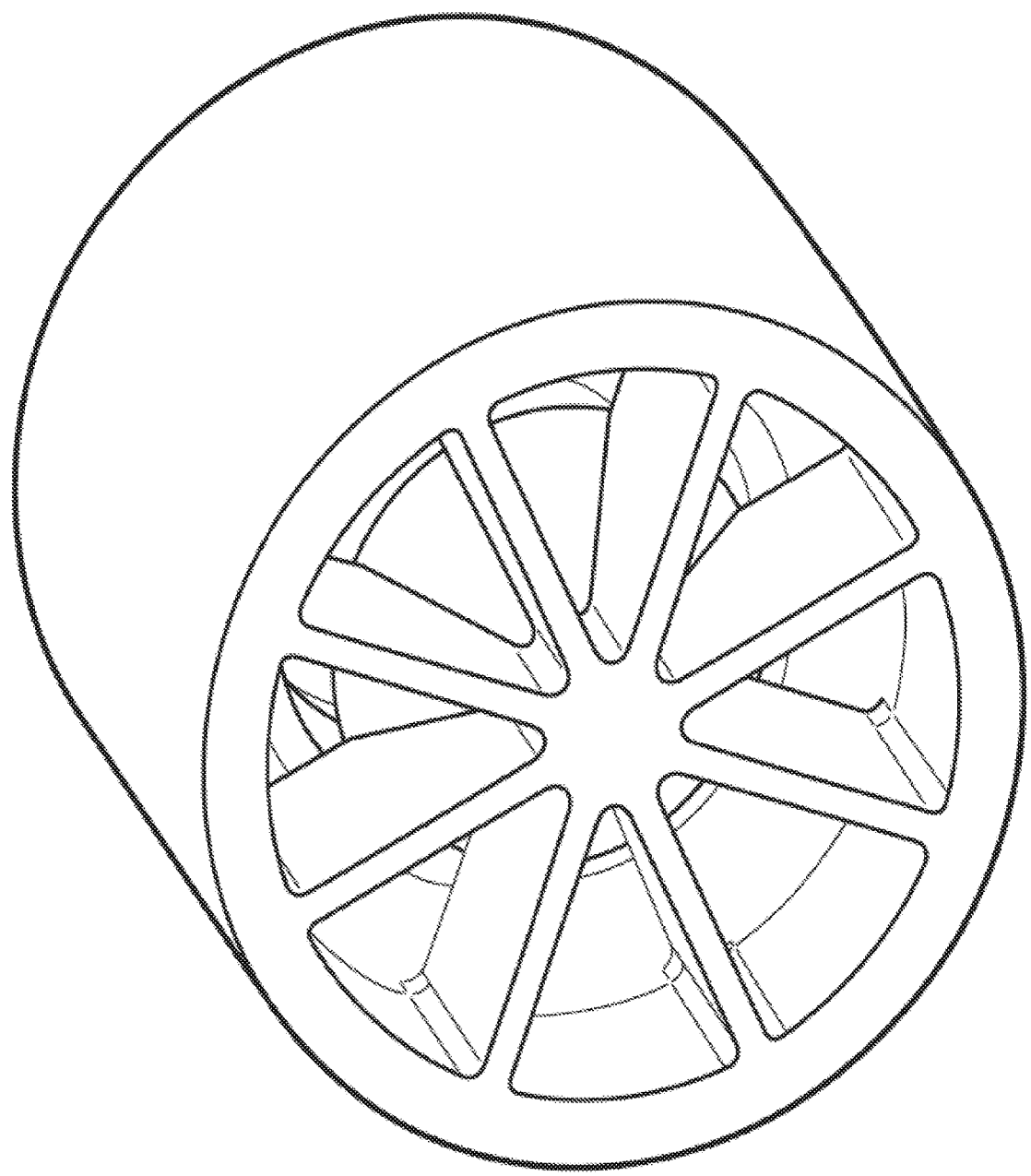
Figure 4C:
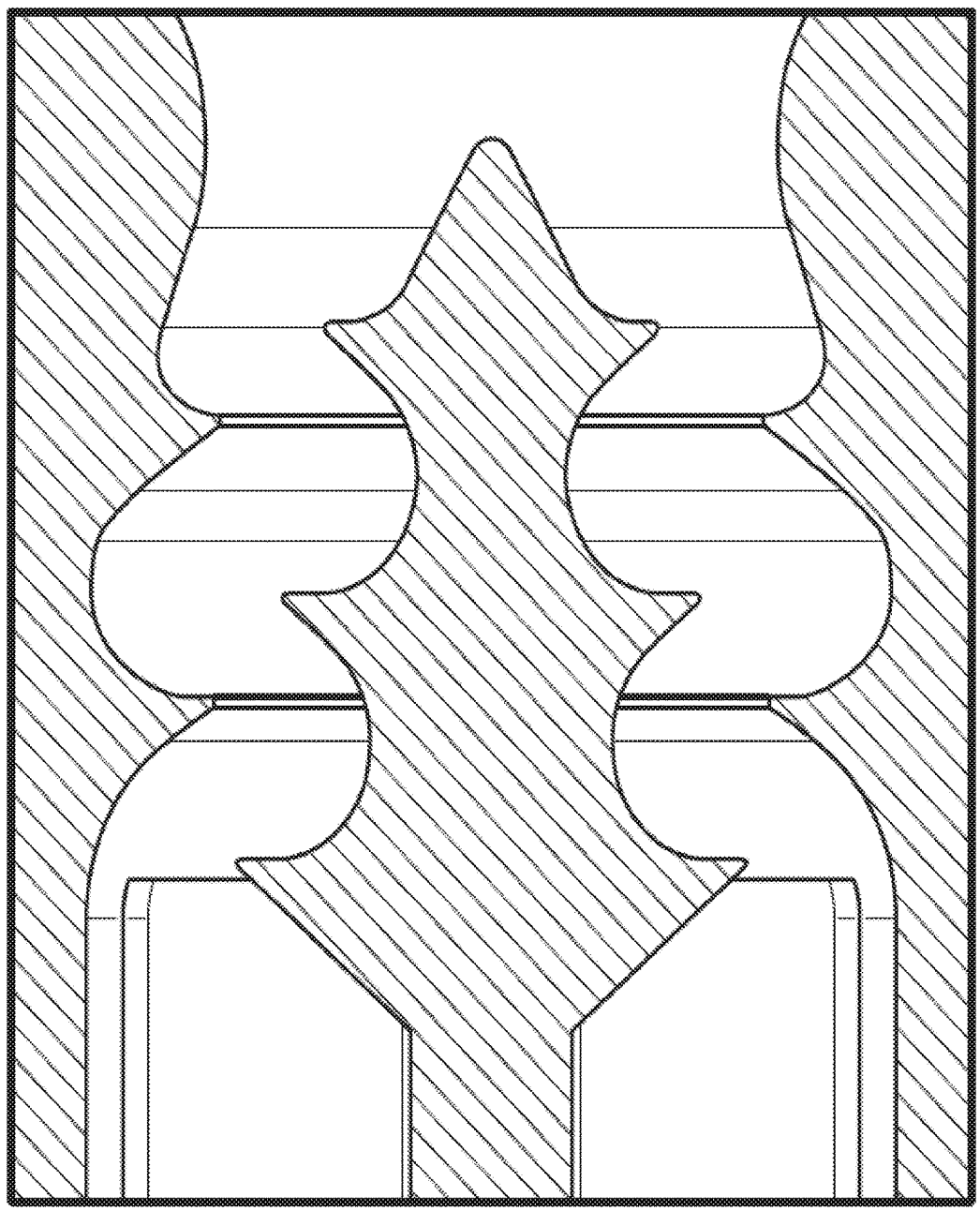
Figure 5A:
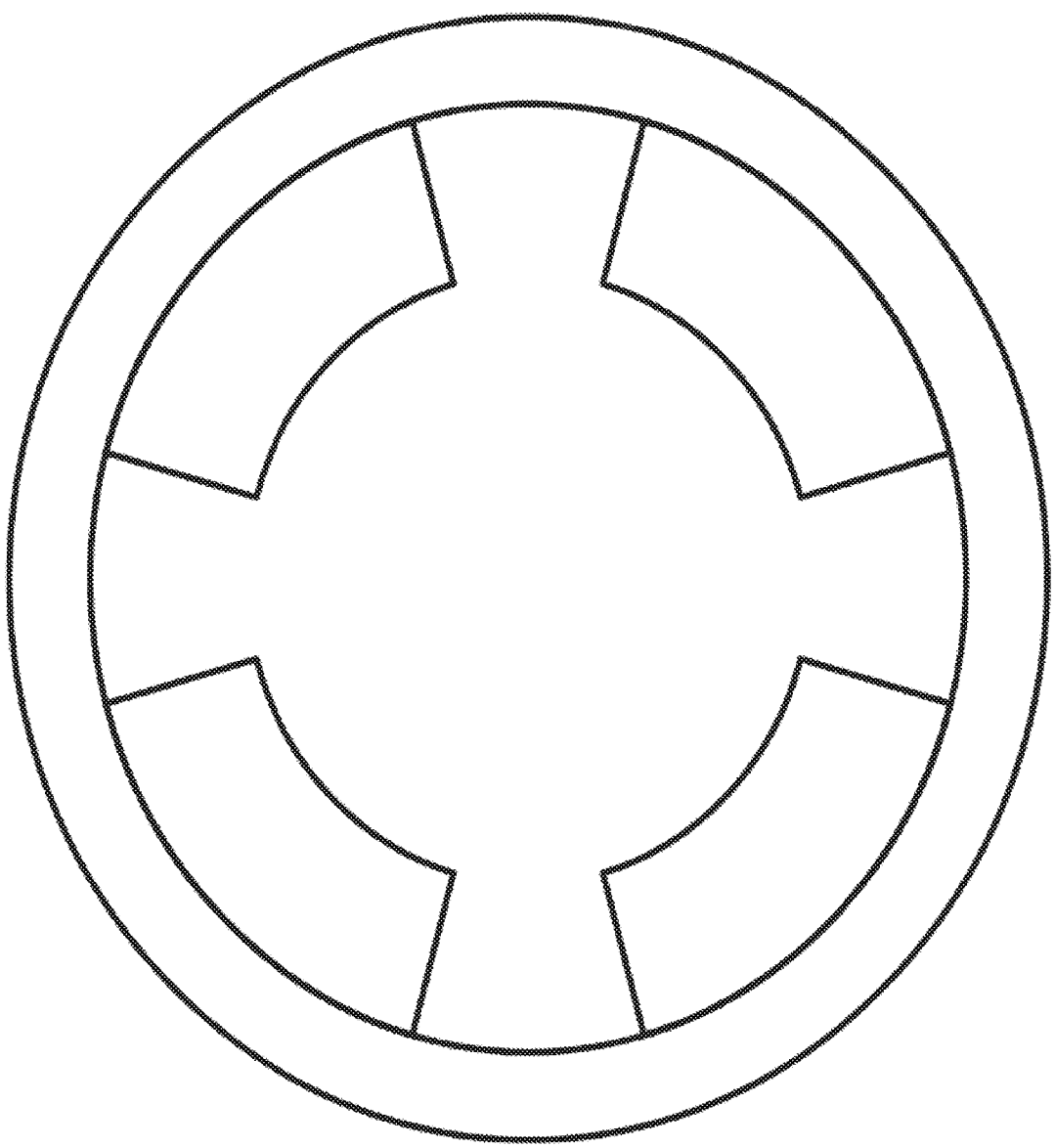
FIGS. 5A-C illustrate an exemplary embodiment of a mixing device having a plurality of curved blades.
Figure 5B:
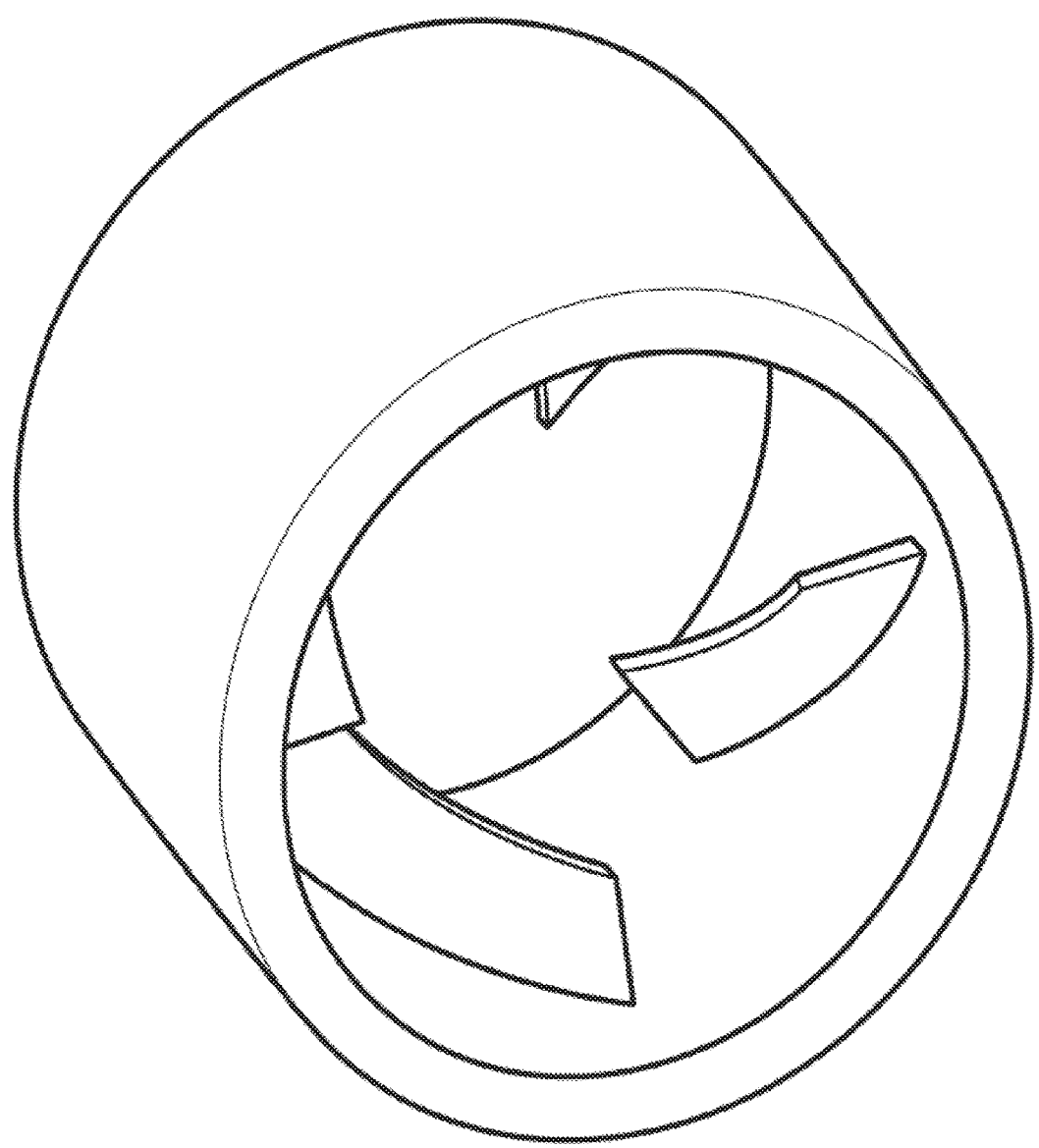
Figure 5C:
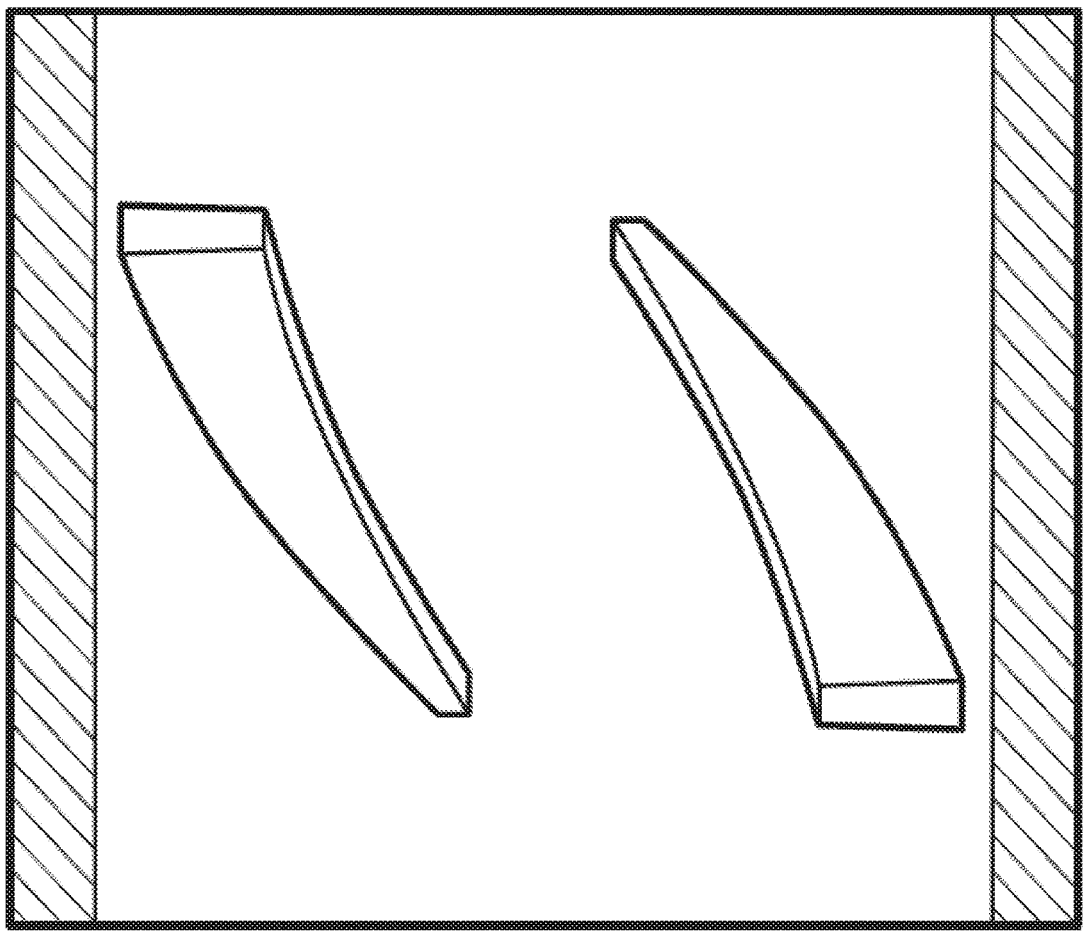
Figure 6A:
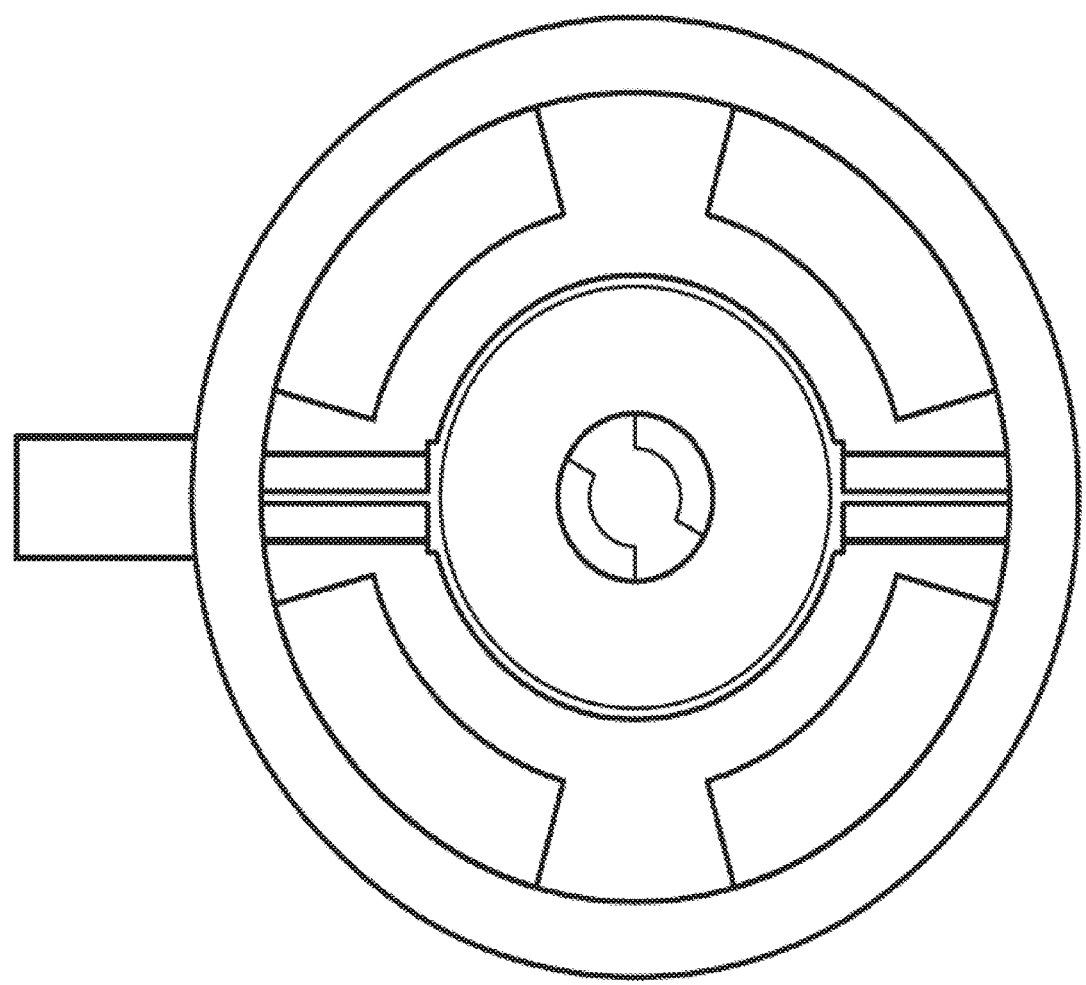
FIGS. 6A-C illustrate an exemplary embodiment of a mixing device having a plurality of curved blades and an injection channel at a tapered section.
Figure 6B:
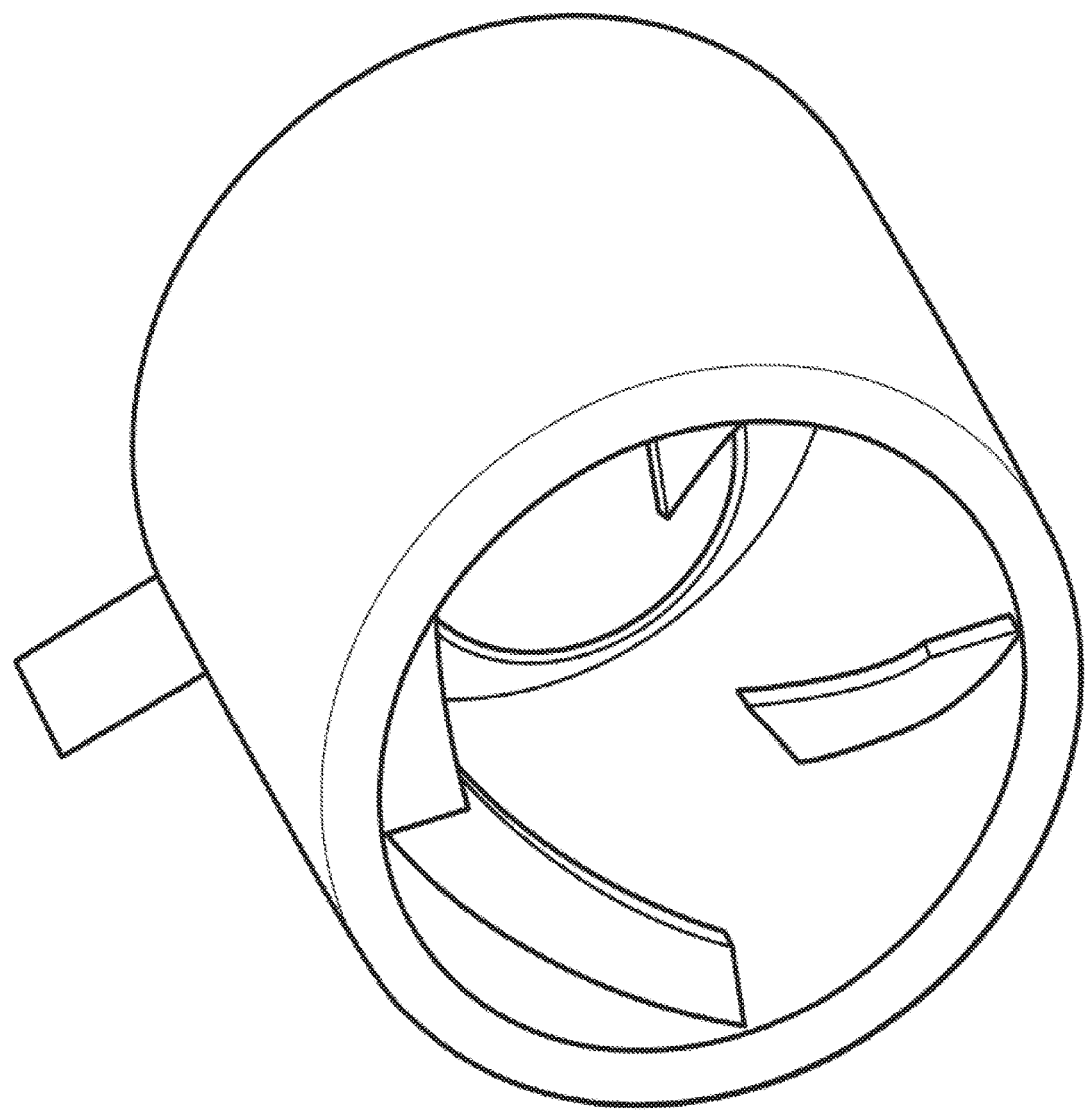
Figure 6C:
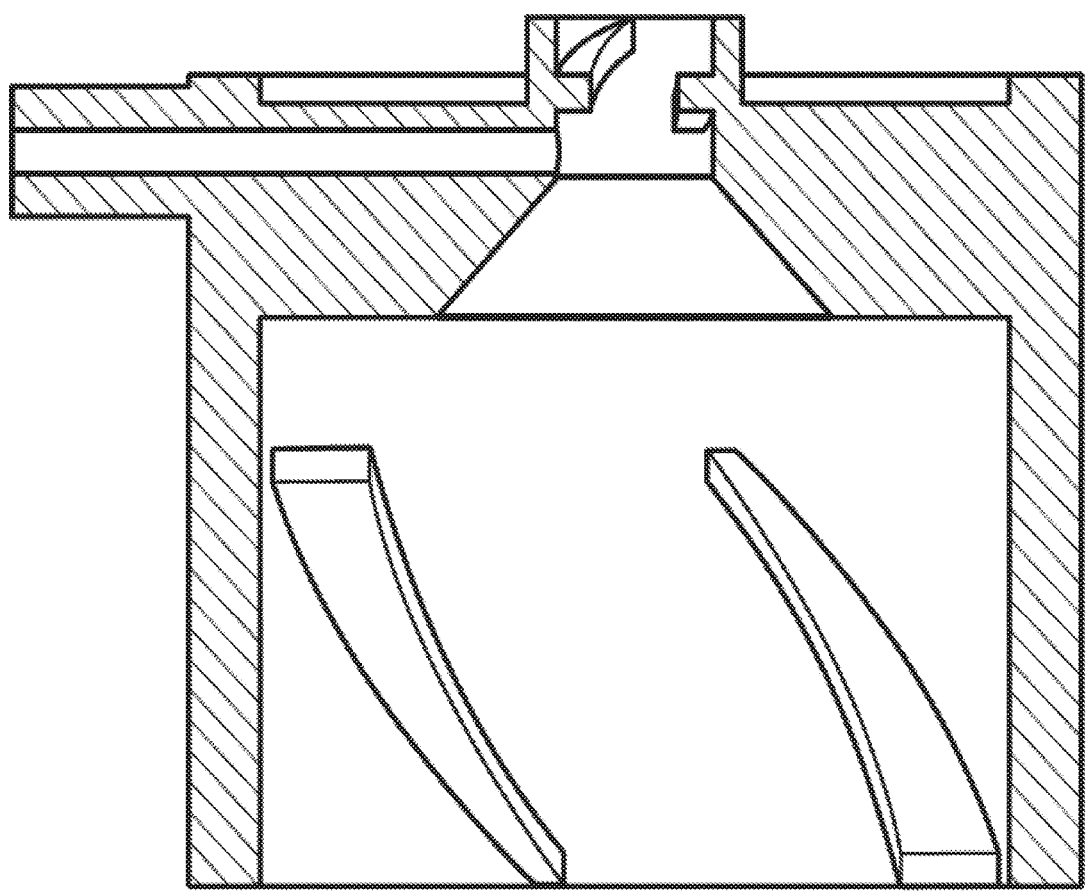

Accordingly, one approach for rapidly mixing the NO and FGF is the use of a mixing device placed immediately downstream or close to the point of NO injection to ensure that the combined gas stream has a homogenous NO concentration as soon as possible. For example, a plurality of blades, plates and/or fins can be placed downstream of the NO injection point to ensure prompt mixing of the two gas streams. 1, 2, 3, 4, 5, 6, 7, 8, 9, 10, 11, 12, 13, 14, 15 or more blades, plates and/or fins can be used. FIGS. 2A-C provide various views of an exemplary configuration of a mixing device having four blades. FIGS. 3A-C provide various views of an exemplary configuration of a mixing device having three angled fins. FIGS. 4A-C provide various views of an exemplary configuration of a mixing device having eight plates. FIGS. 5A-C provide various views of an exemplary configuration of a mixing device having four curved blades. FIGS. 6A-C provide various views of an exemplary configuration of a mixing device having four curved blades and an injection channel at a tapered section.

When a plurality of blades, plates and/or fins are used in a mixing device, the blades, plates and/or fins can be placed in parallel at the same distance downstream from the NO injection point and/or may be placed in series at various distances downstream from the NO injection point. For example, each blade, plate or fin may be placed 1, 2, 3, 4, 5, 6, 7, 8, 9, 10, 15, 20, 25, 30, 35, 40, 50, 60, 70, 80, 90 or 100 cm downstream from the NO injection point.

The presence of a mixing device can also be used to shorten the distance between the NO injection point and one or more sampling points for monitoring the composition of the combined gas, such as the $O_2$, NO and $NO_2$ concentrations. For example, the first sampling point can be located 1, 2, 3, 4, 5, 6, 7, 8, 9, 10, 15, 20, 25, 30, 35, 40, 50, 60, 70, 80, 90 or 100 cm downstream from mixing device. Furthermore, a plurality of sampling points may be used, such as sampling points located at various distances from the NO injection point. 1, 2, 3, 4, 5, 6, 7, 8, 9, 10, 15, 20, 25, 30 or more sampling points may be used. The distance between sampling points can be 1, 2, 3, 4, 5, 6, 7, 8, 9, 10, 15, 20, 25 or 30 cm. The plurality of sampling points can be used to separately analyze the combined gas stream as a function of length down the breathing circuit, or two or more sampling can be combined to provide an average for the composition of the gas.

Furthermore, the location of the point of injection of NO into the fresh gas flow can influence the reduction in $NO_2$ generation. In exemplary embodiments, the NO injection point can be located where the residence time of the initial high concentration is minimized and/or initial high concentration NO is rapidly dispersed. For example the point of injection of NO (e.g., high concentration NO, 5000 ppm NO) may be located at the center of the annular body or as part of the tapered section, to reduce the amount of time that the NO remains at the initial high concentration. Accordingly, the point of NO injection can be located where the NO will be intermixed quickly with the fresh gas flow thereby minimizing the residence time of the high concentration NO and in turn reducing the $NO_2$ generated. While not wishing to be bound by any particular theory, it is believed that injecting the NO at a point in which the fresh gas flow has a high velocity will generate less $NO_2$ than other traditional techniques of injecting NO at the edge (i.e. wall) of the tube where fresh gas flow will have a low velocity.

Figure 7:
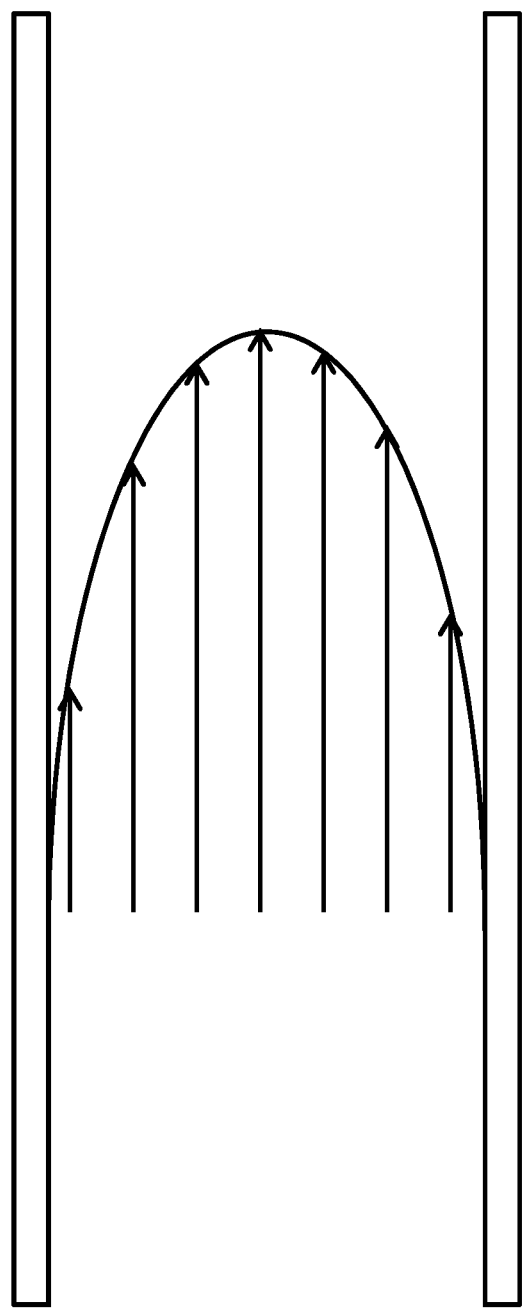
FIG. 7 illustrates an exemplary velocity distribution of a gas flow within a tube.

FIG. 7 illustrates an exemplary velocity distribution of a gas flow through a tube. As can be seen from FIG. 7, the gas flow has the lowest velocity closest to the edge boundary (e.g. wall of the tube) and has the highest velocity farthest from the edge boundary. Accordingly, in some embodiments the NO is injected at a distance from the edge boundary where the gas velocity is higher than the gas velocity at or close to the edge boundary.

In exemplary embodiments, to reduce $NO_2$ generation, the point of injection of NO into fresh gas flow can be located where the fresh gas flow is accelerated to the desired velocity. The accelerator may act to increase the fresh gas flow velocity from an inlet end to the outlet end, and the injection port located a distance from the inlet at which the fresh gas flow has increased to an intended velocity. The increase in velocity may be created by conversion of the gas's potential energy to kinetic energy. By way of example, the velocity may be increased by the reducing cross section of the tapered section, as the gas flows from a region of higher pressure to a region of lower pressure. The gas velocity being proportional to the change in cross-sectional area and change in gas density. Of course other techniques for increasing the velocity are envisioned.

Further complicating any potential solutions for minimizing $NO_2$ generation when injecting NO into the ventilator breathing circuit, ventilators require that any element (e.g., injector module, $NO_2$ minimization device, etc.) used with the ventilator breathing circuit not cause a substantial change to the ventilator inspiratory flow profile (by way of increased resistance to flow or increased compressible volume). Generally speaking, the allowable pressure drop across the entire breathing circuit can be 6 cm $H_2O$ at 30 SLPM for adults, 6 cm $H_2O$ at 15 SLPM for pediatrics and 6 cm $H_2O$ at 2.5 SLPM for neonates inclusive of ventilator outlet resistance. In light of this, the allowable pressure drop across the diffuser should be minimized. For example, current INOmax DS Injector Module is rated at 1.5 cm $H_2O$ at 60 SLPM. Accordingly, systems and methods of the present invention minimize $NO_2$ without affecting ventilator performance and/or causing substantial pressure drops, flow profile changes, and introducing substantial compressible volumes, for example, that may affect patient ventilation gas exchange.

Accordingly, in exemplary embodiments, the diffusing device can be configured and dimensioned so that at least the accelerator increase the fresh gas flow impinging velocity at the lowest expected fresh gas flow rate while not causing a substantial pressure drop in the highest peak fresh gas flow, not cause substantial changes to the inspiratory fresh gas flow's flow profile, and not create a substantial compressible volume in the breathing circuit. For example, the mouth and throat diameter may be selected to increase FGF velocity while minimizing delay in pressure changes and gas flow to a patient. To minimize changes to pressure, flow, and compressible volume the diffusing device can include a region for fresh gas flow to bypass the accelerator. For example, the diffuser can include a bypass gap which may be located about the periphery of the diffuser and/or accelerator.

After using the techniques disclosed herein to minimize $NO_2$ generation in the first phase (e.g., rapidly diffusing the NO and fresh gas flow at the point of injection, etc.), the NO may continue to traverse the remaining region of the breathing circuit at, or very close to, the desired set dose (e.g., 1 to 80 ppm NO). As this NO dose, or very close to the desired set dose, traverses the remaining region of the breathing circuit $NO_2$ may be generated (second phase); however, as described above, using the techniques disclosed herein, the majority of $NO_2$ that would have been produced will be substantially minimized thereby substantially reducing the total amount of $NO_2$ generated (e.g., immediate $NO_2$ generated and latent $NO_2$ generation).

To further mitigate $NO_2$ generation, NO may be introduced (e.g., in the ventilator breathing circuit) as close to the patient as technically feasible to reduce the contact time by reducing the time the NO and $O_2$ are in transit together, thus partly reducing $NO_2$ formation. $NO_2$ conversion time is the elapsed time NO and oxygen resides in combination prior to reaching the patient. $NO_2$ conversion time is therefore a function of ventilator flow rates (inspiratory and expiratory), ventilator I:E ratio, and breathing circuit volume from the point of NO injection to the patient airway end.

However, as explained above, in exemplary embodiments the downstream $NO_2$ generation (i.e. Phase 2) is much less than the $NO_2$ generation upon injection (Phase 1). Accordingly, in some embodiments the NO-containing gas is injected at a position that is significantly upstream from the patient, such as several feet from the patient, yet the $NO_2$ can be at an acceptable level (e.g. less than 1 ppm). Exemplary NO injection points include those at least 1, 2, 3, 4, 5, 6, 7, 8, 9 or 10 feet upstream from the patient. Such locations can be upstream of a patient "Y" piece, upstream of a humidifier, upstream of a nebulizer or other locations upstream from the patient in the ventilator breathing circuit.

In various embodiments, the second gas stream may be injected at an angle in the range of about 60° to about 120°, or at an angle in the range of about 75° to about 105°, or about 80° to about 100°, or about 85° to about 95°, or at about 90° to the axis of the first gas stream.

An aspect of the present invention relates to an injection device for injecting a high concentration gas into a transverse gas stream.

In one or more embodiments, the device comprises an injection port that injects the second gas stream perpendicularly into the first gas stream.

In various embodiments, a high concentration NO-containing gas may be in the range of greater than 800 ppm NO to about 5000 ppm NO, or about 2000 ppm NO to about 4880 ppm NO, or at about 4880 ppm NO. Exemplary lower limits include about 800 ppm, about 1,000 ppm, about 1,200 ppm, about 1,400 ppm, about 1,600 ppm, about 1,800 ppm, about 2,000 ppm, about 2,200 ppm, about 2,400 ppm, about 2,600 ppm, about 2,800 ppm, about 3,000 ppm, about 3,200 ppm, about 3,400 ppm, about 3,600 ppm, about 3,800 ppm, about 4,000 ppm, about 4,200 ppm, about 4,400 ppm, about 4,600 ppm, and about 4,800 ppm. Exemplary upper limits include about 10,000 pm, about 9,000 ppm, about 8,000 ppm, about 7,000 ppm, about 6,500 ppm, about 6,000 ppm, about 5,500 ppm, about 5,200 ppm, about 5,000 ppm and about 4,900 ppm. The high concentration NO-containing gas may be contained in a pressurized cylinder at a pressure in the range of about 200 psig and about 3000 psig, or in the range of about 2000 psig and about 2400 psig, or about 2200 psig and about 2400 psig. Of course other sources of high concentration NO are envisioned.

FIGS. 8A-B illustrate an exemplary device for diffusing a high concentration low volume gas flow and a high volume gas flow using the techniques disclosed above.

In one or more embodiments, the diffusing device 100 comprises a body 110 that may be an annular body formed by a cylinder having a wall 115 and a hollow (also referred to as open), internal region 118. The body 110 may be configured and dimensioned to connect to tubing in a ventilator breathing circuit (e.g., 10, 15 and 22 mm), fit into ventilator tubing, or have ventilator tubing fitted into the body. In various embodiments, the inlet end of the device comprises a male connection configured and dimensioned to join to a ventilator tube, and the outlet end comprises a female connection configured and dimensioned to join to a ventilator tube or humidifier chamber inlet. In a non-limiting example, the inlet end of the device comprises a 22 mm (O.D.) male connection, and the outlet end comprises a 22 mm (I.D.) female connection. In addition, in various embodiments the diffusing device 100 can be a component or part of an injector module which couples to a ventilator breathing circuit or component such as humidifier chamber, as is known in the art.

In one or more embodiments, the diffusing device 100 comprises a body 110 that may be rectangular, cubic or other geometric shapes that are configured and dimensioned to connect to tubing in a ventilator breathing circuit (e.g., 10, 15 and 22 mm), and having a hollow internal region. For convenience, in embodiments where the body comprises a cylindrical wall, the body is referred to as an annular body in the specification.

In one or more embodiments, an annular body 110 may have an outside diameter 'A' at an inlet end and/or an outlet end. The outside diameter 'A' may be in the range of about 10 mm (0.394 in.) to about 25 mm (1.0 in.), or about 22 mm (0.866 in.), where the ventilator tubing may be fitted around the outside of the inlet end OD and inside the outlet end ID. In various embodiments, a ventilator tube may be connected to an inlet end and/or outlet end of a diffusing device utilizing a friction-fit connection, as would be known in the art. In various embodiments, the OD at the inlet end may be the same or different from the OD of the outlet end.

In one or more embodiments, the annular body may have an inside diameter 'B' at an outlet end and/or an inlet end. The inside diameter 'B' may be in the range of about 10 mm (0.394 in.) to about 25 mm (1.0 in.), or about 22 mm (0.866 in.), where the ventilator tubing may be fitted into the inside of the inlet end ID. In various embodiments, a ventilator tube may be connected to an inlet end and/or outlet end of a diffusing device utilizing a friction-fit connection, as would be known in the art. In various embodiments, the ID at the inlet end may be the same or different from the ID of the outlet end.

In one or more embodiments, gas(es) may enter the inlet end of the diffusing device 100 and exit the outlet end of the diffusing device, where the gas(es) may comprise a mixture of breathable gases. In various embodiments, the breathable gases may comprise air, or air and additional oxygen.

In various embodiments, the wall thickness 'C' of a cylindrical wall 115 may be in the range of about 1 mm (0.040 in.) to about 3.175 mm (0.125 in.), or in the range of about 1 mm (0.040 in.) to about 2 mm (0.079 in.), or in the range of about 1.588 mm (0.0625 in.) to about 2.388 mm (0.094 in.).

In one or more embodiments, the diffusing device may have a length 'D' in the range of about 6.35 mm (0.25 in.) to about 41.3 mm (1.625 in.), or in the range of about 22.225 mm (0.875 in.) to about 41.275 mm (1.625 in.), or in the range of about 25.4 mm (1.00 in.) to about 38.1 mm (1.50 in.).

In one or more embodiments, a nipple 190 for attaching a delivery tube to the diffusing device may protrude from the outer surface of the cylindrical wall 115. In various embodiments, the nipple may have a diameter 'M' 4.5 mm diameter (0.177") and protrude from the outer surface of the cylindrical wall 115 a height 'N' 8.7 mm (0.34 in.). In various embodiments, the nipple may comprise hose barbs for affixing a delivery tube.

In one or more embodiments, the device further comprises a projection 195 extending from the inner surface of the cylindrical wall 115. In various embodiments, the projection 195 may extend a radial distance 'P' into the hollow internal region 118. In various embodiments, the projection 195 may extend up to or close to the center of the hollow internal region 118, which would be half of the ID of the wall 115. In various embodiments, distance 'P' is slightly under half the ID so that the NO-containing gas will project out forward from the nozzle orifice to the middle, where the FGF gas velocity is higher than at the inner surface of the cylindrical wall. Accordingly, in various embodiments, the difference between 'P' and 'B'/2 is in the range of from about 0.1 mm to about 5 mm, or about 0.5 mm to about 3 mm. In exemplary embodiments, the difference between 'P' and 'B'/2 is about 1.5 mm, i.e. the projection 195 ends about 1.5 mm from the center of the hollow internal region 118. Exemplary differences between 'P' and 'B'/2 can have a lower limit of about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.1 mm, about 1.2 mm, about 1.3 and about 1.4 mm, and exemplary upper limits can be about 5 mm, about 4.5 mm, about 4 mm, about 3.5 mm, about 3 mm, about 2.5 mm, about 2.4 mm, about 2.3 mm, about 2.2 mm, about 2.1 mm, about 2 mm, about 1.9 mm, about 1.8 mm, about 1.7 mm and about 1.6 mm.

In some embodiments, 'P' is provided as a certain percentage of 'B', such as about 50%, about 49%, about 48%, about 47%, about 46%, about 45%, about 40%, about 40%, about 35%, about 30%, about 25%, about 20%, about 15%, about 10% or about 5% of 'B'. In exemplary embodiments, 'P' is between about 40% and about 45% of 'B'.

In one or more embodiments, the dimensions 'B', 'P', 'L', etc. may be selected to achieve desired relationships between the dimensions and/or desired relationships between gas properties under certain conditions. For example, 'B' and 'L' may be selected such that for a given source gas concentration and a given desired NO dose (e.g. 20 ppm), the gas velocity at the lowest expected FGF will be approximately equal to the gas velocity of the NO-containing gas. As another example, 'B' and 'L' may be selected such that for a given source gas concentration, the gas velocity of the FGF will be similar to the gas velocity of the NO-containing gas over a range of desired NO doses (e.g. 5 ppm to 80 ppm). As another example, 'B' and 'P' may be selected such that the NO-containing gas projects out forward from the nozzle orifice to a distance from the inner surface of the cylindrical wall, such as at or near center of the hollow internal region 118. As a further example, 'B' and 'P' may be selected such that the NO-containing gas projects out forward from the nozzle orifice to a portion of the FGF having a certain percentage of the peak velocity of the FGF, such as 99%, 98%, 95%, 90%, 85%, 80%, 75%, 70%, 65%, 60%, 55%, 50%, 45%, 40%, 35%, 30%, 25%, 20% or 10% of the peak velocity of the FGF.

In various embodiments, an injection channel 180 leading to an injection port 185 may be formed in the nipple, where the injection channel 180 has an inside diameter of 'L'. In various embodiments, the inside diameter 'L' may be in the range of about 0.8 mm (0.03125 in.) to about 2.4 mm (0.094 in.), or about 1.6 mm (0.0625 in.). Exemplary lower limits include about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm and about 1.6 mm. Exemplary upper limits include about 4.75 mm, about 4.5 mm, about 4 mm, about 3.5 mm, about 3 mm, about 2.5 mm, about 2.4 mm, about 2.29 mm, about 2.2 mm, about 2.1 mm, about 2 mm, about 1.9 mm, about 1.8 mm, about 1.7 mm and about 1.6 mm. The injection channel provides a flow path for delivery of a gas (e.g., NO) to the hollow internal region 118 of the diffusing device 100.

In one or more embodiments, the diffusing device 100 does not comprise a nipple 190 projecting from the body 110, but has a female connector into which a delivery tube may be plugged, where the female connector allows the delivery tube to be connected to and in fluid communication with the injection channel 180. In various embodiments, the ID of the delivery tube and the ID of the injection channel are the same and/or have a uniform cross-sectional area.

In one or more embodiments, the injection port 185 may be an orifice allowing a gas flowing through the injection channel 180 to enter the hollow internal region 118 at an intended rate and/or velocity. In various embodiments, the injection port may be an opening of fixed dimension that may be the same or different from the diameter of the injection channel, which provides an intended flow velocity related to the flow rate. In various embodiments, more than one injection port 185 can be used, such as by having multiple injection ports 185 along the length of the projection 195 and/or by having multiple projections 195, with each projection 195 having one or multiple injection ports 185. As set forth above, the injection ports may inject the NO-containing gas into a portion of the FGF that is a distance from the edge boundary so that the NO-containing gas is injected into FGF having a high velocity, not a portion of the FGF having zero or low velocity. In some embodiments, when more than one injection ports 185 are used, the diameters of the injection ports 185 have smaller diameters than would be used for a single injection port 185 to ensure that the velocity of the NO-containing gas is not reduced and is maintained in proportion to FGF velocity.

In some embodiments utilizing multiple injection ports 185, only one or some of the injection ports 185 may be used at a time, with selection dependent on the set dose of NO. For example, the multiple injection ports 185 can have varying orifice diameters, with a smaller orifice diameter being used for lower set doses of NO and a larger orifice diameter being used for higher set doses of NO. In this way, the ratio of the velocities of the NO-containing gas and the FGF can be maintained at a constant ratio, even with different set doses of NO. In some embodiments, more ports 185 are used at higher set doses of NO and less injection ports 185 are used at lowers set doses of NO, to tailor the velocities of the NO-containing gas and the FGF to the desired ratio. In other embodiments, all of the multiple injection ports 185 may be used concurrently. In various embodiments, multiple injection ports 185 may be multiple proportional control valves as part of the injector module.

In one or more embodiments, a valve (not shown) and/or variable orifice can be in fluid communication with the injection port 185 and/or can be located at the injection port 185. The proportional valve and/or variable orifice can be adjusted to control the velocity of gas being injected from the injection channel 180 into the hollow internal region 118. In various embodiments, the size of a valve orifice and/or variable orifice and velocity of gas being injected through the injection port 185 may be adjusted in relation to the FGF velocity, where the valve and gas velocity may be controlled through a feedback loop. In various embodiments, the feedback loop may comprise a flow sensor capable of measuring fresh gas flow in the breathing circuit, where the flow sensor may be in electrical communication with a control module that controls the dosage of NO fed into the diffusing module 100 through the injection channel 180 and the valve and/or variable orifice by adjusting the valve and/or variable orifice. In one or more embodiments, the diffuser and flow sensor capable of measuring fresh gas flow are incorporated into a single piece, such as being integral to an injector module.

In one or more embodiments, the diffusing module 100 comprises a proportional control valve, an NO flow sensor and a FGF flow sensor for measuring the fresh gas flow in the breathing circuit and delivering a flow of NO-containing gas that is proportional to the FGF to provide the desired set dose of NO. In such embodiments, the proportional control valve and/or flow sensor can be eliminated from the control module. Such a configuration can eliminate a compressed gas volume between the control module and the diffuser, as the proportional valve within the diffusing module 100 is used as the primary valve for regulating the flow of the NO-containing gas into the breathing circuit. While not wishing to be bound by any particular theory, it is believed that having both a proportional valve in the diffusing module 100 and a proportional valve in the control module can result in compressed gas being stored within the injection channel and NO delivery tube at the end of each inspiratory cycle, and that this compressed gas may then decompress, allowing a quantity of NO-containing gas to enter the breathing circuit and causing over delivery of NO. This potential problem can be magnified with high concentration NO, due to the decreased delivery volume. Accordingly, substituting a proportional control valve in the diffusing module 100 for the proportional control valve in the control module can reduce or eliminate the impact of this potential problem.

In one or more embodiments, the NO-containing gas is injected into the FGF as a plurality of pulses from one or more injection ports 185. The plurality of pulses can be used to provide a higher velocity of the NO-containing gas than if the flow of the NO-containing gas was constant. By providing pulses (e.g. NO flow OFF-ON-OFF-ON), a higher instantaneous NO volumetric flow rate can be provided with a corresponding increase in instantaneous NO velocity, without providing a higher average volumetric flow rate than needed to provide the desired NO concentration in the combined gas stream. As an example, if the system was to detect low FGF bias flow (e.g. 0.5 SLPM), the NO can be delivered as a plurality of high-velocity pulses to maintain the correct quantity of NO-containing gas volume during this phase. In this way, the NO delivery system can utilize pulse width modulation of NO flow (e.g. during expiratory bias flow) to maintain a higher gas velocity of NO in proportion to FGF gas velocity, while maintaining the desired average NO flow rate or set dose concentration.

During expiratory phase only delivery of pulsatile high peak flow to increase the NO exit velocity. In order to maintain the correct quantity of gas volume during this phase. The pulsatile flow would be Off-ON-Off-On to meet the average flow rate required to meet set Dose. Pulse width modulation of NO flow.

Aspects of the invention also relate to method of diffusing a high concentration gas into a transverse gas stream comprising passing at least a portion of a first gas longitudinally through a hollow internal region of a body having an inner surface surrounding the hollow internal region, and passing a second gas stream through an injection channel to an injection port projecting into the hollow internal region of the body, wherein the second gas stream enters and at least partially diffuses with the first gas stream within the hollow internal region.

FIGS. 8C-D illustrate another exemplary device for diffusing a high concentration low volume gas flow and a high volume gas flow using the techniques disclosed above. Of course, other configurations capable of diffusing a high concentration low volume gas flow and a high volume gas flow using the above techniques are envisioned. The dimensions are exemplary for a 22 mm nominal diffuser for use with adult breathing circuits/fittings. It should be noted that the non-limiting examples of dimensions and/or configurations are intended for standard adult breathing circuits, and the dimensions and proportions of the device may be adjusted for applications involving standard neonate breathing circuits, standard pediatric breathing circuits, or other non-standard-sized breathing circuits without undue experimentation.

In one or more embodiments, the diffusing device 100 comprises an annular body 110 that may be a cylinder having a wall and a hollow internal region. The body may be configured and dimensioned to connect to tubing in a ventilator breathing circuit (10, 15 and 22 mm), fit into ventilator tubing, or have ventilator tubing fitted into the body. In various embodiments, the inlet end of the device comprises a male connection configured and dimensioned to join to a ventilator tube, and the outlet end comprises a female connection configured and dimensioned to join to a ventilator tube or humidifier chamber inlet. In a non-limiting example, the inlet end of the device comprises a 22 mm (O.D.) male connection, and the outlet end comprises a 22 mm (I.D.) female connection. In addition, the diffusing device 100 can be a component or part of an injector module which couples to a ventilator breathing circuit, as is known in the art.

In one or more embodiments, the annular body 110 may have an outside diameter 'A' at an inlet end and/or an outlet end. The outside diameter 'A' may be in the range of about 10 mm (0.394 in.) to about 25 mm (1.0 in.), or about 22 mm (0.866 in.), where the ventilator tubing may be fitted around the outside of the inlet end OD and inside the outlet end ID. In various embodiments, a ventilator tube may be connected to an inlet end and/or outlet end of a diffusing device utilizing a friction-fit connection, as would be known in the art.

In one or more embodiments, the annular body may have an inside diameter 'B' at an outlet end and/or an inlet end. The inside diameter 'B' may be in the range of about 10 mm (0.394 in.) to about 25 mm (1.0 in.), or about 22 mm (0.866 in.), where the ventilator tubing may be fitted into the inside of the inlet end ID. In various embodiments, a ventilator tube may be connected to an inlet end and/or outlet end of a diffusing device utilizing a friction-fit connection, as would be known in the art.

In one or more embodiments, gas(es) may enter the inlet end of the diffusing device 100 and exit the outlet end of the diffusing device, where the gas(es) may comprise a mixture of breathable gases. In various embodiments, the breathable gases may comprise air, or air and additional oxygen.

In various embodiments, the wall thickness 'C' of the diffusing device 100 may be in the range of about 1 mm (0.040 in.) to about 3.175 mm (0.125 in.), or in the range of about 1 mm (0.040 in.) to about 2 mm (0.079 in.), or in the range of about 0.0625 to about 0.094.

In one or more embodiments, the diffusing device may have a length 'D' in the range of about 6.35 mm (0.25 in.) to about 41.3 mm (1.625 in.), or in the range of about 22.225 mm (0.875 in.) to about 41.275 mm (1.625 in.), or in the range of about 25.4 mm (1.00 in.) to about 38.1 mm (1.50 in.).

In one or more embodiments, the device further comprises a tapered section 150 comprising a wall, which may have a truncated cone, a funnel, or a bell shape, where the tapered section 150 narrows from an inside diameter 'E' at a first (inlet) end to an inside diameter 'F' at a second (outlet) end opposite the first end, wherein the opening at the first (inlet) end has a larger diameter than the opening at the second (outlet) end. In various embodiments, the first end having a larger diameter is a mouth 152, and the second end having the smaller diameter is a throat 158.

In one or more embodiments, an accelerator may comprise a tapered section or a bi-directional tapered section.

In various embodiments, the inside diameter 'E' at the mouth 152 may be in the range of about 14 mm (0.511 in.) to about 18 mm (0.709 in.), or about 16.03 mm (0.631 in.).

In various embodiments, the inside diameter 'F' at the throat 158 may be in the range of about 3.17 mm (0.125 in.) to about 9.5 mm (0.375 in.), or about 6.35 mm (0.250 in.).

In one or more embodiments, the tapered section 150 may have a length 'I' from the leading edge of the mouth 152 to the trailing edge of the throat 158. In various embodiments, the length 'I' of the tapered section 150 may be in the range of about 8 mm (0.315 in.) to about 13 mm (0.519 in.), or about 10.3 mm (0.405 in.).

In one or more embodiments, the inside surface of the tapered section forms a sharp corner at the leading edge of the mouth 150, so there are no flat surfaces perpendicular to the axis of the tapered section. In various embodiments, the wall of the tapered section may have a thickness in the range of about 1 mm to about 2 mm or about 1.5 mm.

In one or more embodiments, the tapered section 150 may be located inside the body 110 of the diffusing device 100. In various embodiments, the tapered section may be suspended from a cylindrical wall 115 of the annular body 110 by a support 160, wherein the support 160 may extend from an inner surface of the cylindrical wall 115 into the open internal region 118. In various embodiments, the annular body 110, tapered section 150, and support joining the tapered section 150 to the annular body may be one integral piece, where the annular body 110, tapered section 150, and support 160 are molded as a single piece, so the components comprise a single unitary construction. In various embodiments, the tapered section 150 and the annular body 110 are coaxial. In one or more embodiments, the projection 195 may form the support 160 by interconnecting the body 110 and the tapered section 150.

In one or more embodiments, there may be a gap 151 between the rim of the mouth 152 and the inside surface of the cylindrical wall 115, where the gap 151 has a size 'G' in the range of about 0.5 mm (0.02 in.) to about 3 mm (0.118 in.), which provides an opening around the rim of the mouth 152. In various embodiments, the opening allows at least a portion of the incoming gas(es) to by-pass the tapered section 150 by flowing along the periphery of the internal region and around the tapered section 150.

In one or more embodiments, the opening has a cross-sectional area in the range of about 9.5% to about 19.0% of the cross-sectional area of the internal region In one or more embodiments, the gap 151 has a cross-sectional area in the range of about 15% to about 35% of the cross-sectional area of the internal region where the internal region defined as B diameter is 20 mm.

In one or more embodiments, the tapered section 150 may be a distance 'H' from the leading edge of the annular body 110. In various embodiments, the distance 'H' from the leading edge of the annular body 110 may be in the range of 3.175 mm (0.125 in.) to about 12.7 mm (0.50 in.). In various embodiments, dimension H may be reduced to thereby minimize the size and weight of the device.

In one or more embodiments, the tapered section 150 may be a distance 'J' from the trailing edge of the annular body 110. In various embodiments, the distance 'J' from the trailing edge of the annular body 110 may be in the range of 3.175 mm (0.125 in.) to about 12.7 mm (0.50 in.), In various embodiments, dimension J may be reduced to thereby minimize the size and weight of the device.

In one or more embodiments, a nipple 190 for attaching a delivery tube to the diffusing device may protrude from the outer surface of the cylindrical wall 115. In various embodiments, the nipple may have a diameter 'M' of about 4.5 mm diameter (0.177 in.) and protrude from the outer surface of the cylindrical wall 115 a height 'N' of about 8.7 mm (0.34 in.).

In various embodiments, an injection channel 180 leading to an injection port may be formed in the nipple, where the injection channel 180 has an inside diameter of 'L'. In various embodiments, the inside diameter 'L' may be in the range of about 0.8 mm (0.03125 in.) to about 2.4 mm (0.094 in.), or about 1.6 mm (0.0625 in.).

In one or more embodiments, the opening forming the injection port 185 at the internal end of the injection channel 180 may be located proximal to region where fresh gas velocity is maximized in diffuser device (e.g. a distance 'K' from the outlet end of the tapered section 150. In various embodiments, the distance 'K' may be in the range of about 2 mm (0.787 in.) to about 5 mm (0.197 in.), or about 3 mm (0.118 in.) from the outlet end of the tapered section 150).

In one or more embodiments, the NO injection port may terminate at the throat wall, or an extension tube may project further into the throat from the internal surface of the tapered section. In various embodiments, the extension tube may project into center of the throat.

In one or more embodiments, the injection port may be 6.81 mm from the leading edge of the tapered section.

In one or more embodiments, the tapered section may be suspended within a hollow cylindrical portion of a housing, wherein the housing is adapted to connect to ventilator tubing. In various embodiments, the housing may have a shape other than cylindrical or annular while having an inlet and outlet configured and dimension to connect to suitable ventilator tubing. For example a rectangular housing of a diffusing device may have cylindrical inlet and outlet openings with an I.D. to connect to tubing.

In one or more embodiments, a diffusing device may be utilized in a ventilator circuit, with a nasal cannula, or with a face mask.

Figure 9C:
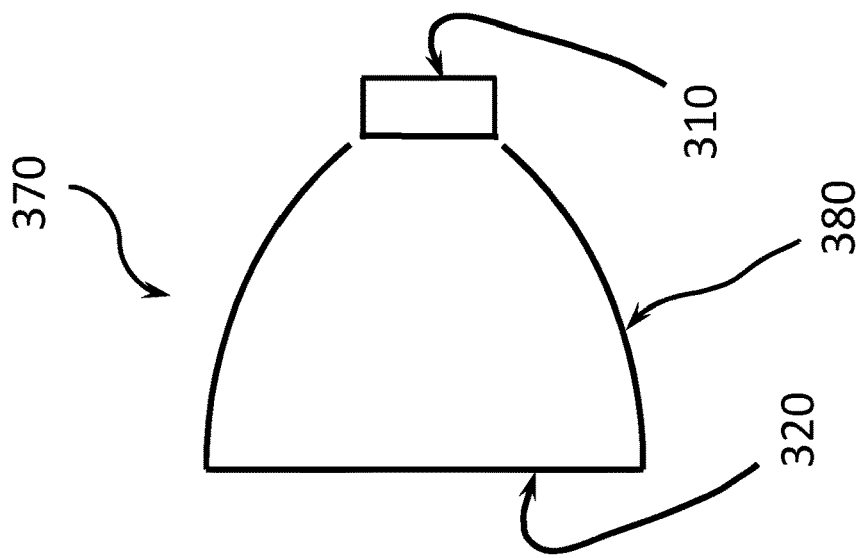
FIG. 9C illustrates an exemplary embodiment of a tapered section having a bell shape.
Figure 9B:
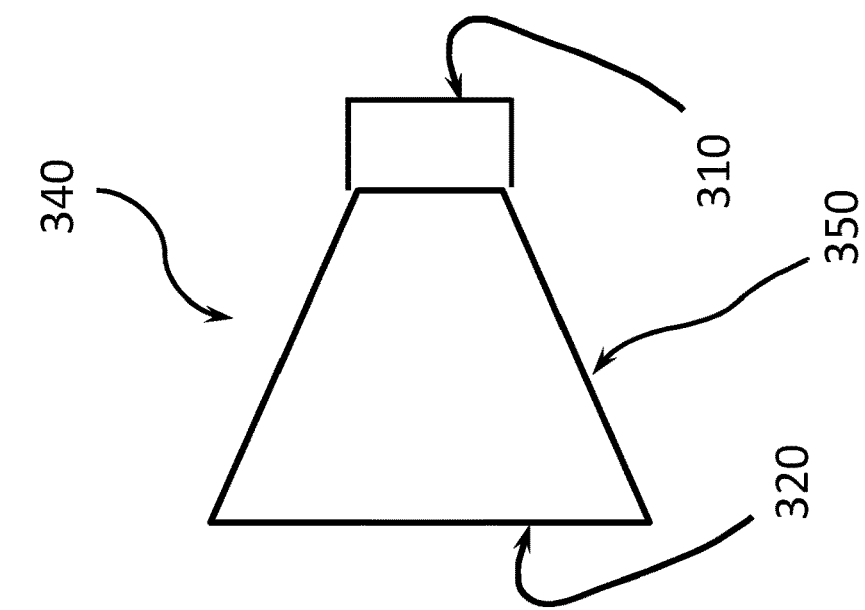
FIG. 9B illustrates an exemplary embodiment of a tapered section having a cone shape.
Figure 9A:
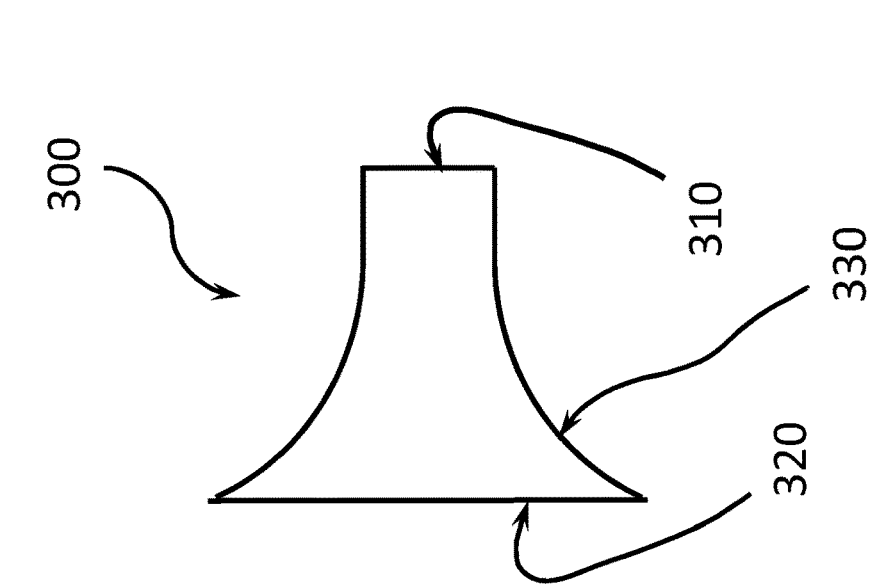
FIG. 9A illustrates an exemplary embodiment of a tapered section having a funnel shape.

FIG. 9A illustrates an exemplary embodiment of a tapered section 300 having a funnel shape.

In one or more embodiments, the funnel shaped tapered section 300 has an internal surface 330 that is convex, and directs gas(es) entering the mouth 320 towards the throat 310. In various embodiments, the convex contour of the internal surface may have a constant curvature or a changing curvature.

FIG. 9B illustrates an exemplary embodiment of a tapered section 340 having a cone shape.

In one or more embodiments, the cone shaped tapered section 340 has an internal surface 350 that is straight from the mouth 320 of the tapered section 340 to the throat 310, and directs gas(es) entering the mouth 320 towards the throat 310.

FIG. 9C illustrates an exemplary embodiment of a tapered section 370 having a bell shape, where the bell shape may have constant curvature or a changing curvature.

In various embodiments, a tapered section, as depicted in 300, 340, and 370 may be adjoined throat-to-throat to provide a bi-directional tapered section to allow for insertion and use in a ventilation circuit in either orientation. FIG. 10 illustrates an exemplary embodiment of a bi-directional tapered section. A bi-directional tapered section 700 may comprise two tapered sections 150 coupled at their throats, where the injection valve provides for injection of a gas at the narrowest portion of the bidirectional tapered section 700. In various embodiments, the two tapered sections may be coupled at a throat comprising a cylindrical section 740. In various embodiments, the injection port would be located where the two tapered sections join, and the FGF velocity should be at a maximum at the lowest expected FGF rate. In some embodiments, a tapered section is utilized in environments in which the FGF rate is expected to be low, e.g. less than 2 SLPM.

In one or more embodiments, the bell shaped tapered section 370 has an internal surface 380 that is concave, and directs gas(es) entering the mouth 320 towards the throat 310.

Figure 11:
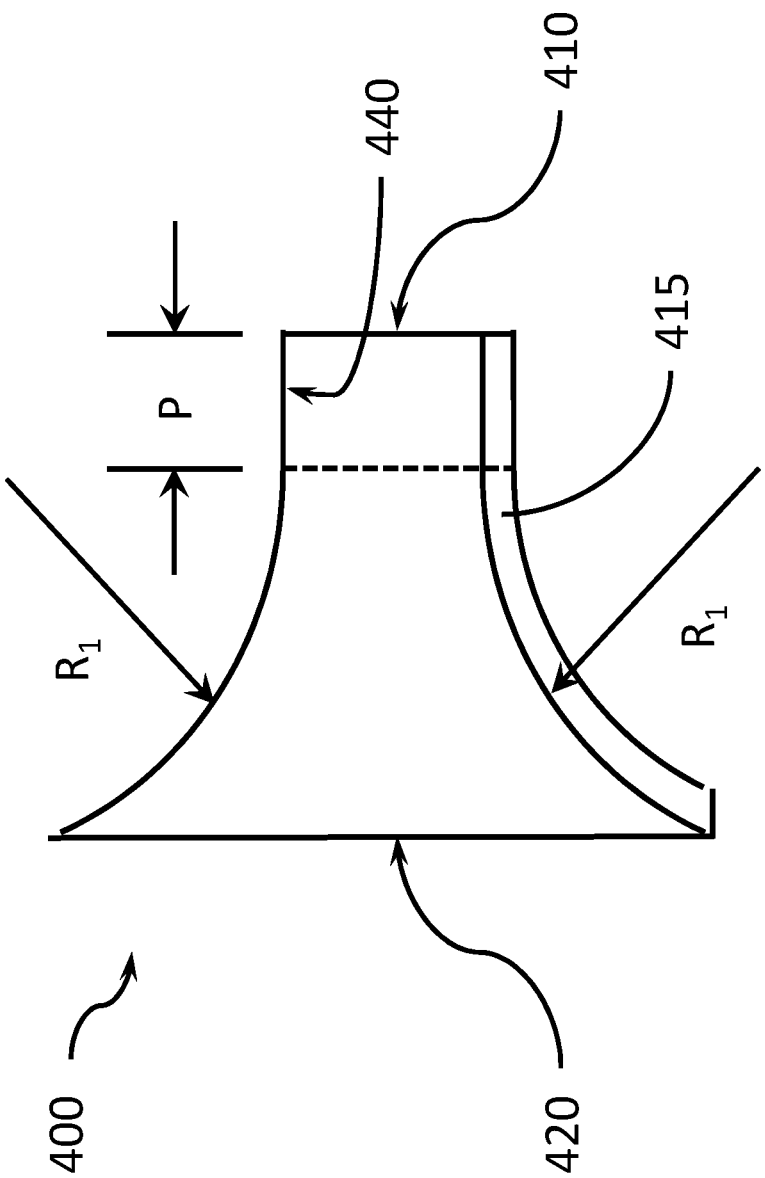
FIG. 11 illustrates an exemplary tapered section depicting a convex contour of an inside surface of a tapered section wall.

FIG. 11 illustrates an exemplary tapered section 400 depicting a contour of an inside surface of a tapered section wall 415.

Principles and embodiments of the present invention also relate to diffusing device comprising a tapered section 400 comprising a decreasing cross-sectional area that increases the velocity of the gas flow past the injection port and exiting the throat 410, so a high concentration gas is quickly dispersed and diffused with the ventilator gas.

In one or more embodiments, the tapered section 400 can be an axially-symmetrical tube with a variable cross-sectional area, where area is decreasing from the mouth 420 area to the throat 410 area. In various embodiments, the wall 415 may have a straight, parabolic, hyperbolic, catenoidal, or funnel contour.

In one or more embodiments, the tapered section 400 may comprise a cylindrical section 440 with a constant diameter and cross-sectional area that extends a length 'P' from the point that the cross-sectional area is at a minimum, and/or the slope of the tapered section becomes 0 (zero) (i.e., horizontal).

In various embodiments, the tapered section creates an increasing pressure gradient, so flow or boundary separation cannot occur because of the favorable pressure gradient. The avoidance of boundary separation also avoids reverse-flow regions and vortices that may deplete the energy of the gas flow and increase flow resistance. The pressure drop for a volumetric flow rate of 60 SLPM may be approximately 0.65 cm $H_2O$, and at 30 SLPM may be approximately 0.16 cm $H_2O$.

In one or more embodiments, the contour of the tapered section wall 430 has a constant curvature with a radius $R_1$, where $R_1$ may be in the range of 7.5 mm (0.296 in.) to about 8.3 mm (0.328 in.), or about 7.6 mm (0.299 in.).

An aspect of the present invention relates to a method of diffusing a high concentration gas into a transverse gas stream.

FIG. 12 illustrates an exemplary embodiment of a second gas passing through an injection channel 180 into a first gas passing through a tapered section 150. (Gas flows are indicated by straight and curved arrows.)

In one or more embodiments, at least a portion of a first gas enters a diffusing device 100 and passes through a tapered section 150 comprising a wall 155 having a thickness, an outer surface and an inner surface, an inlet end having a first diameter, and an outlet end having a second diameter opposite the inlet end, wherein the second diameter is smaller than the first diameter; and passing a second gas stream through an injection channel 180 to an injection port 185 in the inner surface of the tapered section 150. In various embodiments, the second gas stream enters and at least partially diffuses with the first gas stream within the tapered section 150. In various embodiments, the injection of the second gas at an intended flow rate and velocity into the stream of the first gas creates sufficient diffusing at the point contact or confluence of the two gas streams. In various embodiments, the intended volumetric flow rate of the second gas (NO at 1-80 ppm dose) may be in the range of about 0.1 SMLPM to about 33.3 SMLPM for 4880 ppm NO, where the volumetric flow rate of the second gas (NO) is proportional to the volumetric flow rate of the first gas (FGF) when the first gas flow rate is in the range of about 0.5 SLPM to about 2.0 SLPM.

In one or more embodiments, at least a portion of the first gas passes around at least a portion of the outer surface of the tapered section, wherein the tapered section 150 is within an annular body 110 having an outer surface and an inner surface, and an inside diameter that is larger than the first diameter of the tapered section. In various embodiments, at least a portion of the first gas passes through the gap 151 between the rim 153 of the mouth 152 and the inside surface of the cylindrical wall 115.

In one or more embodiments, the first gas is a breathable gas comprising molecular $N_2$ and molecular $O_2$, and the second gas comprises molecular NO and molecular $N_2$.

In one or more embodiments, the first gas is provided by a ventilator at a flow rate in the range of about 0 liters per minute (SLPM) to about 120 liters per minute (SLPM). In some instances, as described herein, during expiratory flow there may be flows in the range 0.5 SLPM to 2 SLPM that may result in higher NO2 being generated. Accordingly, in at least some instances, the disclosed techniques may be directed towards these lower flow rates.

In various embodiments, the concentration of NO in the second gas is in the range of greater than 800 ppm to about 5000 ppm, or about 2000 ppm to about 4880 ppm, or about 4800 ppm.

In one or more embodiments, the flow rate of the second gas is linearly proportional to the flow rate of the first gas.

In one or more embodiments, the second gas stream initially enters the first gas stream at an angle in the range of about 60° to about 120°, or at an angle in the range of about 75° to about 105°, or about 80° to about 100°, or about 85° to about 95°, or at about 90° to the axis of the first gas stream. In various embodiments, the second gas may be injected perpendicularly to the first gas stream, where the two perpendicular gas streams act to impart turbulence at the point of contact, to reduce $NO_2$ levels to a value equal to or less than the amount generated by the current 800 ppm therapy.

Without being limited by theory, it is believed that sufficient diffusion results when FGF is impinged by intersecting NO flow, where the NO and FGF have sufficient velocity at ventilator bias flows. In addition, a short annular outlet just after the point of NO injection may allow for a quick divergence of the once compressed FGF gas within the tapered section, now combined with NO, to exit abruptly and freely diffuse with bypass flow around the tapered section.

In one or more embodiments, the second gas exits the injection port 185 at a flow rate in the range of about 0.1 milliliters per minute (SMLPM) to about 6.3 SLPM, or about 0.05 milliliters per minute (SMLPM) to about 2 SLPM, or about 1.0 milliliters per minute (SMLPM) to about 1 SLPM. A gas flow rate of 2 SLPM has a velocity of approximately 0.42 meters/sec. through an injection channel and injection port with a 0.16 cm I.D. A gas with this velocity would not experience noticeable compression at this velocity when passing through the diffusing device, which is less than 0.2×the speed of sound (i.e., Mach Number <0.2). A gas flow rate of 0.5 SLPM has a velocity of approximately 0.10 meters/sec. through an injection channel and injection port with a 0.16 cm I.D. It can be helpful to manage $NO_2$ conversion during periods of very low ventilator flow rates (e.g., bias flow during exhalation ≤2 SLPM), increased oxygen concentrations ($FiO_2 \geq 60\%$), and higher NO set dosage (≥20 ppm).

In one or more embodiments, the velocity of the first gas is greater at the second diameter of the tapered section 150 than the velocity of the first gas at the first diameter of the tapered section 150.

In one or more embodiments, the velocity of the first gas is greater at the second diameter of the tapered section than the velocity of the first gas at the first diameter of the tapered section, wherein the second gas enters the first gas at a point of greater velocity. In various embodiments, the tapered section generates an increase gas velocity and pressure gradient towards the middle of the annular body, such that the highest gas velocity is along the axis of the tapered section 150. For example, a reduction of the tapered section 150 I.D. from 1.6 cm at the mouth to 0.635 cm at the throat would result in an increase in the first gas velocity. In some instances, the ratio of inlet to outlet gas velocities is proportional to the ratio of inlet to outlet areas.

Figure 12:
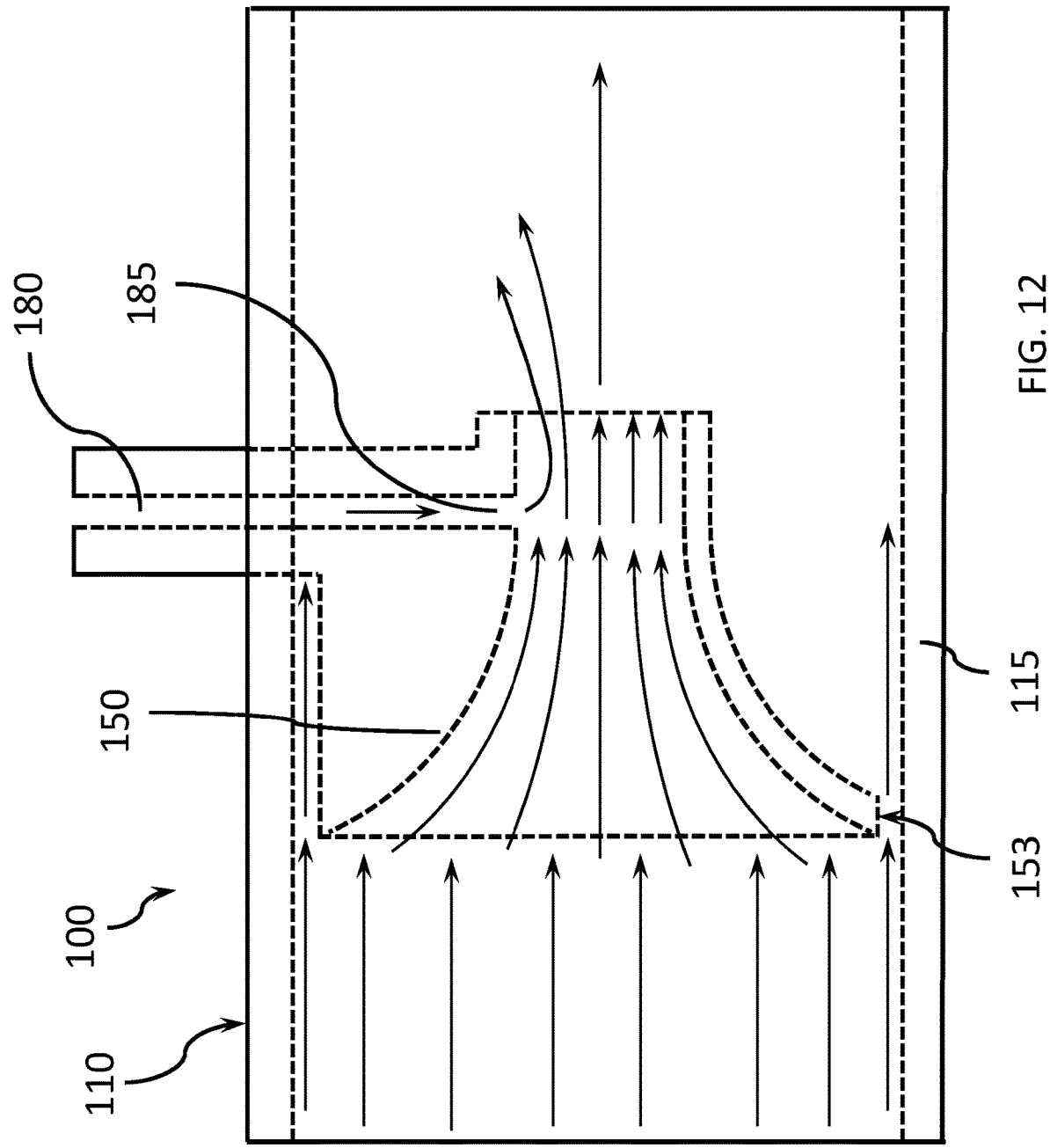
FIG. 12 illustrates an exemplary embodiment of a second gas passing through an injection channel into a first gas passing through a tapered section.

As can be seen in FIG. 12, the second gas enters the first gas at the injection port 185, which is closer to the throat of the tapered section 150, and where the velocity of the first gas flow has increased compared to the first gas velocity at the mouth of the tapered section.

Figure 13:
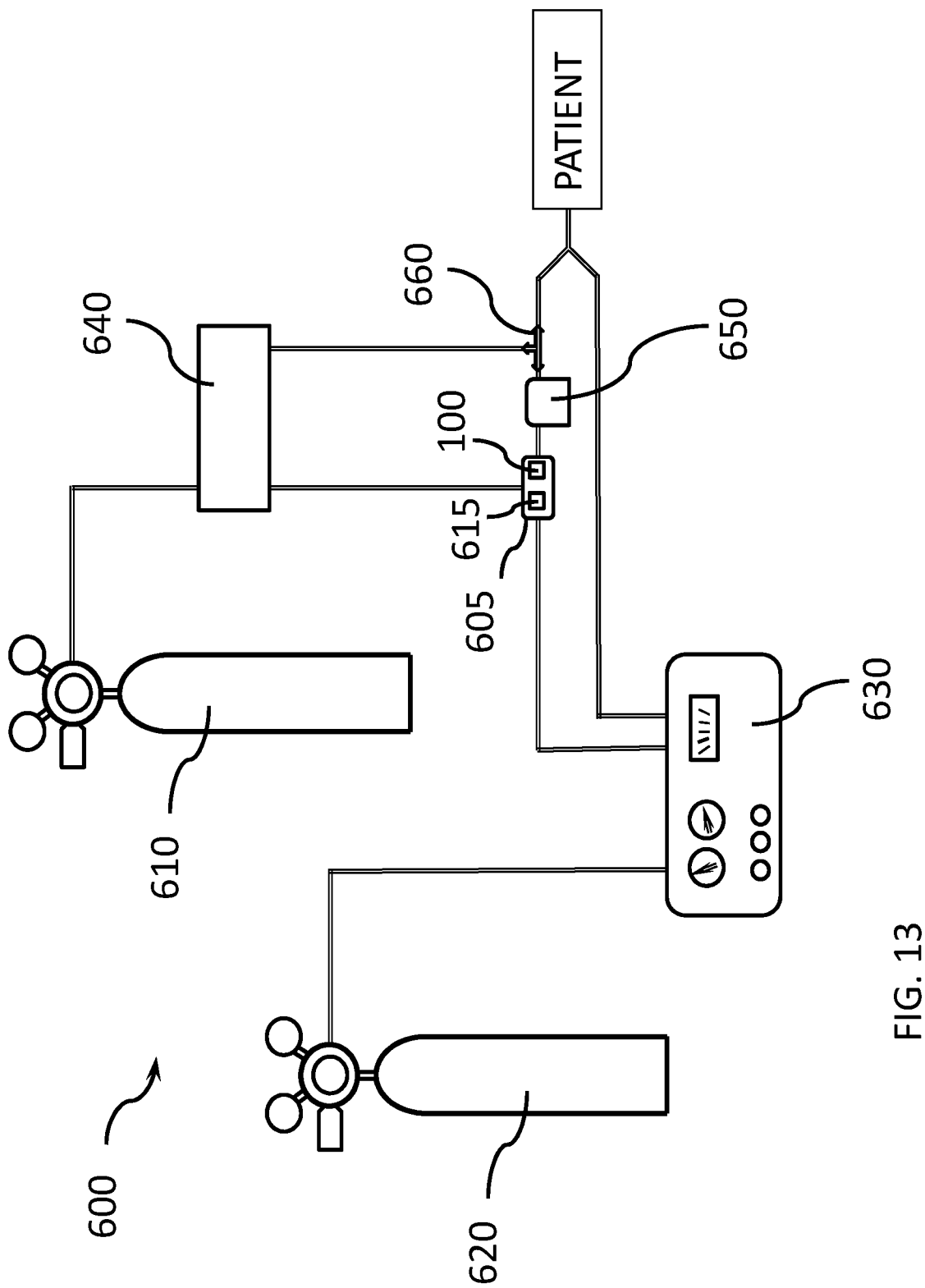
FIG. 13 illustrates an exemplary embodiment of a diffusing device inserted into a ventilator circuit.

FIG. 13 illustrates an exemplary embodiment of a diffusing device 100 inserted into a ventilator circuit 600. In various embodiments, the ventilator system may provide elevated (>21%) fractional inspired oxygen ($FiO_2$) concentrations along with NO doses to mechanically ventilated patients. Oxygen concentration in patient ventilator circuits may range from medical air (21% $O_2$) to medical oxygen (100% $O_2$), but are generally elevated to 60% for patients receiving INO therapy. The NO in a high concentration NO gas source 610 may be diluted with nitrogen $N_2$.

In one or more embodiments, a diffusing device 100 (e.g., as a component in an injector module 605, downstream of a flow sensor 615 capable of measuring fresh gas flow in the breathing circuit, etc.) may be connected to and in fluid communication with ventilator tubing coming from a ventilator 630. The ventilator may be connected to and in fluid communication with a fresh gas source 620. The diffusing module 100 may also be connected to and in fluid communication with a control module 640 that controls the dosage of NO fed into the diffusing module 100. The control module 640 may be connected to and in fluid communication with a NO gas source 610. In various embodiments, the fresh gas source 620 and NO gas source 610 may have regulators to control the pressure from the cylinders. In various embodiments, the diffusing device may be connected to and in fluid communication with a humidifier 650 that adds water vapor content to the inspiratory gas flow to the patient. In various embodiments, the distance from the diffusing device 100 to the patient may be approximately 1 meter. In various embodiments, the humidifier may have a compressible volume of about 280 ml. In various embodiments, the diffusing device 100 and the flow sensor 615 are integral to the injector module 605.

In one or more embodiments, the diffusing device diffuses the incoming fresh gas flow from the ventilator 630 and fresh gas source 620 with the incoming NO-containing gas from the NO gas source 610 flowing through the control module 640. The gas flow being delivered to the patient may be sampled at a sampling tee 660 inserted down stream from the humidifier 650 and/or diffusing device 100. In various embodiments, NO, $NO_2$, and/or $O_2$ concentrations may be monitored before reaching the patient. The sampling tee 600 can be placed at various positions in the breathing circuit, depending on how quickly the NO-containing gas and FGF combine to provide a homogenous gas stream at the set dose. Furthermore, a plurality of sampling points may be used, such as sampling points located at various distances from the NO injection point. 1, 2, 3, 4, 5, 6, 7, 8, 9, 10, 15, 20, 25, 30 or more sampling points may be used. The distance between sampling points can be 1, 2, 3, 4, 5, 6, 7, 8, 9, 10, 15, 20, 25 or 30 cm. The plurality of sampling points can be used to separately analyze the combined gas stream as a function of length down the breathing circuit, or two or more sampling can be combined to provide an average for the composition of the gas.

As explained in the Examples below, an increase in temperature has surprisingly been found to decrease the amount of $NO_2$ that is generated under otherwise similar conditions. Accordingly, embodiments of the present invention also relate to minimizing $NO_2$ generation by heating one or more portions of the NO delivery system and/or ventilator circuit. While not wishing to be bound by any particular theory, it is believed that an increase in gas temperature can increase the available kinetic energy with the gas molecules, which can promote initial mixing resulting in further $NO_2$ reduction.

For example, a heating element may be added to the NO delivery system, the tubing from the NO delivery system to the injector module, the injector module and/or the tubing of the inspiratory limb of the ventilator circuit, and/or may be placed at any other location upstream, downstream or at the point of injection. The heating element may be a heated humidifier or may be a dedicated heating component. Exemplary heating elements include, but are not limited to, a thermoelectric cooling device or a resistive heating element. A heating element in the NO delivery system can help minimize $NO_2$ generated internally within the NO delivery system. Likewise, heating elements placed in, and/or in thermal communication with, the tubing that deliver the NO to the injector module and from the injector module to the patient can help minimize $NO_2$ generation at those points.

In various embodiments, the heating element can heat the NO source gas and/or the combined NO and FGF to a desired temperature. Exemplary temperatures include, but are not limited to, about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 45° C. or about 50° C.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1—$NO_2$ Generation System Comparison

Figure 14:
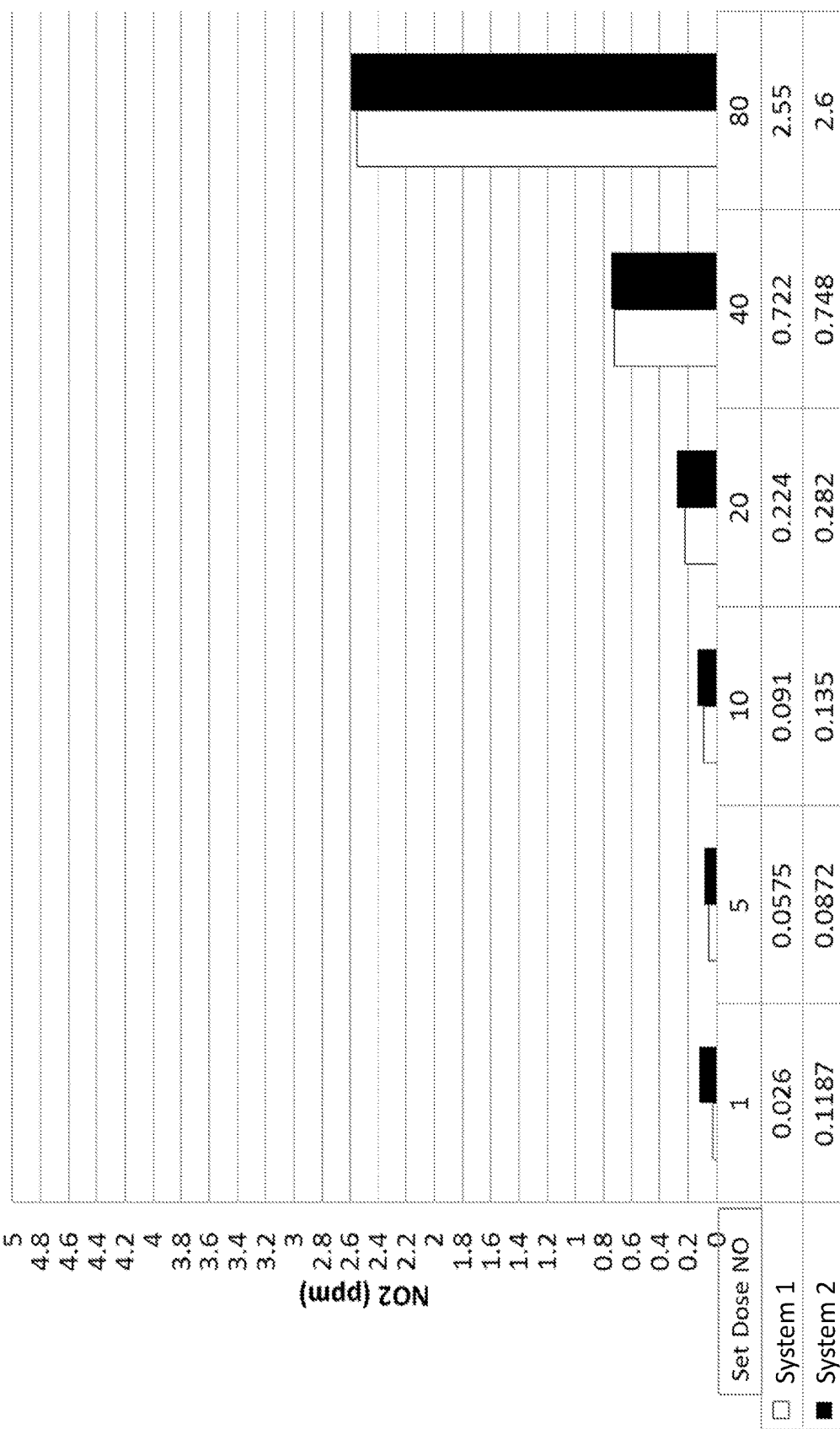
FIG. 14 shows a comparison of the $NO_2$ generated during mechanical ventilation using an exemplary diffuser described herein and a conventional low source concentration injector module.
Figure 15A:
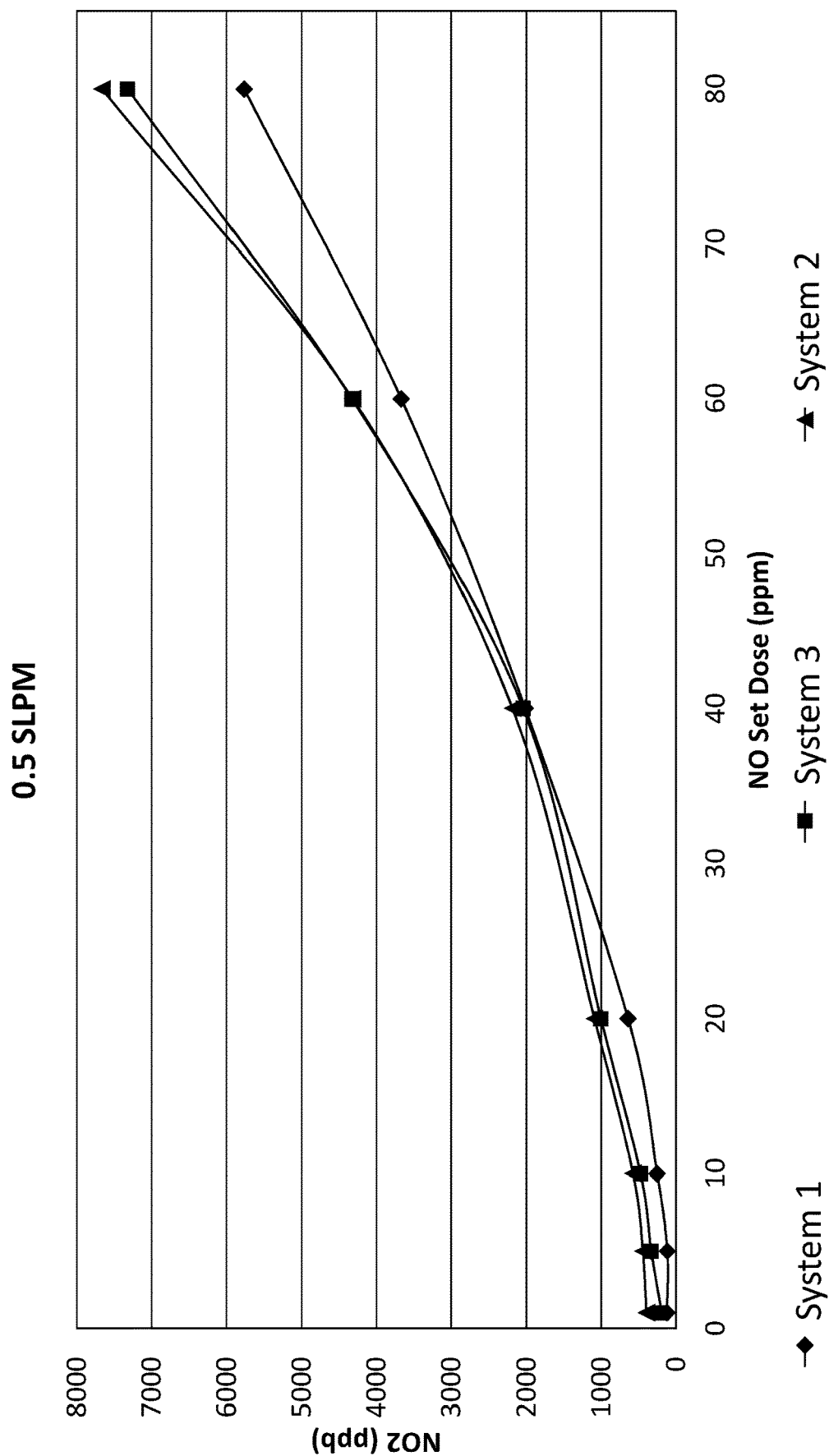
FIGS. 15A-F show a comparison of the $NO_2$ generated under steady state FGF flow conditions within smooth bore tubing using an exemplary diffuser described herein, an exemplary accelerator as described herein, and a conventional low source concentration injector module.
Figure 15B:
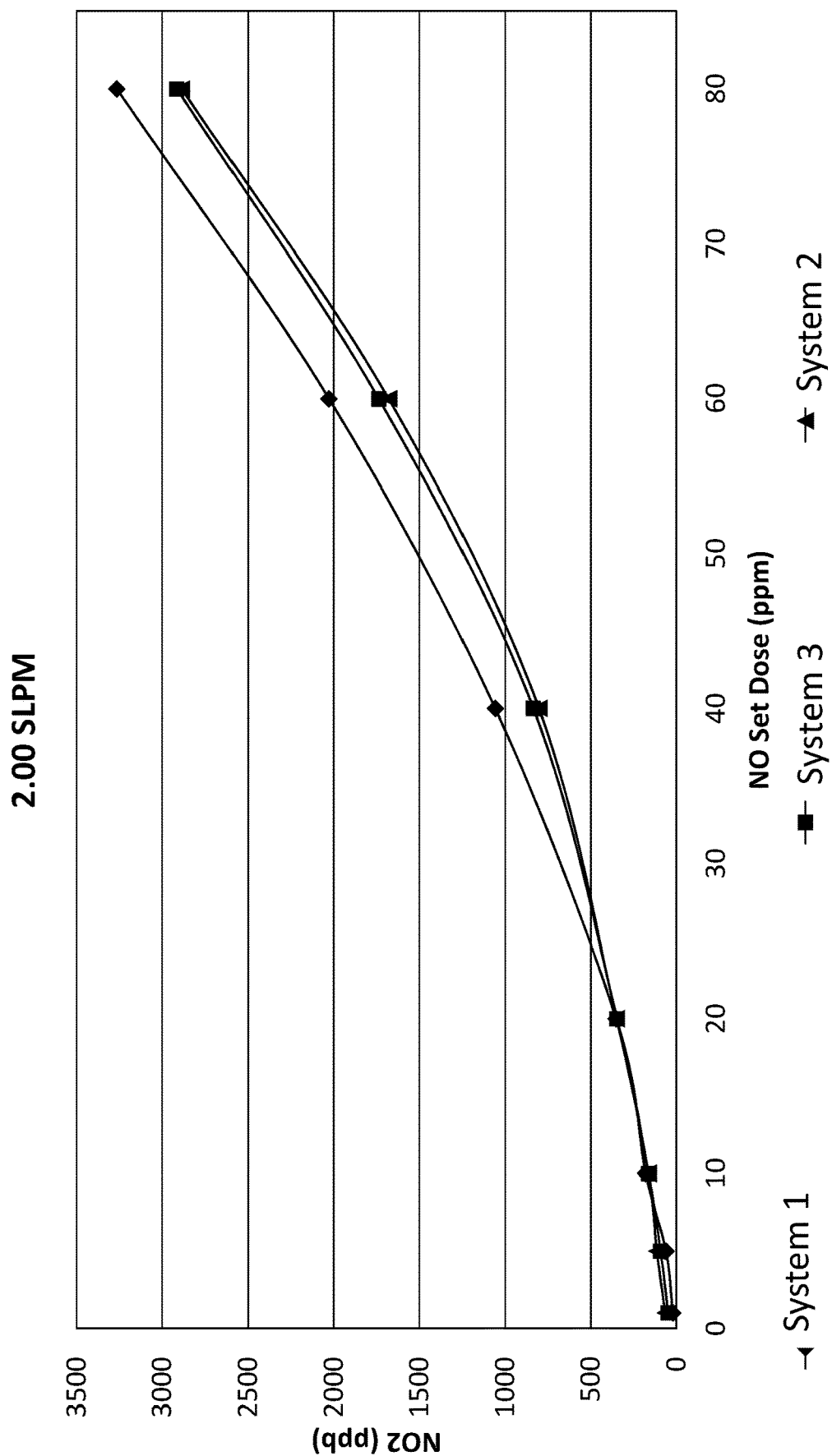
Figure 15C:
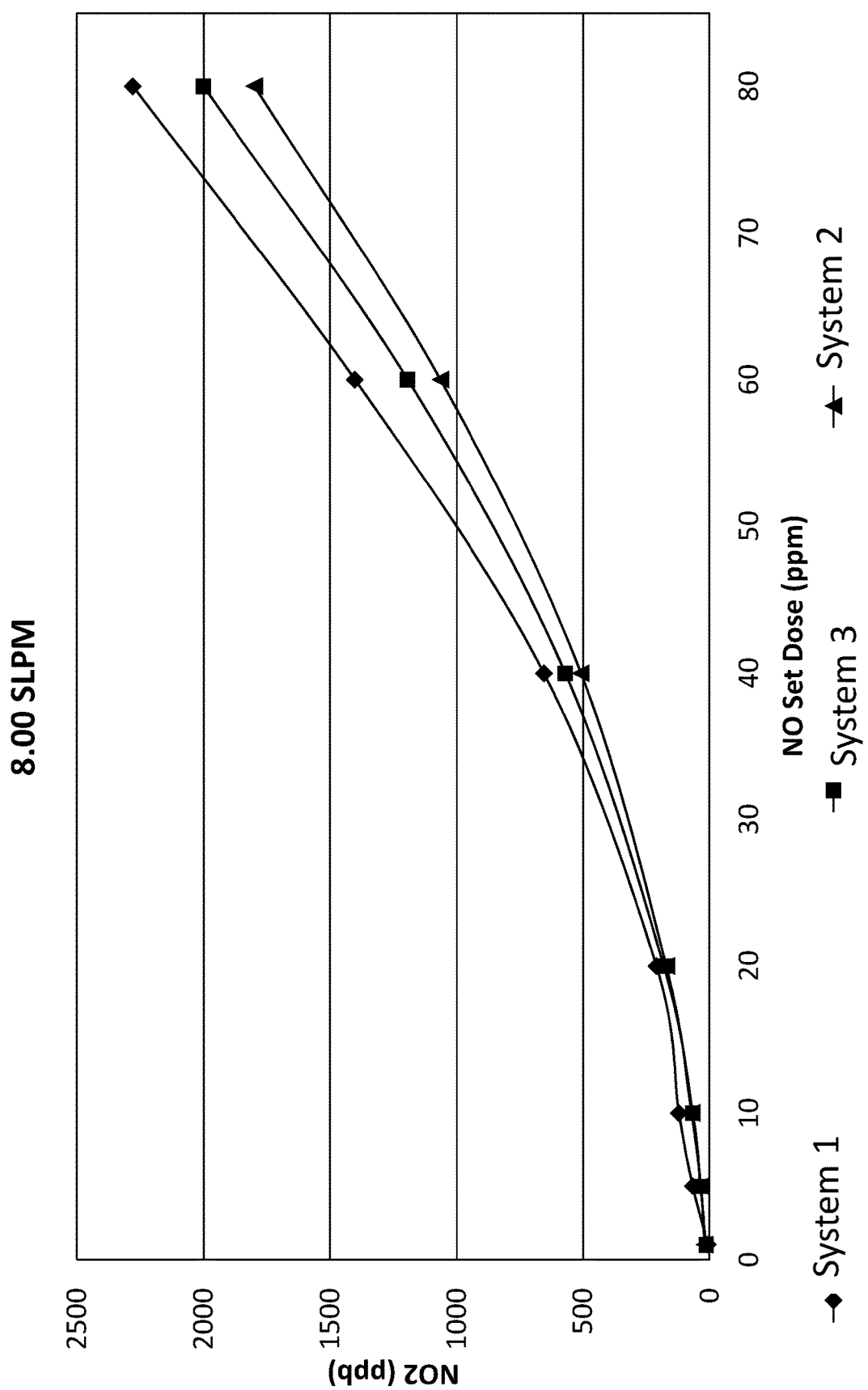
Figure 15D:
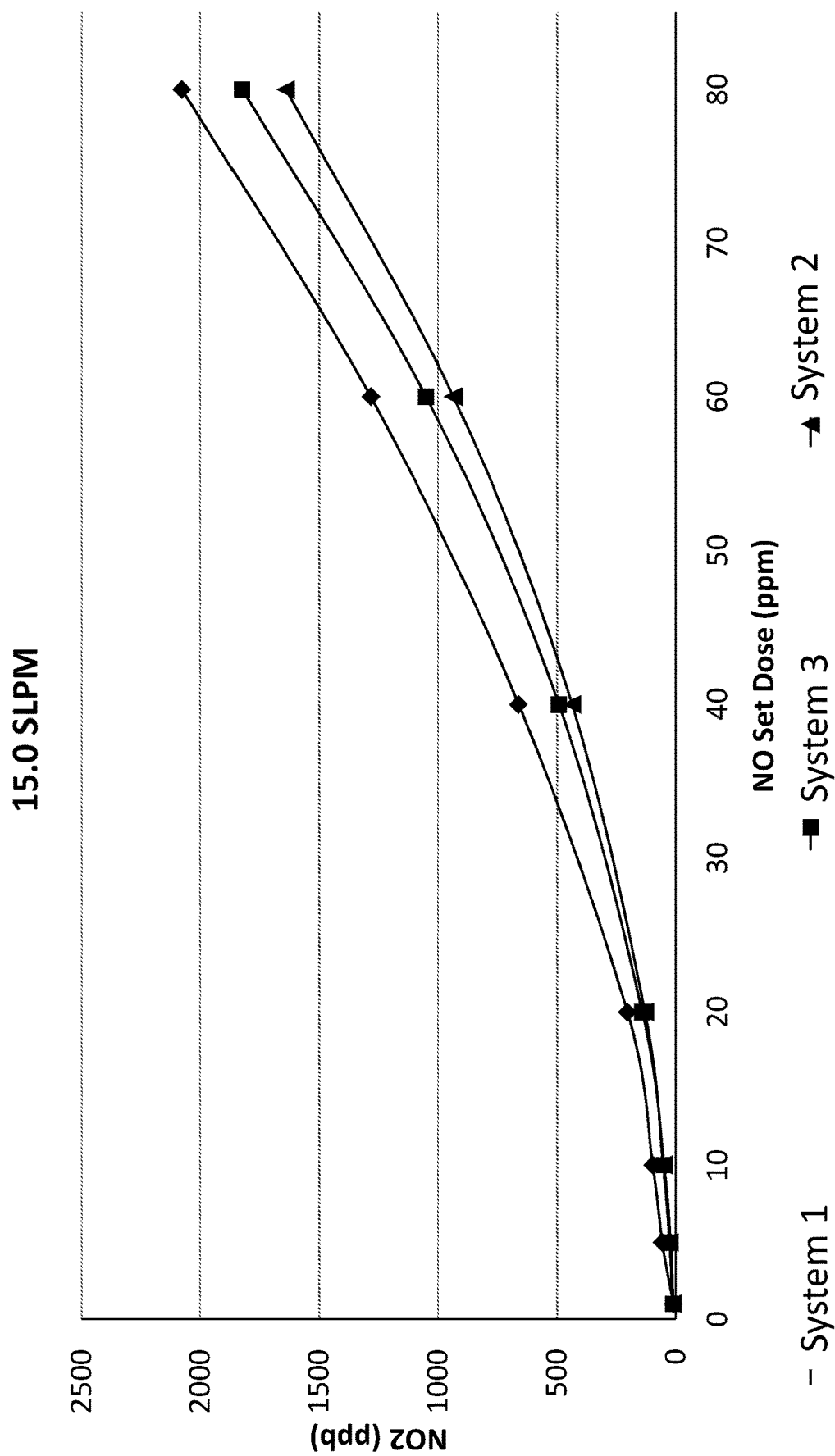
Figure 15E:
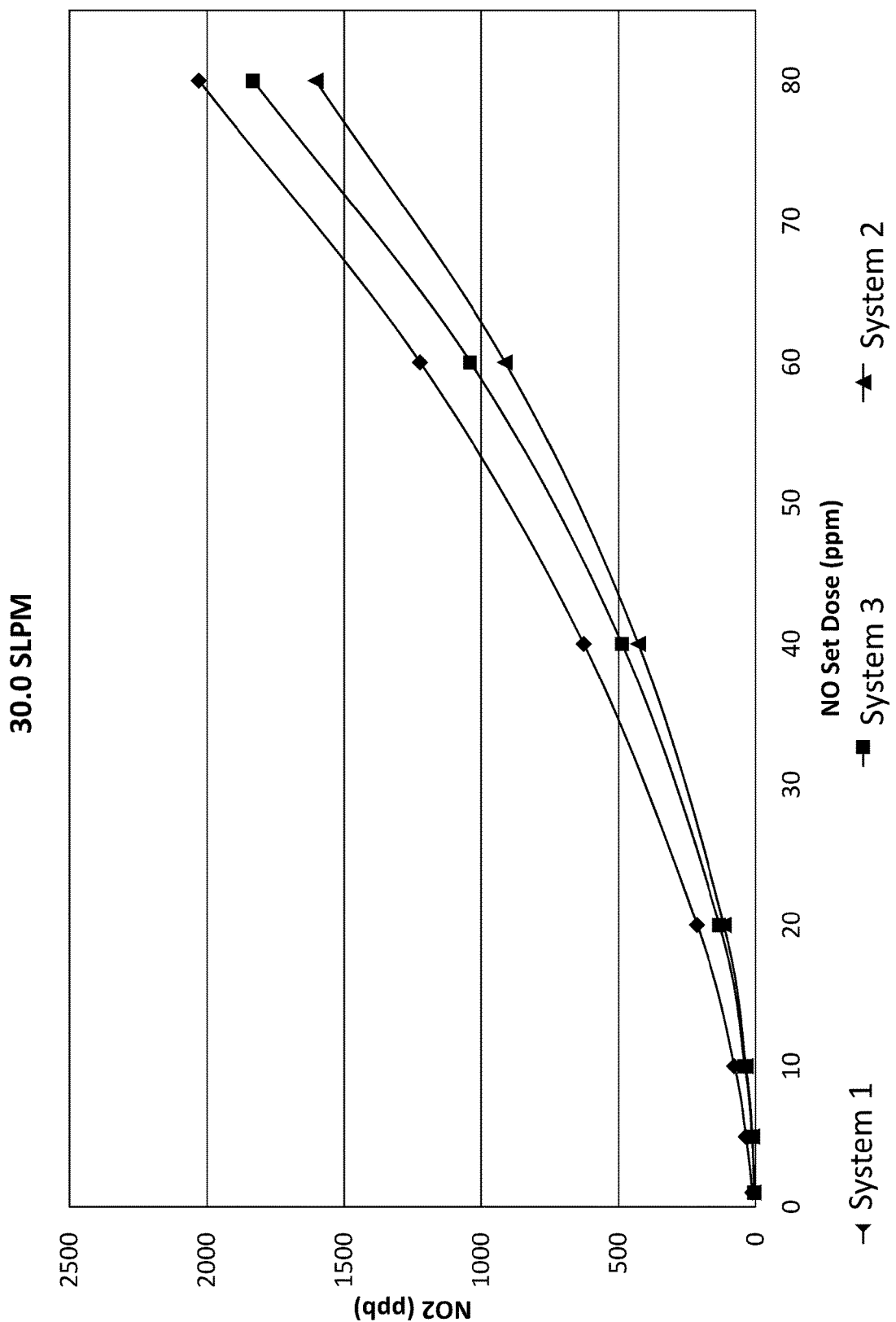
Figure 15F:
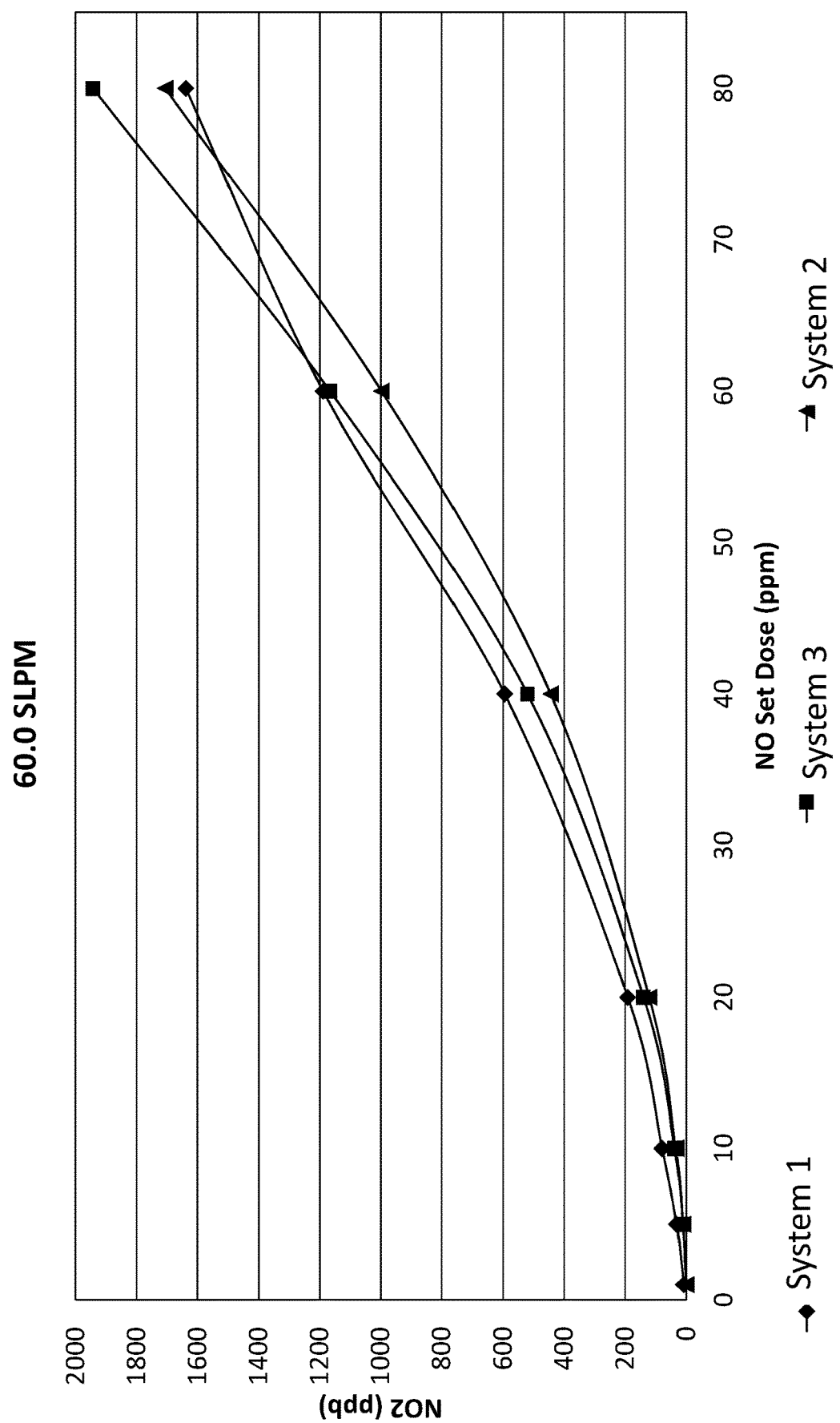

A NO delivery system utilizing a high NO source concentration (e.g. 4880 ppm) and an injector module with an exemplary diffuser as described herein (e.g. a diffuser as shown in FIGS. 8A-B) was compared to a conventional NO delivery system utilizing a low NO source concentration (e.g. 800 ppm) and a conventional injector module. The FGF was provided by a neonatal ventilator with exemplary ventilation parameters (e.g. respiratory rate of 40, tidal volume of 30 ml, $FiO_2$ of 60%, 0.5 SLPM bias flow, etc.). As can be seen from FIG. 14, the high NO source concentration system utilizing a diffuser (System 2) produced a comparable amount of $NO_2$ as the conventional NO delivery system at a lower NO source concentration (System 1), despite a significantly higher NO source concentration.

System 1 and System 2 were also compared to a NO delivery system utilizing a high NO source concentration (e.g. 4880 ppm) and an injector module with an exemplary accelerator as described herein (e.g. an accelerator as shown in FIGS. 8C-D), which is designated System 3. FIGS. 15A-F show the $NO_2$ produced for each system at various NO set doses and FGF flow rates. As can be seen from FIGS. 15A-F, both Systems 2 and 3 at the high NO source concentration produced a comparable or lower amount of $NO_2$ at a set dose of 40 ppm as the conventional NO delivery system at a lower NO source concentration. While not wishing to be bound by any particular theory, it is believed that the relatively low $NO_2$ values for Systems 2 and 3 at 40 ppm is a result of the FGF and NO-containing gases having similar velocities. As can be seen from Table 3 below, the velocity of the NO-containing gas was most similar to the FGF velocity at 40 ppm for the particular configurations tested as Systems 2 and 3.

TABLE 3

Velocity of NO-Containing Gas for Systems 2 and 3

| | | NO Velocity (cm/sec) NO Dose | | | | |
|---|---|---|---|---|---|---|
| | | 5 | 10 | 20 | 40 | 80 |
| FGF | 3.67 | 0.4 | 0.9 | 1.8 | 3.6 | 7.3 |
| Velocity | 14.7 | 1.8 | 3.6 | 7.2 | 14.5 | 29.2 |
| (cm/sec) | 58.79 | 7.2 | 14.4 | 28.9 | 58 | 117 |
| | 110.23 | 13.5 | 27 | 54.1 | 108.7 | 219.3 |
| | 220.46 | 27 | 54 | 108.3 | 217.5 | 438.6 |
| | 440.92 | 54 | 108.1 | 216.6 | 435 | 877.2 |

Example 2—$NO_2$ Generation with Heated System

Figure 16:
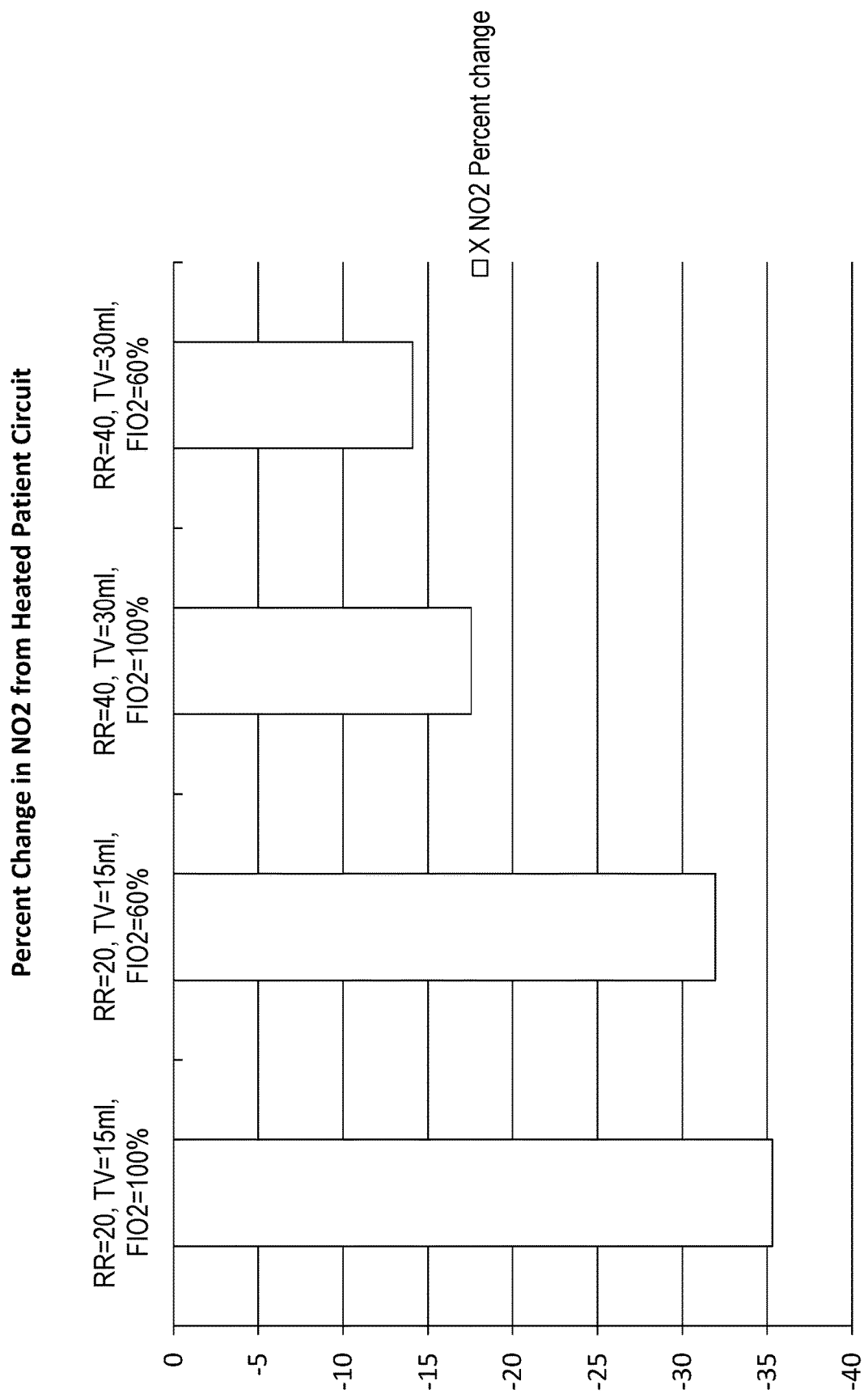
FIG. 16 shows the reduction of the $NO_2$ generated by heating an exemplary ventilator breathing circuit.

The NO delivery system used in System 2 of Example 1 was then used with a heated ventilator breathing circuit (e.g. about 38° C.). As can be seen from FIG. 16, heating the ventilator breathing circuit reduced the $NO_2$ levels under all conditions tested.

Although the invention herein has been described with reference to particular embodiments, it is to be understood that these embodiments are merely illustrative of the principles and applications of the present invention. It will be apparent to those skilled in the art that various modifications and variations can be made to the devices, systems, and methods of the present invention without departing from the spirit and scope of the invention. Thus, it is intended that the present invention include modifications and variations that are within the scope of the appended claims and their equivalents.

Example 3—$NO_2$ Minimization Using Gas Velocity Ratio

The NO delivery system used in System 2 of Example 1 was modified to have various NO source concentrations and to provide various ratios of the FGF velocity to the NO-containing gas velocity. A plurality of gas sampling points was used for NO and $NO_2$ concentration measurements, which was averaged to account for any inhomogeneous distribution of the gases within the cross-section of the tube. The $NO_2$ concentration was measured at three different points downstream from the NO injection point T0:T1 (203 mm downstream from NO injection point), T2 (673 mm downstream from NO injection point) and T3 (2268 mm downstream from NO injection point). For the experiments described below, the region from T0 to T1 was considered to have a non-homogeneous gas distribution and the region from T2 to T3 was considered to have a homogenous gas distribution. The $NO_2$ conversion rate was determined by subtracting the $NO_2$ contribution from the NO source cylinder from the measured $NO_2$ concentration, and dividing the net gain in $NO_2$ concentration by the residence time between sample points (volumetric flow rate divided by the volume of the segment).

Figure 17:
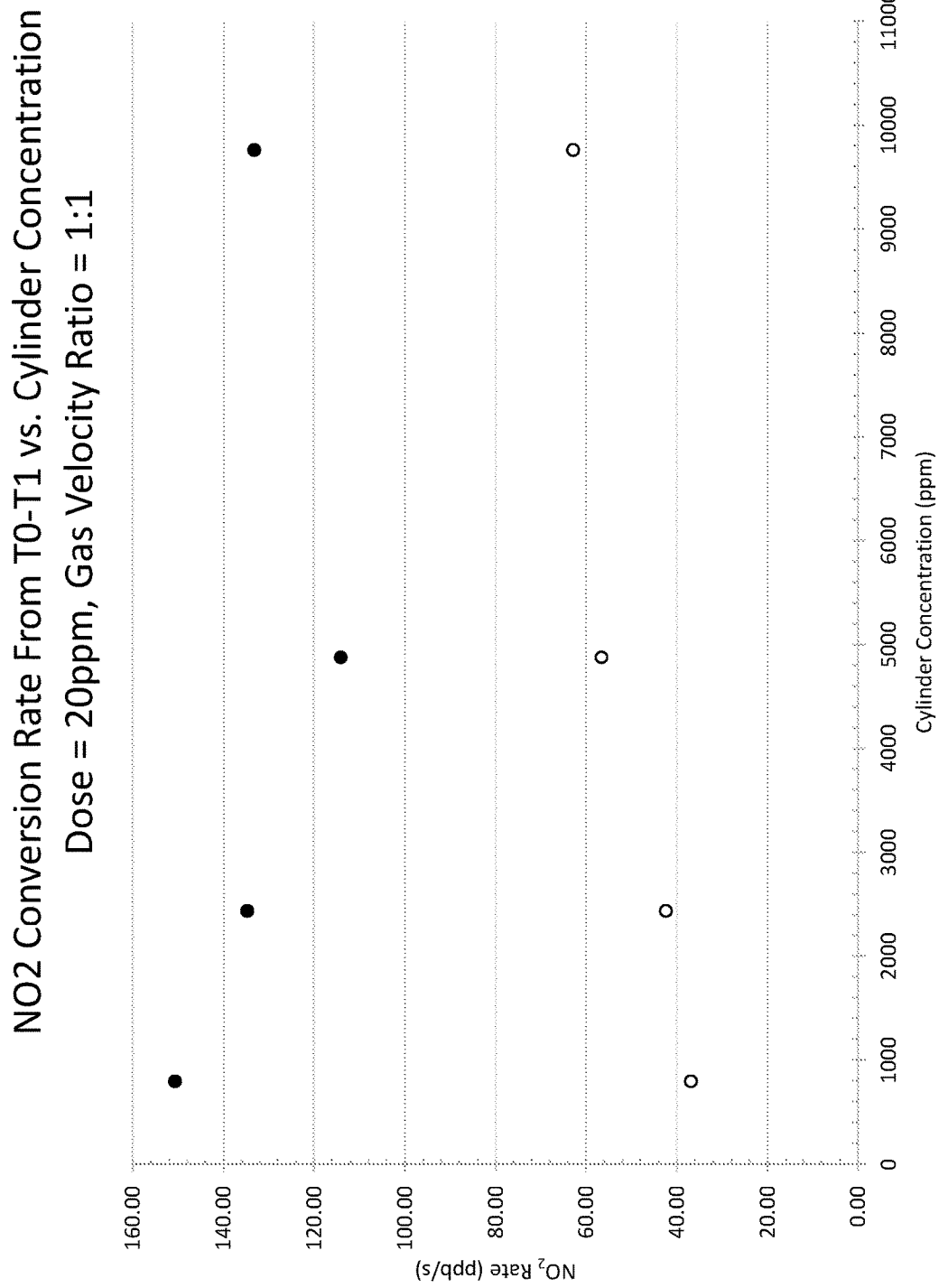
FIG. 17 shows the $NO_2$ generated in the initial region with various NO source cylinder concentrations ranging from 800 ppm to 9760 ppm with a gas velocity ratio (FGF:NO) of approximately 1:1.
Figure 18A:
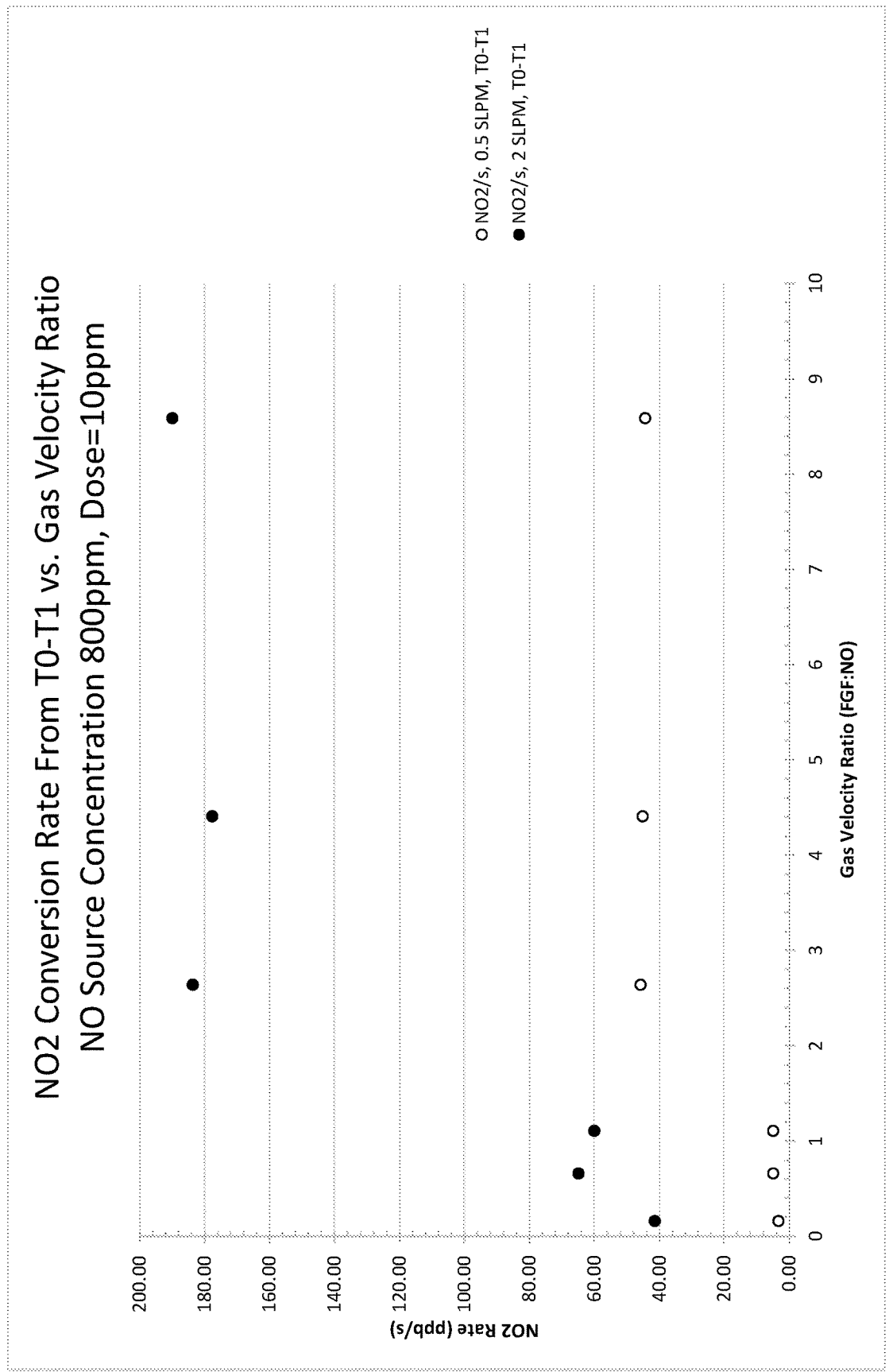
FIGS. 18A-D show the $NO_2$ generated in the initial region with various NO source cylinder concentrations ranging from 800 ppm to 9760 ppm with a varying gas velocity ratio (FGF:NO) and a set dose of 10 ppm NO.
Figure 18B:
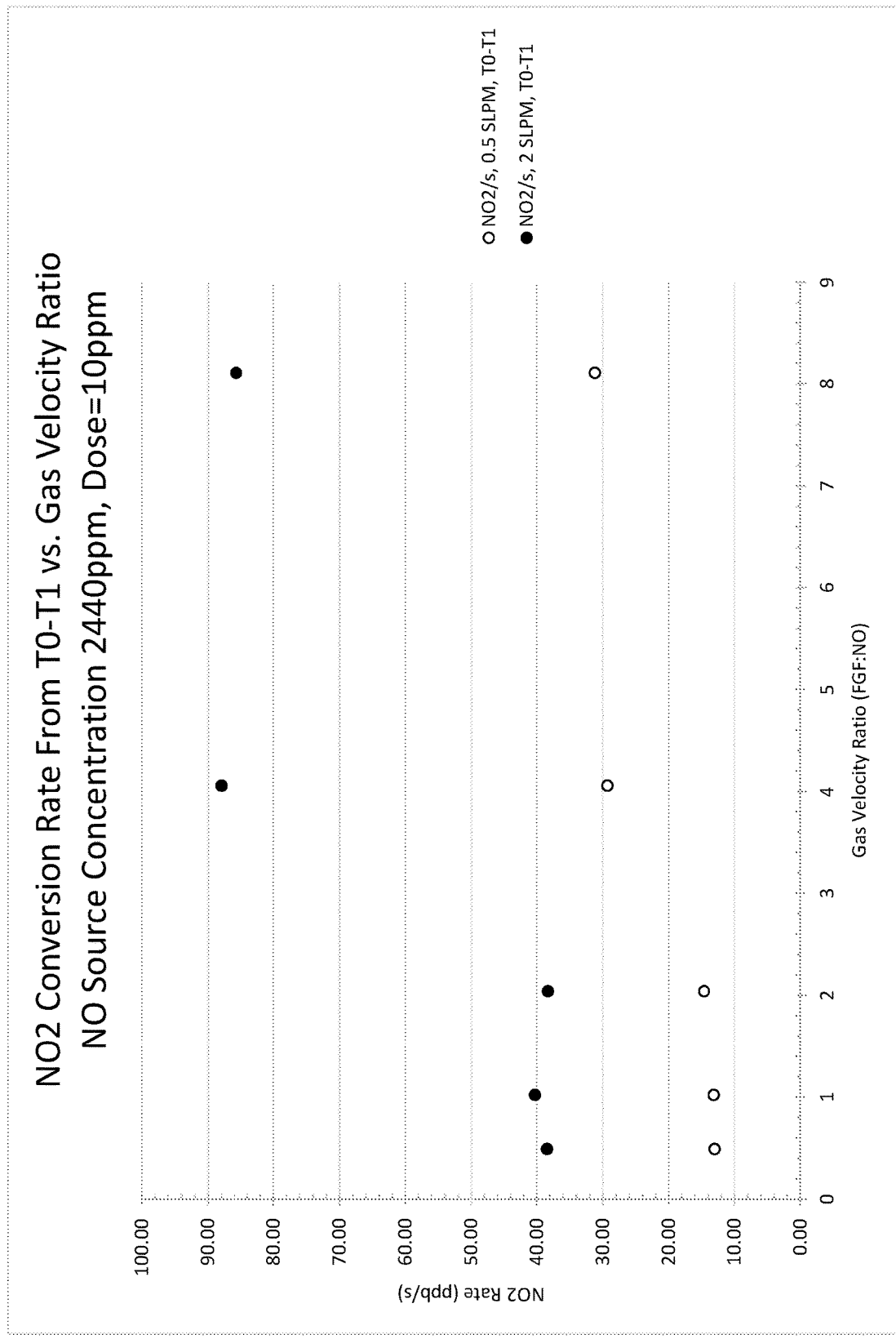
Figure 18C:
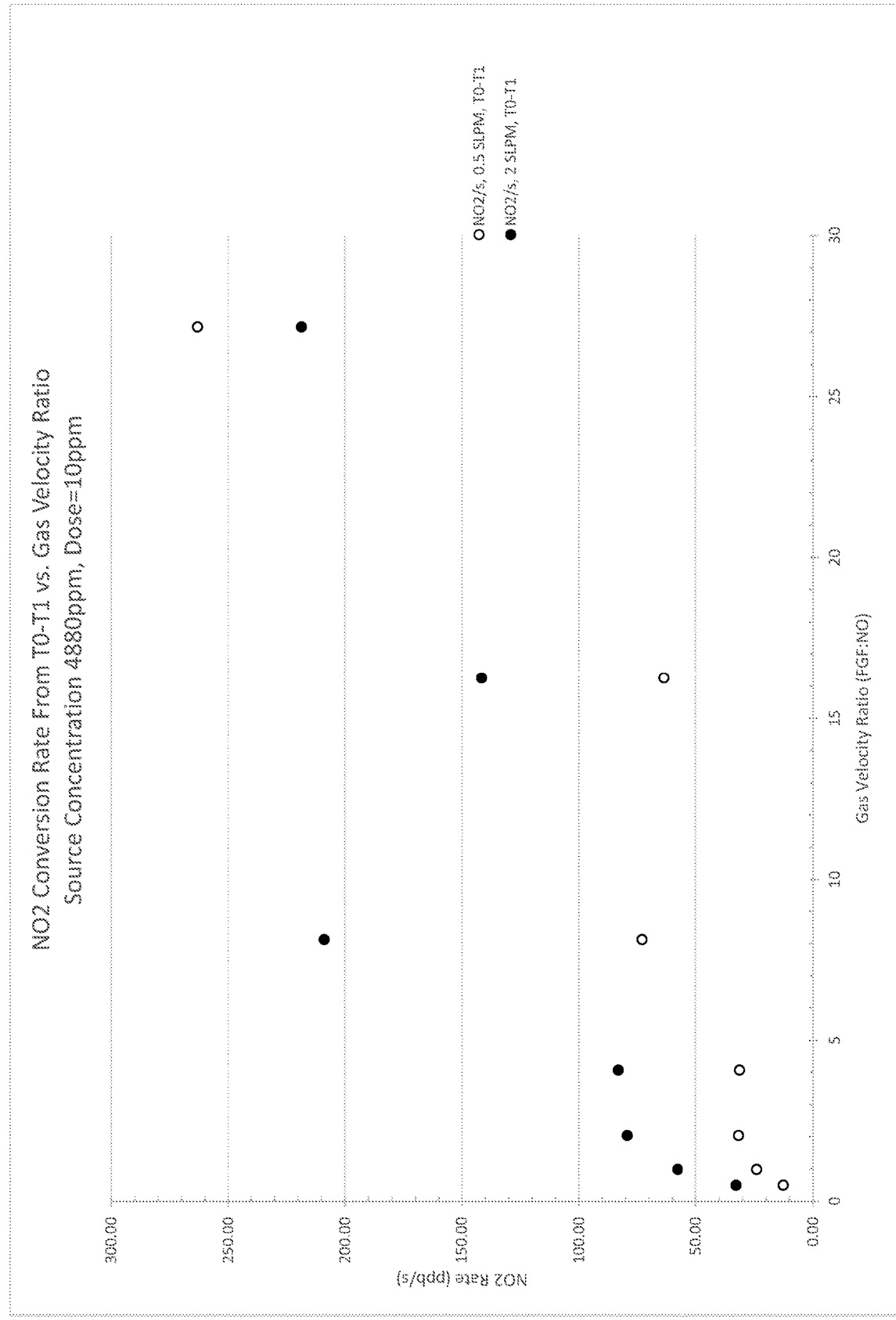
Figure 18D:
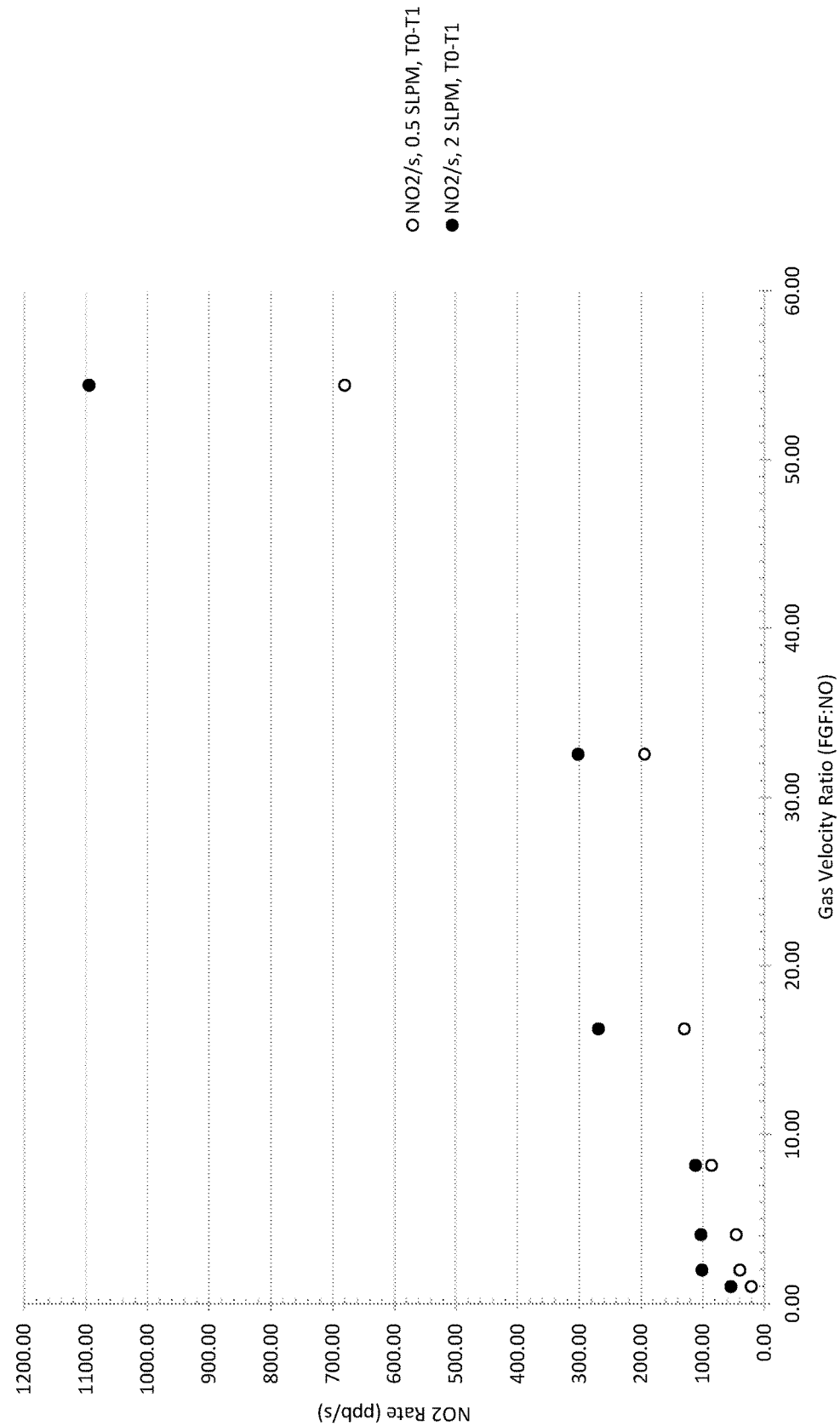

FIG. 17 shows the $NO_2$ generated in the initial T0-T1 region with various NO source cylinder concentrations ranging from 800 ppm to 9760 ppm with a gas velocity ratio (FGF:NO) of approximately 1:1. As can be seen from FIG. 17, by having a gas velocity ratio of approximately 1:1, the $NO_2$ generation rate is comparable between various cylinder concentrations at the same set dose (20 ppm) and the same FGF flow rate (0.5 or 2 SLPM).

FIGS. 18A-D show the $NO_2$ generated in the initial T0-T1 region with various NO source cylinder concentrations ranging from 800 ppm to 9760 ppm with a varying gas velocity ratio (FGF:NO) and a set dose of 10 ppm NO. As can be seen from each of FIGS. 18A-D, gas velocity ratios below 2:1 provide a lower $NO_2$ generation rate than gas velocity ratios above 2:1, even when the NO source concentration, FGF flow rate and the NO set dose are the same.

Figure 19:
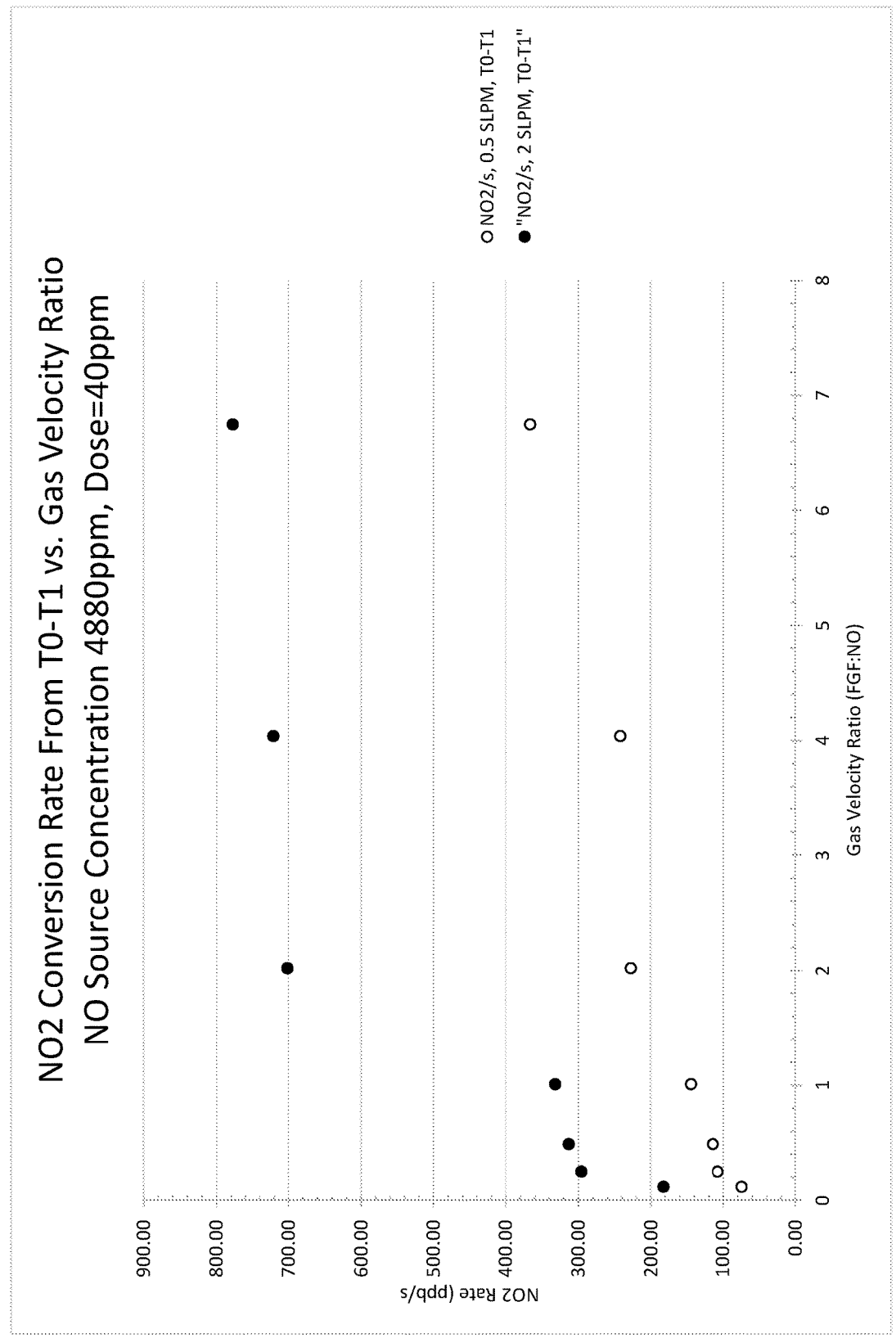
FIG. 19 shows the $NO_2$ generated in the initial region with a 4880 ppm NO source cylinder concentration and a set dose of 40 ppm, with a varying gas velocity ratio (FGF:NO)

FIG. 19 shows the $NO_2$ generated in the initial T0-T1 region with a 4880 ppm NO source cylinder concentration and a set dose of 40 ppm, with a varying gas velocity ratio (FGF:NO). As can be seen by comparing FIG. 19 and FIG. 18C, the relationship between $NO_2$ generation rate and gas velocity ratio is also seen at other set dose concentrations.

Figure 20A:
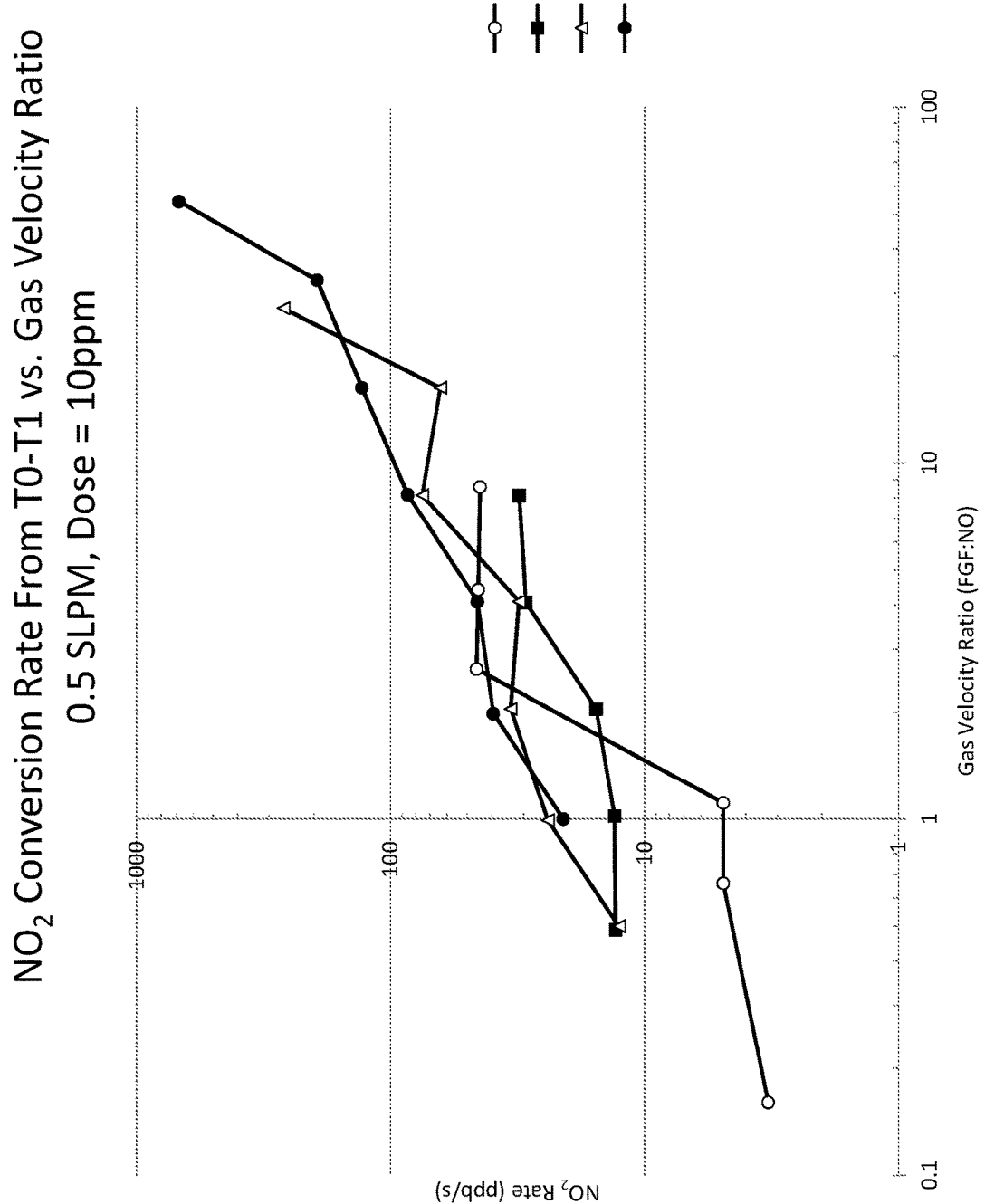
FIGS. 20A-B show the $NO_2$ generated in the initial region with various NO source cylinder concentrations ranging from 800 ppm to 9760 ppm with a varying gas velocity ratio (FGF:NO) and a set dose of 10 ppm NO.
Figure 20B:
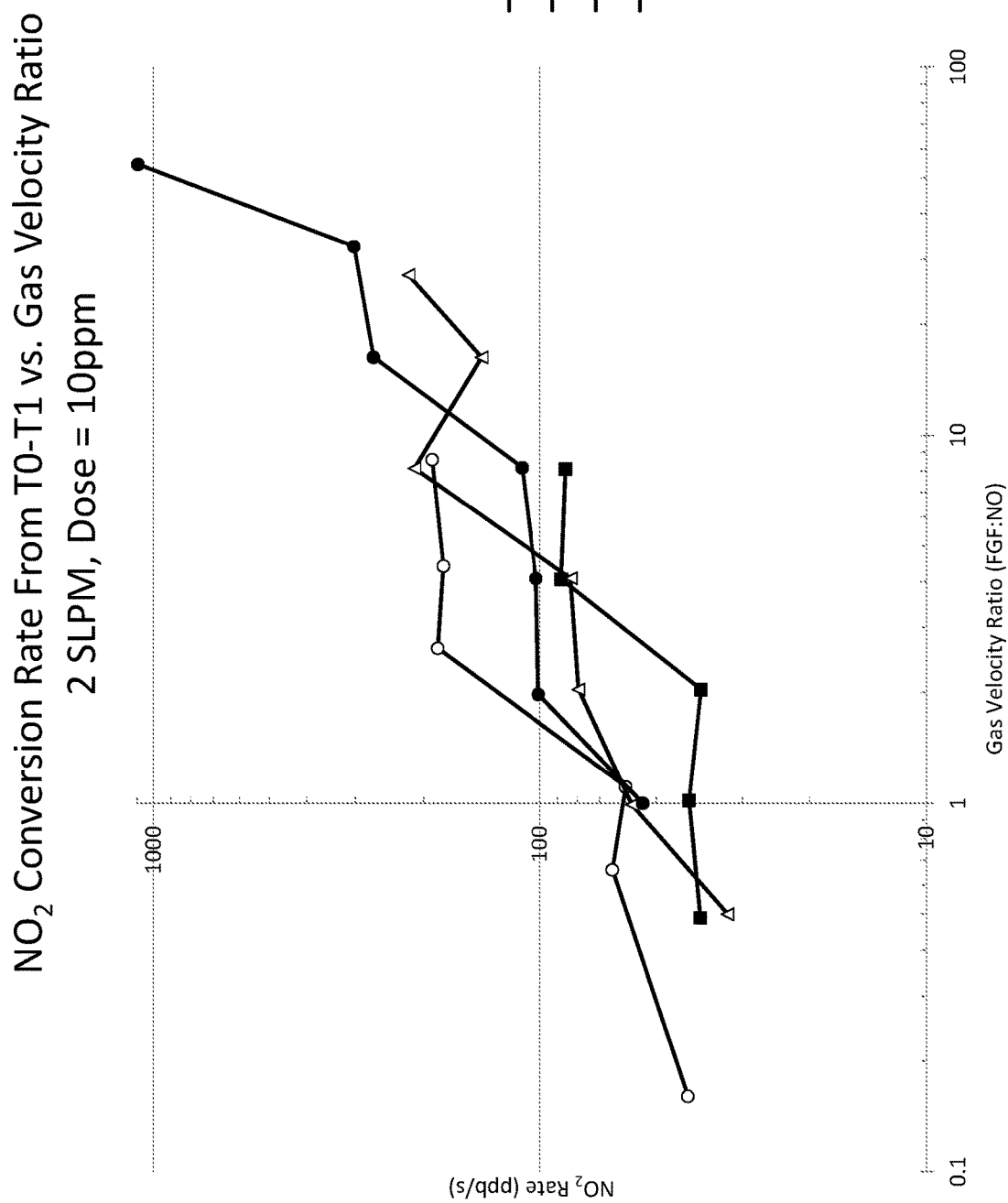

FIGS. 20A-B show the $NO_2$ generated in the initial T0-T1 region with various NO source cylinder concentrations ranging from 800 ppm to 9760 ppm with a varying gas velocity ratio (FGF:NO) and a set dose of 10 ppm NO. As can be seen from FIGS. 20A-B, gas velocity ratios below 2:1 provide a lower $NO_2$ generation rate than gas velocity ratios above 2:1, even when the NO source concentration, FGF flow rate and the NO set dose are the same. As FIGS. 20A-B are plotted on a logarithmic base 10 scale for both the x and y axes, this demonstrates that the instantaneous $NO_2$ generation is non-linear.

Figure 21:
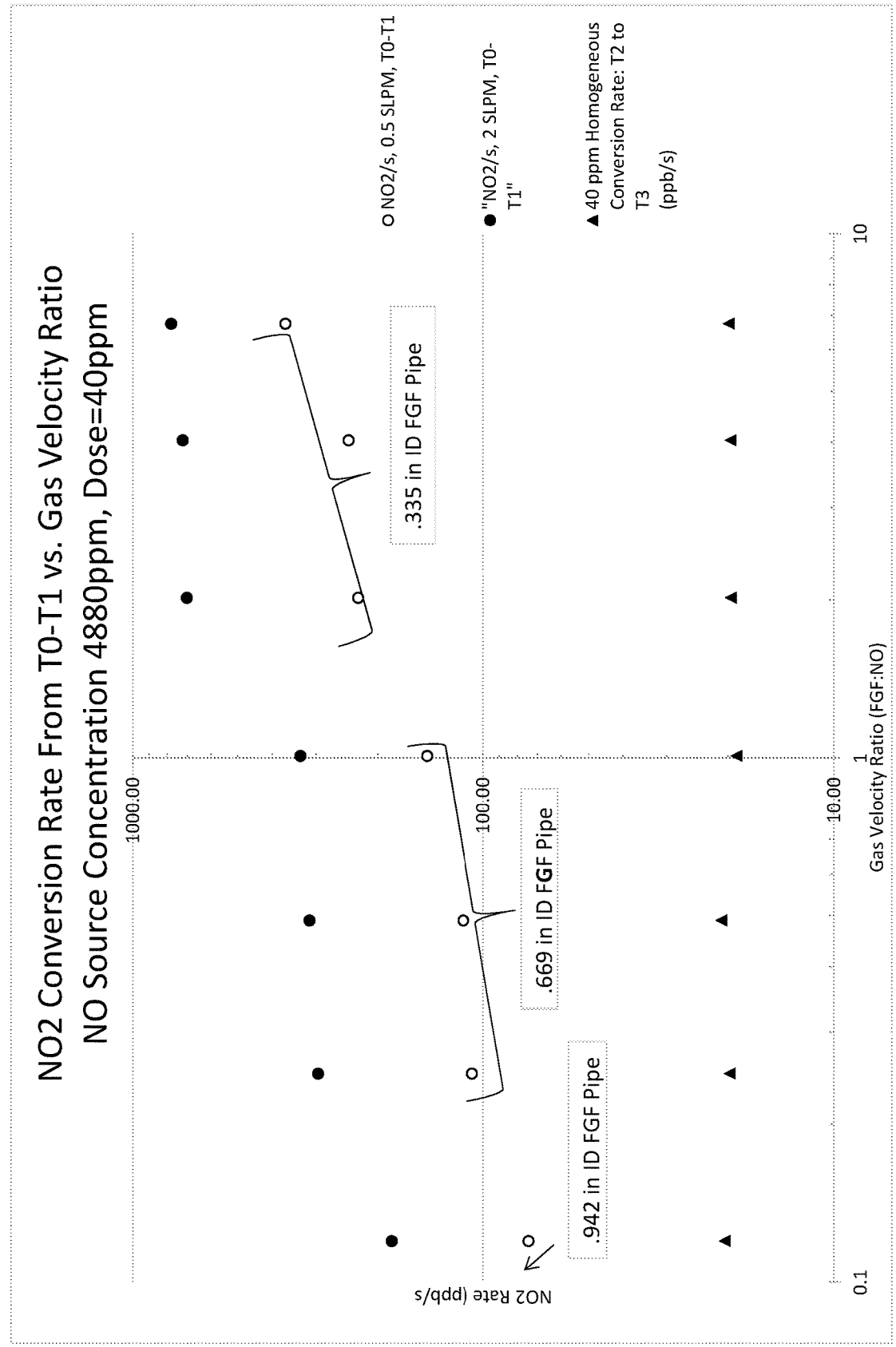
FIG. 21 shows the $NO_2$ generated in the initial region with a 4880 ppm NO source cylinder concentration and a set dose of 40 ppm, with a varying gas velocity ratio (FGF:NO); and $NO_2$ generated during homogeneous phase of 40 ppm equal to set dose.

FIG. 21 shows the $NO_2$ generated in the initial T0-T1 region with a 4880 ppm NO source cylinder concentration and a set dose of 40 ppm, with a varying gas velocity ratio (FGF:NO). FIG. 21 also shows the average $NO_2$ generation rate from T2 to T3. As can be seen from FIG. 21, the $NO_2$ generation rate from T0-T1 is significantly higher than the $NO_2$ generation rate from T2 to T3. Also, the $NO_2$ generation rate from T2 to T3 (shown in triangles) does not vary with the gas velocity ratio, showing that a constant rate of $NO_2$ generation rate is achieved after the combined gas stream reaches a homogenous phase at T2. FIG. 21 further provides the size of the inner diameter of the FGF pipe for each configuration: 0.942 in, 0.669 in or 0.335 in. As can be seen, decreasing the FGF pipe diameter did not reduce $NO_2$ generation, but instead resulted in higher $NO_2$ generation rates. This is consistent with the observed phenomenon of $NO_2$ generation being minimized with lower FGF:NO velocity ratios, particularly those below 2:1.

Example 4—$NO_2$ Generation During Cycling Flow

Figure 22A:
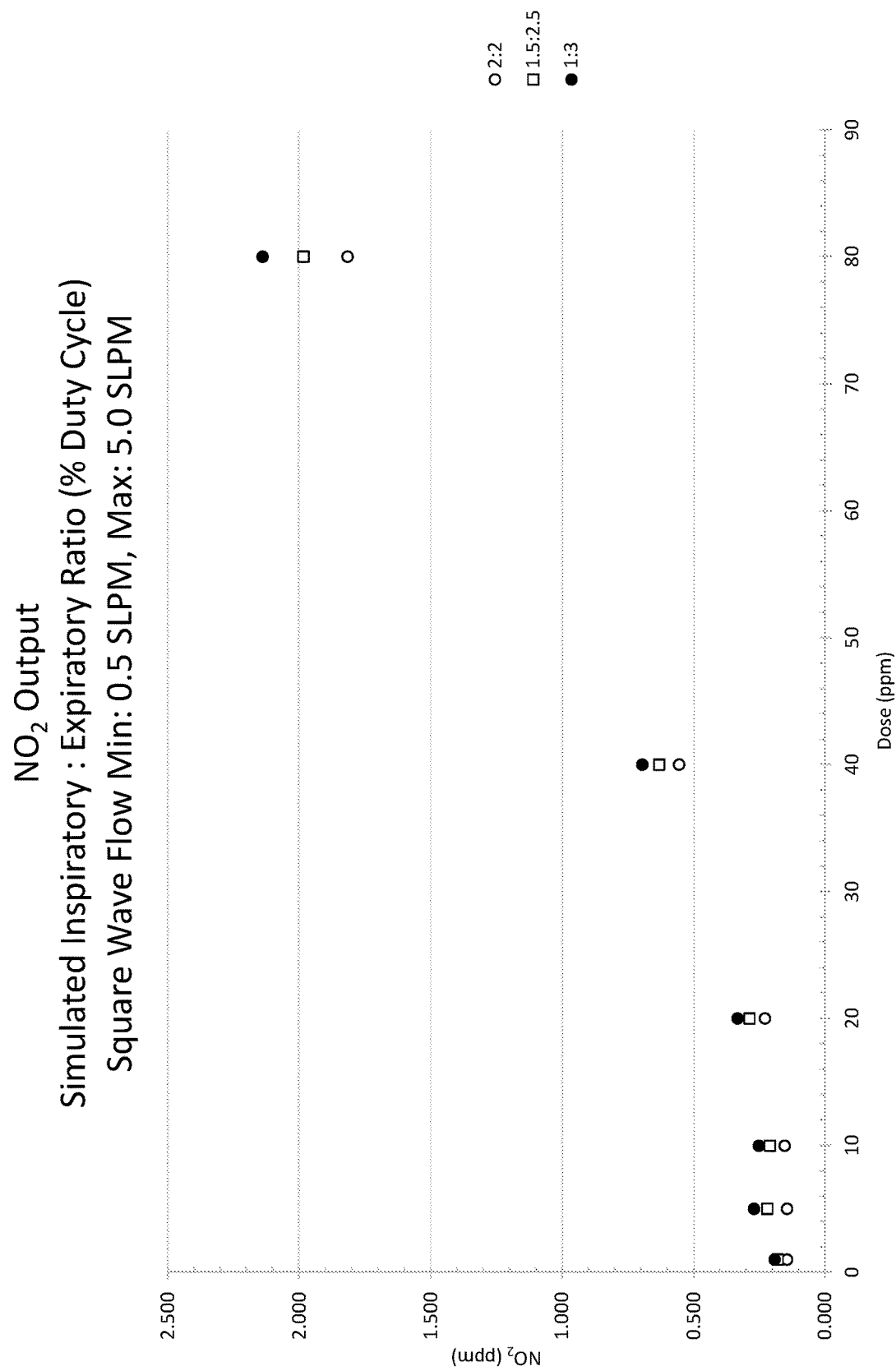
FIGS. 22A-B show the $NO_2$ generated in ppm and as a percentage of the set dose with simulation of expiratory time period change relative to inspiratory time period with higher flows.
Figure 22B:
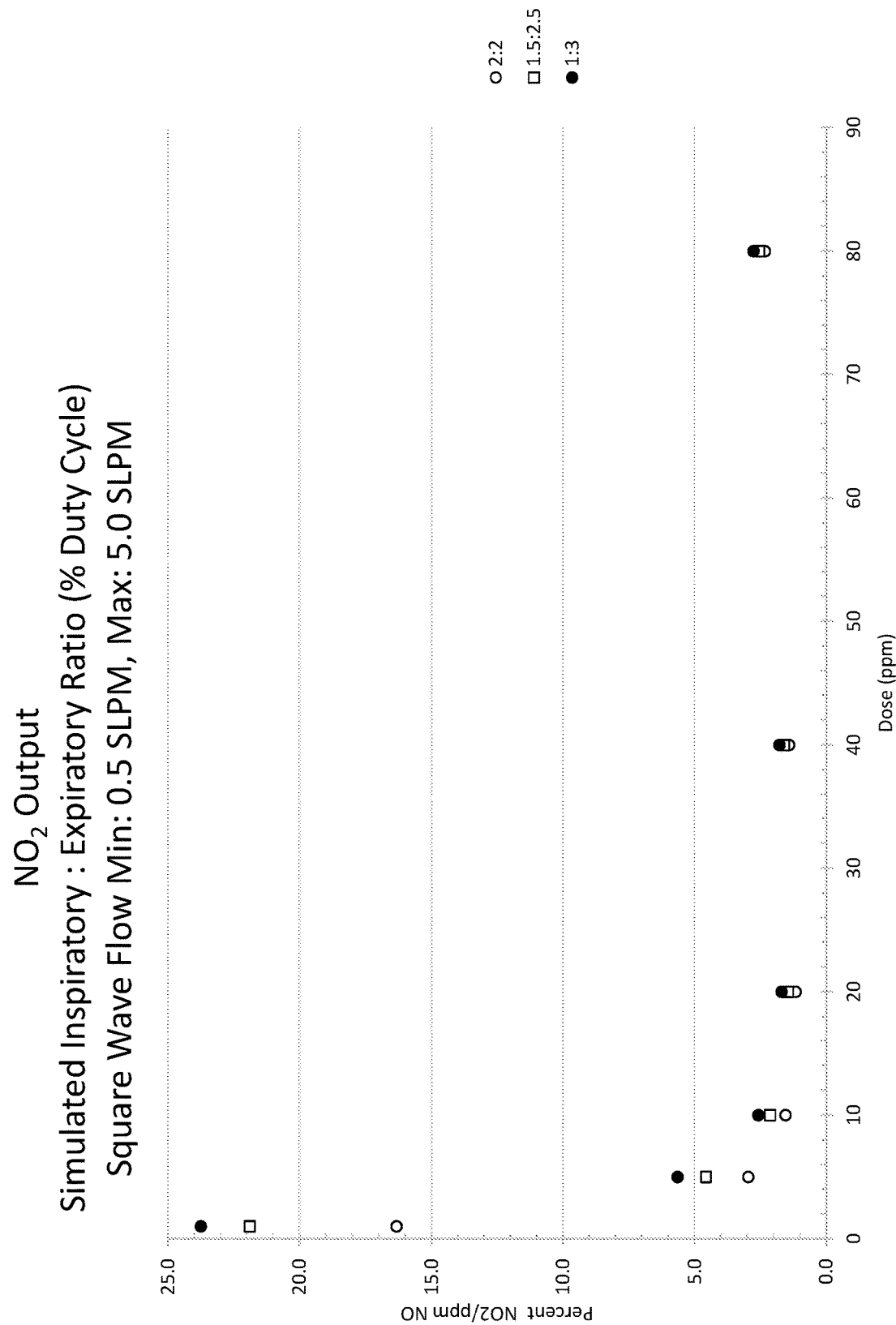

The NO delivery system of Example 3 was modified to simulate a ventilator with varying flow rates. A square wave flow with a minimum flow of 0.5 SLPM and a maximum flow of 5 SLPM was used, with a varying inspiratory to expiratory ratio (high to low flow ratio) ranging from 2:2 to 1:3. FIGS. 22A-B show the NO2 generated in ppm and as a percentage of the set dose of NO. As can be seen from FIGS. 22A-B, the most $NO_2$ was generated with a higher expiratory (low flow) ratio. As can be seen from FIG. 22B, a high percentage of the NO was converted to $NO_2$ at the low set doses, with almost 25% of the NO being converted to $NO_2$ when the inspiratory:expiratory ratio was 1:3 and the NO set dose was 1 ppm.

Example 5: $NO_2$ Generation System Comparison

The $NO_2$ generation rate of a NO delivery system utilizing a suspended funnel (System 3 of Example 1) and the NO delivery system of Example 3 was compared from T0 to T1 at a set dose of 10 ppm NO and a cylinder concentration of 4880 ppm NO. The results of this comparison are shown in Table 4 below.

TABLE 4

$NO_2$ Generation for Systems 3 of Example 1 and Systems of Example 3

| | | $NO_2$ Generation Rate (ppb/s) | | | |
|---|---|---|---|---|---|
| | | Suspended Funnel | Diffuser with Gas Velocity Ratio (FGF:NO) 2:1 | Diffuser with Gas Velocity Ratio (FGF:NO) 1:1 | Diffuser with Gas Velocity Ratio (FGF:NO) 0.5:1 |
| FGF Flow Rate (SLPM) | 0.5 | 32 | 32 | 24 | 13 |
| | 2 | 73 | 79 | 58 | 33 |

As can be seen from Table 4, the suspended funnel design performed comparably to a diffuser with a gas velocity ratio of about 2:1. However, diffusers with velocity ratios below 2:1 (1:1 or 0.5:1) provided lower $NO_2$ generation rates than the suspended funnel design.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

What is claimed is:

1. A diffusing device for injecting a high concentration gas into a transverse gas stream, the diffusion device comprising:
    a body comprising a wall having a thickness, an outer surface, and an inner surface surrounding a hollow internal region;
    a projection extending from the inner surface of the body and into the hollow internal region; and
    an injection channel passing through the wall and projection to an injection port such that the injection port injects the high concentration gas into the transverse gas stream at a distance from the inner surface of the body, wherein the injection port has an outlet recessed from a center of the hollow internal region, and wherein an orifice is located within the flow path of the injection channel and injection port, and the orifice size provides a ratio of the velocity of the transverse gas and the velocity of the high concentration gas, wherein the ratio is less than 2:1.

2. The diffusing device of claim 1, wherein the hollow internal region has a diameter, and a length of the projection from the inner surface to the injection port outlet is in the range of about 30% to about 45% of the diameter of the hollow internal region.

3. The diffusing device of claim 1, wherein the injection port has an inside diameter in the range of about 0.7 mm to about 2.4 mm.

4. The diffusing device of claim 1, wherein the body is an annular body comprising a cylindrical wall having an outside diameter in the range of about 10 mm to about 25 mm, and an inside diameter in the range of about 10 mm to about 25 mm, wherein the inside diameter is smaller than the outside diameter by the thickness of the cylindrical wall.

5. The diffusing device of claim 4, wherein the thickness of the cylindrical wall is in the range of about 1 mm to about 3.175 mm, and the injection channel forms an angle in the range of about 60° to about 120° with a longitudinal axis of the hollow internal region.

6. The diffusing device of claim 1, wherein the diffusing device is configured and dimensioned for insertion into respiratory tubing.

7. The diffusing device of claim 1, wherein the diffusing device is integral to an injector module comprising a flow sensor.

8. The diffusing device of claim 1, wherein the diffusing device comprises a plurality of injection ports.

9. The diffusing device of claim 1, wherein one or more of (i) the injection channel or (ii) the injection port has a proportional valve or a variable orifice.

10. The diffusing device of claim 1, further comprising a mixing device comprising a plurality of blades, plates and/or fins.

11. The diffusing device of claim 1, wherein the projection comprises a nozzle.

12. The diffusing device of claim 1, further comprising a female connector configured and dimensioned for connection to a delivery tube carrying the high concentration gas.

13. A method of diffusing a high concentration gas into a transverse gas stream, comprising:
    passing at least a portion of a first gas through a hollow internal region of a body having an inner surface surrounding the hollow internal region; and
    passing a second gas stream through an injection channel to an injection port projecting into the hollow internal region of the body, wherein the second gas stream enters and at least partially diffuses with the first gas stream within the hollow internal region,
    wherein the first gas stream has a first velocity and the second gas stream has a second velocity, and the ratio of the first velocity to the second velocity is less than 2:1.

14. The method of claim 13, wherein the second gas stream initially enters the first gas stream at an angle in the range of about 60° to about 120°.

15. The method of claim 13, wherein the first gas is a breathable gas comprising molecular $N_2$ and molecular $O_2$, and the second gas comprises molecular NO and molecular $N_2$.

16. The method of claim 15, wherein the concentration of NO in the second gas is in the range of greater than 400 ppm to about 10,000 ppm.

17. The method of claim 13, wherein the flow rate of the second gas is linearly proportional to the flow rate of the first gas.

18. The method of claim 13, wherein the ratio of the first velocity to the second velocity is less than or equal to about 1:1.

19. The method of claim 18, wherein the ratio of less than or equal to about 1:1 is provided when the first gas stream has a volumetric flow rate of less than 2 SLPM.

20. The method of claim 13, wherein the second gas stream enters the first gas stream at or near the central midpoint of the highest velocity of the first gas stream.

21. The method of claim 13, wherein the second gas stream is injected into the first gas stream as a plurality of pulses.

22. A method of diffusing a high concentration NO-containing gas into a transverse oxygen-containing gas stream, the method comprising:
    receiving a dose of NO from a user;
    receiving a first gas stream comprising oxygen through a hollow internal region of a body having an inner surface surrounding the hollow internal region; and
    passing a second gas stream comprising NO through an injection channel to an injection port projecting into the hollow internal region of the body, wherein the second gas stream enters and at least partially diffuses with the first gas stream within the hollow internal region, wherein the injection port has an outlet recessed from a center of the hollow internal region and wherein an orifice is located within the flow path of the injection channel and injection port, and the orifice size provides a ratio of the velocity of the first gas and the velocity of the second gas, wherein the ratio is less than 2:1.

23. The method of claim 22, wherein the ratio of less than 2:1 is provided when the first gas stream has a volumetric flow rate of less than 2 SLPM.

24. The method of claim 22, further comprising selecting an orifice size of a variable-sized orifice.

25. The method of claim 22, further comprising selecting an orifice from a plurality of orifices having varying orifice diameters.

26. The method of claim 22, wherein the second gas stream is injected into the first gas stream as a plurality of pulses to provide the set dose of NO in a combined gas stream of the first gas stream and the second gas stream.

* * * * *